US011939383B2

(12) United States Patent
Kaplan et al.

(10) Patent No.: US 11,939,383 B2
(45) Date of Patent: Mar. 26, 2024

(54) B7-H4 ANTIBODIES AND METHODS AND USE THEREOF

(71) Applicant: Five Prime Therapeutics, Inc., South San Francisco, CA (US)

(72) Inventors: Charles Kaplan, South San Francisco, CA (US); Alessandro Palumbo, South San Francisco, CA (US); Kathy Miller, South San Francisco, CA (US); Hangil Park, South San Francisco, CA (US); Nerissa Mendoza, South San Francisco, CA (US); Majid Ghoddusi, South San Francisco, CA (US)

(73) Assignee: FIVE PRIME THERAPEUTICS, INC., South San Francisco, CA (US)

( * ) Notice: Subject to any disclaimer, the term of this patent is extended or adjusted under 35 U.S.C. 154(b) by 881 days.

(21) Appl. No.: 17/006,670

(22) Filed: Aug. 28, 2020

(65) Prior Publication Data
US 2021/0079096 A1    Mar. 18, 2021

Related U.S. Application Data

(63) Continuation of application No. PCT/US2019/020189, filed on Mar. 1, 2019.
(Continued)

(51) Int. Cl.
*C07K 16/18* (2006.01)
*A61K 39/00* (2006.01)
(Continued)

(52) U.S. Cl.
CPC ... *C07K 16/2827* (2013.01); *G01N 33/57492* (2013.01); *C07K 2317/56* (2013.01);
(Continued)

(58) Field of Classification Search
None
See application file for complete search history.

(56) References Cited

U.S. PATENT DOCUMENTS 3,817,837 A   6/1974   Rubenstein
3,850,752 A   11/1974  Schuurs
(Continued)

FOREIGN PATENT DOCUMENTS

EP   1331266 A1   7/2003
WO   198605807 A1   10/1986
(Continued)

OTHER PUBLICATIONS

Anderson, G.L et al. (Jan. 6, 2010). "Assessing Lead Time of Selected Ovarian Cancer Biomarkers: a Nested Case-control Study," Journal of the National Cancer Institute 102(1):26-38.
(Continued)

*Primary Examiner* — Aurora M Fontainhas
(74) *Attorney, Agent, or Firm* — MARSHALL, GERSTEIN & BORUN LLP

(57) ABSTRACT

The present disclosure provides antibodies and antigen-binding fragments thereof that specifically bind to human B7-H4. The anti-B7-H4 antibodies or antigen-binding fragments thereof are useful, for example in detecting B7-H4. Immunohistochemistry (IHC) can be used to detect B7-H4. The present disclosure also provides methods for treating cancer wherein increased B7-H4 has been detected, by administering a therapeutic anti-B7-H4 antibody or antigen-binding fragment thereof.

17 Claims, 7 Drawing Sheets

Specification includes a Sequence Listing.

US 11,939,383 B2

Page 2

Related U.S. Application Data

(60) Provisional application No. 62/637,740, filed on Mar. 2, 2018.

(51) Int. Cl.
*A61K 39/395* (2006.01)
*A61P 35/00* (2006.01)
*C07K 16/28* (2006.01)
*G01N 33/574* (2006.01)

(52) U.S. Cl.
CPC .................. *C07K 2317/565* (2013.01); *G01N 2333/70532* (2013.01)

(56) References Cited

U.S. PATENT DOCUMENTS

| | | | |
|---|---|---|---|
| 3,939,350 A | 2/1976 | Kronick | |
| 3,996,345 A | 12/1976 | Ullman | |
| 4,275,149 A | 6/1981 | Litman | |
| 4,277,437 A | 7/1981 | Maggio | |
| 4,366,241 A | 12/1982 | Tom | |
| 4,472,509 A | 9/1984 | Gansow | |
| 4,938,948 A | 7/1990 | Ring | |
| 5,122,464 A | 6/1992 | Wilson | |
| 5,196,066 A | 3/1993 | Kusuda | |
| 5,223,409 A | 6/1993 | Ladner et al. | |
| 5,225,539 A | 7/1993 | Winter | |
| 5,403,484 A | 4/1995 | Ladner | |
| 5,427,908 A | 6/1995 | Dower | |
| 5,516,637 A | 5/1996 | Huang | |
| 5,571,698 A | 11/1996 | Ladner | |
| 5,580,717 A | 12/1996 | Dower | |
| 5,585,097 A | 12/1996 | Bolt | |
| 5,624,821 A | 4/1997 | Winter | |
| 5,648,260 A | 7/1997 | Winter | |
| 5,658,727 A | 8/1997 | Barbas | |
| 5,677,425 A | 10/1997 | Bodmer | |
| 5,693,780 A | 12/1997 | Newman | |
| 5,698,426 A | 12/1997 | Huse | |
| 5,733,743 A | 3/1998 | Johnson et al. | |
| 5,750,753 A | 5/1998 | Kimae | |
| 5,780,225 A | 7/1998 | Wigler | |
| 5,807,715 A | 9/1998 | Morrison | |
| 5,821,047 A | 10/1998 | Garrard | |
| 5,869,046 A | 2/1999 | Presta | |
| 5,965,726 A | 10/1999 | Pavlakis | |
| 5,969,108 A | 10/1999 | Mccafferty | |
| 6,121,022 A | 9/2000 | Presta | |
| 6,165,745 A | 12/2000 | Ward | |
| 6,174,666 B1 | 1/2001 | Pavlakis | |
| 6,194,551 B1 | 2/2001 | Idusogie | |
| 6,277,022 B1 | 8/2001 | Melin | |
| 6,291,664 B1 | 9/2001 | Pavlakis | |
| 6,414,132 B1 | 7/2002 | Pavlakis | |
| 6,602,684 B1 | 8/2003 | Umana | |
| 6,737,056 B1 | 5/2004 | Presta | |
| 6,794,498 B2 | 9/2004 | Pavlakis | |
| 6,891,030 B2 | 5/2005 | Chen | |
| 6,946,292 B2 | 9/2005 | Kanda | |
| 7,214,775 B2 | 5/2007 | Hanai | |
| 7,304,149 B2 | 12/2007 | Murphy | |
| 7,504,256 B1 | 3/2009 | Ogawa | |
| 7,619,068 B2 | 11/2009 | Pilkington | |
| 7,622,565 B2 | 11/2009 | Chen | |
| 7,658,921 B2 | 2/2010 | Dall | |
| 7,687,061 B2 | 3/2010 | Hanai | |
| 7,709,226 B2 | 5/2010 | Foote | |
| 7,875,702 B2 | 1/2011 | Chen | |
| 7,888,477 B2 | 2/2011 | Bangur | |
| 7,931,896 B2 | 4/2011 | Chen | |
| 7,964,195 B2 | 6/2011 | Papkoff | |
| 8,129,347 B2 | 3/2012 | Chen | |
| 8,182,813 B2 | 5/2012 | Brasel | |
| 8,206,715 B2 | 6/2012 | Wong | |
| 8,236,767 B2 | 8/2012 | Chen | |
| 8,263,079 B2 | 9/2012 | Doody | |
| 8,323,645 B2 | 12/2012 | Veiby | |
| 8,444,971 B2 | 5/2013 | Papkoff | |
| 8,513,199 B2 | 8/2013 | Brasel | |
| 8,591,886 B2 | 11/2013 | Ponath | |
| 8,609,816 B2 | 12/2013 | Korman | |
| 8,652,465 B2 | 2/2014 | Freeman | |
| 8,703,916 B2 | 4/2014 | Chen | |
| 8,759,490 B2 | 6/2014 | Veiby | |
| 8,906,369 B2 | 12/2014 | Papkoff | |
| 9,005,616 B2 | 4/2015 | Langermann | |
| 9,011,853 B2 | 4/2015 | Langermann | |
| 9,121,853 B2 | 9/2015 | Kwon | |
| 9,221,910 B2 | 12/2015 | Fertig | |
| 9,279,008 B2 | 3/2016 | Scholler | |
| 9,296,822 B2 | 3/2016 | Korman | |
| 9,421,277 B2 | 8/2016 | Veiby | |
| 9,422,351 B2 | 8/2016 | Scholler | |
| 9,447,186 B2 | 9/2016 | Zang | |
| 9,555,124 B2 | 1/2017 | Chen | |
| 9,562,099 B2 | 2/2017 | Leong | |
| 9,574,000 B2 | 2/2017 | Langermann | |
| 9,676,854 B2 | 6/2017 | Liu | |
| 9,926,378 B2 | 3/2018 | Veiby | |
| 9,957,312 B2 | 5/2018 | Langermann | |
| 10,059,768 B2 | 8/2018 | Leong | |
| 11,306,144 B2 * | 4/2022 | Kaplan | G01N 33/57492 |
| 2003/0055224 A1 | 3/2003 | Gao | |
| 2003/0060612 A1 | 3/2003 | Goddard | |
| 2003/0165504 A1 | 9/2003 | Retter | |
| 2003/0181692 A1 | 9/2003 | Ni | |
| 2003/0208058 A1 | 11/2003 | Fiscella | |
| 2004/0014194 A1 | 1/2004 | Beyer | |
| 2004/0126807 A1 | 7/2004 | Goddard | |
| 2005/0163772 A1 | 7/2005 | Dong | |
| 2006/0088523 A1 | 4/2006 | Andya | |
| 2006/0223077 A1 | 10/2006 | Ni | |
| 2006/0253928 A1 | 11/2006 | Bakker | |
| 2007/0036783 A1 | 2/2007 | Humeau | |
| 2007/0178551 A1 | 8/2007 | Gerngross | |
| 2007/0218032 A1 | 9/2007 | Kwon | |
| 2007/0248600 A1 | 10/2007 | Hansen | |
| 2008/0050370 A1 | 2/2008 | Glaser | |
| 2008/0060092 A1 | 3/2008 | Dickey | |
| 2008/0206235 A1 | 8/2008 | Chen | |
| 2009/0005301 A1 | 1/2009 | Ni | |
| 2009/0118175 A1 | 5/2009 | Macina | |
| 2009/0176317 A1 | 7/2009 | Kwon | |
| 2011/0020325 A1 | 1/2011 | Kwon | |
| 2011/0085970 A1 | 4/2011 | Terrett | |
| 2012/0014947 A1 | 1/2012 | Fu | |
| 2013/0078234 A1 | 3/2013 | Takahashi | |
| 2014/0037551 A1 | 2/2014 | Zang et al. | |
| 2014/0294861 A1 | 10/2014 | Scholler et al. | |
| 2014/0322129 A1 | 10/2014 | Leong | |
| 2014/0335541 A1 | 11/2014 | Kwon | |
| 2014/0356364 A1 | 12/2014 | Liu et al. | |
| 2014/0364585 A1 | 12/2014 | Zhang | |
| 2015/0315275 A1 | 11/2015 | Liu et al. | |
| 2016/0017040 A1 | 1/2016 | Leong | |
| 2016/0146806 A1 | 5/2016 | Langermann | |
| 2016/0159910 A1 | 6/2016 | Leong | |
| 2016/0185870 A1 | 6/2016 | Van Eenennaam | |
| 2016/0304581 A1 | 10/2016 | Zang | |
| 2016/0304607 A1 | 10/2016 | Sadineni | |
| 2017/0015758 A1 | 1/2017 | Hammond | |
| 2017/0029525 A1 | 2/2017 | Zang | |
| 2017/0044268 A1 | 2/2017 | Gurney | |
| 2017/0143827 A1 | 5/2017 | Sadineni | |
| 2017/0158771 A1 | 6/2017 | Glennie | |
| 2017/0204185 A1 | 7/2017 | Chen | |
| 2017/0233808 A1 | 8/2017 | Haining | |
| 2017/0334999 A1 | 11/2017 | Sathyanarayanan | |
| 2018/0106862 A1 | 4/2018 | Whetsel | |
| 2018/0106864 A1 | 4/2018 | Moeneclaey | |
| 2018/0118831 A1 | 5/2018 | Epstein | |
| 2018/0186878 A1 | 7/2018 | Rosenthal | |

(56) References Cited

U.S. PATENT DOCUMENTS

| | | |
|---|---|---|
| 2019/0085080 A1 | 3/2019 | Kaplan |
| 2020/0081497 A1 | 3/2020 | Hung et al. |
| 2020/0255528 A1 | 8/2020 | Kaplan |

FOREIGN PATENT DOCUMENTS

| | | |
|---|---|---|
| WO | 198901036 A1 | 2/1989 |
| WO | 199002809 A1 | 3/1990 |
| WO | 199110737 A1 | 7/1991 |
| WO | 199201047 A1 | 1/1992 |
| WO | 199218619 A1 | 10/1992 |
| WO | 199311236 A1 | 6/1993 |
| WO | 199429351 A2 | 12/1994 |
| WO | 199429351 A3 | 2/1995 |
| WO | 199515982 A2 | 6/1995 |
| WO | 199520401 A1 | 8/1995 |
| WO | 199515982 A3 | 12/1995 |
| WO | 199713844 A1 | 4/1997 |
| WO | 199734631 A1 | 9/1997 |
| WO | 199823289 A1 | 6/1998 |
| WO | 199954342 A1 | 10/1999 |
| WO | 200036107 A2 | 6/2000 |
| WO | 200042072 A2 | 7/2000 |
| WO | 200061739 A1 | 10/2000 |
| WO | 200042072 A3 | 11/2000 |
| WO | 200036107 A3 | 2/2001 |
| WO | 200129246 A1 | 4/2001 |
| WO | 200140269 A2 | 6/2001 |
| WO | 200162891 A2 | 8/2001 |
| WO | 200140269 A3 | 12/2001 |
| WO | 200202587 A1 | 1/2002 |
| WO | 200206317 A2 | 1/2002 |
| WO | 200210187 A1 | 2/2002 |
| WO | 200216581 A2 | 2/2002 |
| WO | 200230954 A1 | 4/2002 |
| WO | 200231140 A1 | 4/2002 |
| WO | 2002060919 A2 | 8/2002 |
| WO | 2002060919 A3 | 8/2002 |
| WO | 2002062203 A2 | 8/2002 |
| WO | 2002071928 A2 | 9/2002 |
| WO | 200216581 A3 | 1/2003 |
| WO | 2003004989 A2 | 1/2003 |
| WO | 2002062203 A3 | 2/2003 |
| WO | 2003011878 A2 | 2/2003 |
| WO | 2002071928 A3 | 3/2003 |
| WO | 2003004989 A3 | 3/2003 |
| WO | 200162891 A3 | 7/2003 |
| WO | 200206317 A3 | 7/2003 |
| WO | 2003076579 A2 | 9/2003 |
| WO | 2003011878 A3 | 11/2003 |
| WO | 2003097802 A2 | 11/2003 |
| WO | 2003097803 A2 | 11/2003 |
| WO | 2003101400 A2 | 12/2003 |
| WO | 2003104399 A2 | 12/2003 |
| WO | 2003104438 A2 | 12/2003 |
| WO | 2004000221 A2 | 12/2003 |
| WO | 2004000221 A3 | 7/2004 |
| WO | 2004058167 A2 | 7/2004 |
| WO | 2004065540 A2 | 8/2004 |
| WO | 2003076579 A3 | 9/2004 |
| WO | 2004101756 A2 | 11/2004 |
| WO | 2003097802 A3 | 12/2004 |
| WO | 2004113500 A2 | 12/2004 |
| WO | 2004058167 A3 | 1/2005 |
| WO | 2004065540 A3 | 3/2005 |
| WO | 2005035724 A2 | 4/2005 |
| WO | 2004101756 A3 | 6/2005 |
| WO | 2005051990 A2 | 6/2005 |
| WO | 2005052121 A2 | 6/2005 |
| WO | 2003104438 A3 | 7/2005 |
| WO | 2005062788 A2 | 7/2005 |
| WO | 2004113500 A3 | 8/2005 |
| WO | 2005051990 A3 | 8/2005 |
| WO | 2003101400 A3 | 9/2005 |
| WO | 2003104399 A3 | 9/2005 |
| WO | 2003097803 A3 | 5/2006 |
| WO | 2006053110 A2 | 5/2006 |
| WO | 2005035724 A3 | 6/2006 |
| WO | 2005052121 A3 | 6/2006 |
| WO | 2006074418 A2 | 7/2006 |
| WO | 2006098887 A2 | 9/2006 |
| WO | 2005062788 A3 | 10/2006 |
| WO | 2006104677 A2 | 10/2006 |
| WO | 2006105021 A2 | 10/2006 |
| WO | 2006104677 A3 | 11/2006 |
| WO | 2006121991 A2 | 11/2006 |
| WO | 2006133396 A2 | 12/2006 |
| WO | 2007001459 A2 | 1/2007 |
| WO | 2007005874 A2 | 1/2007 |
| WO | 2006053110 A3 | 3/2007 |
| WO | 2006105021 A3 | 3/2007 |
| WO | 2006074418 A3 | 4/2007 |
| WO | 2006121991 A3 | 4/2007 |
| WO | 2007039818 A2 | 4/2007 |
| WO | 2007067991 A2 | 6/2007 |
| WO | 2007005874 A3 | 7/2007 |
| WO | 2007082154 A2 | 7/2007 |
| WO | 2006098887 A3 | 8/2007 |
| WO | 2006133396 A3 | 8/2007 |
| WO | 2007039818 A3 | 8/2007 |
| WO | 2007067991 A3 | 9/2007 |
| WO | 2007001459 A3 | 10/2007 |
| WO | 2008067283 A2 | 6/2008 |
| WO | 2008071447 A2 | 6/2008 |
| WO | 2008083228 A2 | 7/2008 |
| WO | 2008083239 A2 | 7/2008 |
| WO | 2008083239 A3 | 8/2008 |
| WO | 2008067283 A3 | 10/2008 |
| WO | 2007082154 A3 | 11/2008 |
| WO | 2008083228 A3 | 11/2008 |
| WO | 2008154333 A2 | 12/2008 |
| WO | 2007001459 A8 | 1/2009 |
| WO | 2009009116 A2 | 1/2009 |
| WO | 2009009116 A3 | 3/2009 |
| WO | 2009036379 A2 | 3/2009 |
| WO | 2009073533 A2 | 6/2009 |
| WO | 2009036379 A3 | 8/2009 |
| WO | 2008154333 A3 | 11/2009 |
| WO | 2009073533 A3 | 11/2009 |
| WO | 2010105256 A1 | 9/2010 |
| WO | 2011020024 A2 | 2/2011 |
| WO | 2011028683 A1 | 3/2011 |
| WO | 2011020024 A3 | 6/2011 |
| WO | 2012009568 A2 | 1/2012 |
| WO | 2012009568 A3 | 4/2012 |
| WO | 2012130831 A1 | 10/2012 |
| WO | 2012145493 A1 | 10/2012 |
| WO | 2013025779 A1 | 2/2013 |
| WO | 2013067492 A1 | 5/2013 |
| WO | 2013079174 A1 | 6/2013 |
| WO | 2014100439 A2 | 6/2014 |
| WO | 2014100483 A1 | 6/2014 |
| WO | 2014100823 A1 | 6/2014 |
| WO | 2014100439 A3 | 9/2014 |
| WO | 2014159835 A1 | 10/2014 |
| WO | 2015017600 A1 | 2/2015 |
| WO | 2015031667 A2 | 3/2015 |
| WO | 2015069770 A1 | 5/2015 |
| WO | 2015031667 A3 | 11/2015 |
| WO | 2016040724 A1 | 3/2016 |
| WO | 2016/070001 A1 | 5/2016 |
| WO | 2016168771 A2 | 10/2016 |
| WO | 2016168771 A3 | 12/2016 |
| WO | 2016197204 A1 | 12/2016 |
| WO | 2017015623 A2 | 1/2017 |
| WO | 2017019846 A1 | 2/2017 |
| WO | 2017015623 A3 | 3/2017 |
| WO | 2017048878 A1 | 3/2017 |
| WO | 2017058754 A1 | 4/2017 |
| WO | 2017079117 A1 | 5/2017 |
| WO | 2017106656 A1 | 6/2017 |
| WO | 2017129790 A1 | 8/2017 |
| WO | 2017147368 A1 | 8/2017 |
| WO | 2017149150 A1 | 9/2017 |

(56) References Cited

FOREIGN PATENT DOCUMENTS

| | | | |
|---|---|---|---|
| WO | 2017201502 A1 | 11/2017 | |
| WO | 2018049474 A1 | 3/2018 | |
| WO | 2018075978 A1 | 4/2018 | |
| WO | 2018078145 A1 | 5/2018 | |
| WO | 2018098363 A2 | 5/2018 | |
| WO | 2018106862 A1 | 6/2018 | |
| WO | 2018106864 A1 | 6/2018 | |
| WO | 2018098363 A3 | 9/2018 | |
| WO | 2019040780 A1 | 2/2019 | |
| WO | 2019165075 A1 | 8/2019 | |
| WO | 2019165077 A1 | 8/2019 | |
| WO | 2019/169212 A1 | 9/2019 | |
| WO | 2020081497 A1 | 4/2020 | |

OTHER PUBLICATIONS

Arigami, T. et al. (2010). "Expression of B7-H4 in Blood of Patients With Gastric Cancer Predicts Tumor Progression and Prognosis," J. Surgical Oncology 102:748-752.

Arnold, J.N. et al. (2007, e-pub. Oct. 9, 2006). "The Impact of Glycosylation on the Biological Function and Structure of Human Immunoglobulins," Annual Review of Immunology 25:21-50.

ATCC Catalog No. PTA-5180—"Mouse Hybridoma: Ovr110 A57. 1," 2 pages.

Ausubel, F. et al. (1987). Current Protocols in Molecular Biology, Greene Publishing and Wiley Interscience, New York, TOC, 7 pages.

Awadallah, N. et al. (Mar. 2008). "Detection of B7-H4 and P53 in Pancreatic Cancer: Potential Role as a Cytological Diagnostic Adjunct," Pancreas 36(2):200-206.

Azuma, T. et al. (Oct. 20, 2009). "Potential Role of Decoy B7-H4 in the Pathogenesis of Rheumatoid Arthritis: a Mouse Model Informed by Clinical Data," PLOS Medicine 6(10):e1000166, pp. 1-15.

Balwit, J.M. et al. (2011). "The iSBTc/SITC Primer on Tumor Immunology and Biological Therapy of Cancer: A Summary of the 2010 Program," J. Translational Medicine 9:18, 15 pages.

Barach, Y.S. et al. (Jan. 2011). "T Cell Conihibition in Prostate Cancer: New Immune Evasion Pathways and Emerging Therapeutics," Trends Mo. Med. 17(1):47-55, 18 pages.

Boyd, S.D. et al. (2016, e-pub. Apr. 8, 2016). "Deep Sequencing and Human Antibody Repertoire Analysis," Current Opinion in Immunology 40:103-109.

Bregar, A. et al. (2017, e-pub. Mar. 25, 2017). "Characterization of Immune Regulatory Molecules B7-H4 and PD-L1 in Low and High Grade Endometrial Tumors," Gynecologic Oncology 145(3):446-452.

Bricogne, G. (1997). "Bayesian Statistical Viewpoint On Structure Determination: Basic Concepts and Examples," Meth Enzymol 276:361-423.

Bricogne, G. (Jan. 1, 1993). "Direct Phase Determination By Entropy Maximization and Likelihood Ranking: Status Report and Perspectives," Acta Crystallogr D Biol Crystallogr D49(Pt 1):37-60.

Brinkman, U. et al. (May 11, 1995). Phage Display Of Disulfide-Stabilized Fv Fragments, J Immunol Methods 182:41-50.

Burton, D.R. et al. (1994). "Human Antibodies From Combinatorial Libraries," Advances in Imniunology 57:191-280.

Carreno, B. et al. (Jun. 2005). "Therapeutic Opportunities in the B7/CD28 Family of Ligands and Receptors," Current Opinion in Pharmacology 5(4):424-430.

Champe, M. et al. (Jan. 20, 1995). "Monoclonal Antibodies That Block the Activity of Leukocyte Function-Associated Antigen 1 Recognize Three Discrete Epitopes in the Inserted Domain of CD11a," J Biol Chem 270:1388-1394.

Chayen, N.E. (Oct. 15, 1997). The Role of Oil in Macromolecular Crystallization, Structure 5(10):1269-1274.

Chen, C. et al. (2011). "Overexpression of B7-H4 in Tumor Infiltrated Dendritic Cells," Journal of Immunoassay and Immunochemistry 32(4):353-364.

Chen, C. et al. (2012). "Induced Expression of B7-H4 on the Surface of Lung Cancer Cell by the Tumor-associated Macrophages: a Potential Mechanism of Immune Escape," Cancer Letters 317(1):99-105.

Chen, C. et al. (Jul. 12, 2016). "Nuclear Localization of B7-H4 in Pulmonary Adenocarcinomas Presenting as a Solitary Pulmonary Nodule," Oncotarget 7(36):58563-58568.

Chen, C. et al. (May 2012), "Increase of Circulating B7-H4-expressing CD68+ Macrophage Correlated With Clinical Stage of Lung Carcinomas," Journal of Immunotherapy 35(4):354-358.

Chen, C. et al. (Sep. 2017). "Analysis of B7-H4 Expression in Metastatic Pleural Adenocarcinoma and Therapeutic Potential of Its Antagonists," BMC Cancer 17(1):652, 6 pages.

Chen, L.J. et al. (Apr. 2011, e-pub. Apr. 26, 2011). "B7-H4 Expression Associates With Cancer Progression and Predicts Patient's Survival in Human Esophageal Squamous Cell Carcinoma," Cancer Immunology Immunotherapy 60 (7):1047-1055.

Chen, X. et al. (Feb. 2017), "Increased B7-H4 Expression During Esophageal Squamous Cell Carcinogenesis is Associated with IL-6/STAT3 Signaling Pathway Activation in Mice," Oncology Letters 13(4):2207-2215.

Chen, Y. et al. (Aug. 19, 2014). "The Coexpression and Clinical Significance of Costimulatory Molecules B7-H1, B7-H3, and B7-H4 in Human Pancreatic Cancer," OncoTargets and Therapy 7:1465-1472.

Cheung, R.C. et al. (Jun. 1990). "Epitope-Specific Antibody Response to the Surface Antigen of Duck Hepatitis B Virus in Infected Ducks," Virology 176(2):546-552.

Chinnadurai, R. et al. (Dec. 2010). "B7-H4 Mediates Inhibition of T Cell Responses by Activated Murine Hepatic Stellate Cells," Hepatology 52(6):2177-2185.

Choi, I.H. et al. (2003). "Genomic Organization and Expression Analysis of B7-H4, an Immune Inhibitory Molecule of the B7 Family," Journal of Immunology 171(9):4650-4654.

Chothia, C. et al. (Aug. 20, 1987). "Canonical Structures for the Hypervariable Regions of Immunoglobulins," J. Mol. Biol. 196(4):901-917.

Chothia, C. et al. (Oct. 5, 1992). "Structural Repertoire of the Human VH Segments," J Mol Biol 227(3):799-817.

Chumsae, C. et al. (Aug. 19, 2014). "Discovery of a Chemical Modification by Citric Acid in a Recombinant Monoclonal Antibody," Analytical Chemistry 86(18):8932-8936.

Clackson, T. et al. (Aug. 15, 1991). "Making Antibody Fragments Using Phage Display Libraries," Nature 352:624-628.

Coales, S.J. et al. (Mar. 2009). "Epitope Mapping By Amide Hydrogen/Deuterium Exchange Coupled With Immobilization of Antibody, On-Line Proteolysis, Liquid Chromatography and Mass Spectrometry," Rapid Commun. Mass Spectrom. 23(5):639-647.

Cockett, M.I et al. (Jul. 1990). "High Level Expression of Tissue Inhibitor of Metalloproteinases in Chinese Hamster Ovary Cells Using Glutamine Synthetase Gene Amplification," Bio/Technology 8(7):662-667 (Jul. 1990).

Conroy, P.J. et al. (2017, e-pub. Jan. 11, 2017). "Antibodies: From Novel Repertoires to Defining and Refining the Structure of Biologically Important Targets," Methods 116:12-22.

Cui, Y. et al. (Nov. 7, 2016). "B7-H4 is Predictive of Poor Prognosis in Patients With Gastric Cancer," Medical Science Monitor 22:4233-4237.

Cunningham, B.C. et al. (Jun. 2, 1989). "High-Resolution Epitope Mapping of hGH-Receptor Interactions by Alanine-Scanning Mutagenesis," Science 244:1081-1085.

Dall'acqua, W.F. et al. (Aug. 18, 2006). "Properties of Human IgG1s Engineered for Enhanced Binding to the Neonatal Fc Receptor (FcRn)," J Biol Chem 281(33):23514-23524.

Damschroder, M.M. et al. (2004, e-pub. Jun. 26, 2004). "Analysis of Human and Primate CD2 Molecules by Protein Sequence and Epitope Mapping With Anti-Human CD2 Antibodies," 41:998-1000.

Dangaj, D. et al. (Aug. 1, 2013, e-pub. May 2013). "Novel Recombinant Human B7-H4 Antibodies Overcome Tumoral Immune Escape to Potentiate T-cell Antitumnor Responses," Cancer Research 73(15):4820-4829.

(56) References Cited

OTHER PUBLICATIONS

Dangaj, D. et al. (Aug. 2013). "Blocking the B7-H4 Pathway With Novel Recombinant Antibodies Enhances T Cell-Mediated Antitumor Responses," OncoImmunology 2:8 e25913, 3 pages.

Davies, J. et al. (Aug. 20, 2001). "Expression of GnTIII in a Recombinant Anti-CD20 CHO Production Cell Line: Expression of Antibodies With Altered Glycoforms Leads to an Increase in ADCC Through Higher Affinity for FC gamma RIII," Biotechnol. Bioeng. 74(4):288-294.

Driessens, G. et al. (May 2009), "Costimulatory and Coinhibitory Receptors in Anti-Tumor Immunity," Immunol. Rev. 229(1):126-144, 28 pages.

D'aria, M. et al. (May 2009). "Abstract # 1601: B7-H4 (DD-O110) is Overexpressed in Endocervical Adenorcarcinoma in situ and invasive Adenocarcinoma," Cancer Research, retrieved from https//cacerres.aacrjoumals.org/content/59/9_Supplement/1601, last visited Apr. 30, 2020, 4 pages.

Epstein, A.L. (2012). "B7-H4 as a Target for Breast Cancer Immunotherapy," Research Grant W81XWH-11-1-0466, 26 pages.

Estep, P. et al. (Mar./Apr. 2013, e-pub. Mar. 1, 2013). "High Throughput Solution-Based Measurement of Antibody-Antigen Affinity and Epitope Binning," MAbs 5(2):270-278.

Fan, M. et al. (Oct. 1, 2014, e-pub. Sep. 15, 2014). "B7-H4 Expression is Correlated With Tumor Progression and Clinical Outcome in Urothelial Cell Carcinoma," International Journal of Clinical and Experimental Pathology 7(10):6768-6775.

Ferrara, C. et al. (2006, e-pub. Jan. 24, 2006). "Modulation of Therapeutic Antibody Effector Functions by Glycosylation Engineering: Influence of Golgi Enzyme Localization Domain and Co-Expression of Heterologous β1,4-N-Acetylglucosaminyltransferase III and Golgi α-Mannosidase," Biotechnology and Bioengineering 93(5):851-861.

Ferrara, F. et al. (Apr. 2015, e-pub. Dec. 20, 2014). "Recombinant Renewable Polyclonal Antibodies," mAbs 7(1):32-41.

Ferreira, M.M. et al. (Mar. 2016, e-pub. Jan. 28, 2016). "Circulating Tumor Cell Technologies," Molecular Oncology 10(3):374-394.

Filies, D. B. et al. (2007). "The New B7s: Playing a Pivotal Role in Tumor Immunity," J. Immunother. 30:251-260.

Foecking, M.K. et al. (1986). "Powerful and Versatile Enhancer-Promoter Unit For Mammalian Expression Vectors," Gene 45(1):101-105.

Fukuda, T. et al. (2016). "Higher Preoperative Serum Levels of PD-L1 and B7-H4 are Associated with Invasive and Metastatic Potential and Predictable for Poor Response to VEGF-Targeted Therapy and Unfavorable Prognosis of Renal Cell Carcinoma," Cancer Medicine 5(8):1810-1820.

Gao, A. et al. (2015). "Effect of VTCN1 on Progression and Metastasis of Ovarian Carcinoma in Vitro and Vivo," Biomedicine & Pharmacotherapy 73:129-134.

GCC Office Action, dated Jan. 20, 2020, for GCC Patent Application No. GC2018-35987, 6 pages.

Geng, Y. et al. (2015). "Expression of Costimulatory Molecules B7-H1, B7-H4 and Foxp3+ Tregs in Gastric Cancer and Its Clinical Significance," International Journal of Clinical Oncology, 20(2):273-281.

Giegé, R et al. (Jul. 1, 1994). Crystallogenesis of Biological Macromolecules: Facts and Perspectives, Acta Crystallogr D Biol Crystallogr D50(Pt 4):339-350.

Goding, J.W. (1986). "Production of Monoclonal Antibodies," Chapter 3 in Monoclonal Antibodies: Principles and Practice, Academic Press, New York, pp. 59-103.

Goldberg, A. et al. (Dec. 2009). "Abstract C243: B7-H4 Protein Expression in Invasive Ductal Carcinoma and its Association With Tumor Progression," Molecular Cancer Therapeutics, retrieved from https://mct.aacrjournals.org/content/8/12_Supplement/C243, last visited Apr. 30, 2020, 4 pages.

Hammerling, G.J. et al. (1981). "Production of Antibody-Producing Hybridomas in the Rodent Systems," in Research Monographs in Immunology, Elsevier/North-Holland Biomedical Press 3:563-587.

Han, S. et al. (Apr. 2017, e-pubs. Mar. 1, 2017). "Roles of Immune Inhibitory Molecule B7-H4 in Cervical Cancer," Oncology Reports 37(4):2308-2316, 12 pages.

Han, S. et al. (Aug. 2018). "Negative Roles of B7-H3 and B7-H4 in the Microenvironment of Cervical Cancer," Experimental Cell Research, 21 pages.

Hansen, J.D. et al. (2009, e-pub. Dec. 9, 2008). "The B7 Family of Immunoregulatory Receptors: A Comparative and Evolutionary Perspective," Molecular Immunology 46(3):457-472.

Harlow, E. et al. (1988). Antibodies: A Laboratory Manual, Cold Spring Harbor Press, 89 pages.

He, C. et al. (2011). "The Inhibitory Role of B7-H4 in Antitumor Immunity: Association With Cancer Progression and Survival," Clinical & Developmental Immunology 2011:695834, 8 pages.

Herber, D.L. et al. (Jun. 1, 2007). "Meeting Report: Mechanism and Therapeutic Reversal of Immune Suppression in Cancer," Cancer Res. 67(11):5067-5069, 7 pages.

Huang, C. et al. (Apr. 2016, e-pub. Feb. 2, 2016). "B7-H3, B7-H4, Foxp3 and IL-2 Expression in Cervical Cancer: Associations With Patient Outcome and Clinical Significance," Oncology Reports 35(4):2183-2190, 11 pages.

Huang, H. et al. (Apr. 4, 2017). "Clinical Significance of the B7-H4 as a Novel Prognostic Marker in Breast Cancer," Gene, 17 pages.

Ichikawa, M. et al. (Sep. 1, 2005). "Role of B7-H1 and B7-H4 Molecules in Down-Regulating Effector Phase of T-Cell Immunity: Novel Cancer Escaping Mechanisms," Frontiers in Bioscience 10:2856-2860.

Iida, S. et al. (Feb. 18, 2009). "Two Mechanisms of the Enhanced Antibody-dependent Cellular Cytotoxicity (ADCC) Efficacy of Non-fucosylated Therapeutic Antibodies in Human Blood," BMC Cancer 9:58, 12 pages.

Iizuka, A. et al. (Nov. 2016, e-pub. Sep. 12, 2016). "Unstable B7-H4 Cell Surface Expression and T-cell Redirection as a Means of Cancer Therapy," Oncology Reports 36(5):2625-2632, 13 pages.

Imai-Nishiya, H. et al. (Nov. 30, 2007). "Double Knockdown of a1,6-Fucosyltransferase (FUTB) and GDP-Man Nose 4,6-Dehydratase (GMO) In Antibody-Producing Cells: A New Strategy for Generating Fully Non-Fucosylated Therapeutic Antibodies With Enhanced ADCC," BMC Biotechnology 7:84, 13 pages.

International Preliminary Report on Patentability, dated Aug. 27, 2020, for PCT Application No. PCT/ US2019/018965, filed Feb. 21, 2019, 7 pages.

International Preliminary Report on Patentability, dated Aug. 27, 2020, for PCT Application No. PCT/ US2019/018966, filed Feb. 21, 2019, 11 pages.

International Preliminary Report on Patentability, dated Sep. 8, 2020, for PCT Application No. PCT/ US2019/020189, filed Mar. 1, 2019, 6 pages.

International Search Report and Written Opinion, dated Dec. 12, 2018, for PCT Application No. PCT/ US2018/047805, filed Aug. 23, 2018, 25 pages.

International Search Report and Written Opinion, dated Jan. 28, 2020, for PCT Application No. PCT/US2019/056210, filed Oct. 15, 2019, 14 pages.

International Search Report and Written Opinion, Jun. 12, 2019, for PCT Application No. PCT/US2019/018965 filed Feb. 21, 2019, 11 pages.

International Search Report and Written Opinion, Jun. 14, 2019, for PCT Application No. PCT/US2019/018963 filed Feb. 21, 2019, 11 pages.

International Search Report and Written Opinion, dated May 17, 2019, for PCT Application No. PCT/US2019/020189, filed Mar. 1, 2019, 9 pages.

Janakiram, M. et al. (Mar. 2017). "The Third Group of the B7-CD28 Immune Checkpoint Family: HHLA2, TMIGD2, B7x, and B7-H3," Immunological Reviews 276(1):26-39, 28 pages.

Jennewein, M.F. et al. (May 2017). "The Immunoregulatory Roles of Antibody Glycosylation," Trends in Immunology 38(5):358-372, 21 pages.

Jeon, H. et al. (Nov. 2014). "Structure and Cancer Immunotherapy of the B7 Family Member B7x," Cell Reports 9(3):1089-1098.

(56) References Cited

OTHER PUBLICATIONS

Jiang, J. et al. (2010, e-pub. Aug. 20, 2010). "Tumor Expression of B7-H4 Predicts Poor Survival of Patients Suffering From Gastric Cancer," Cancer Immunology 59(11):1707-1714.

Jiang, J.T et al. (2011). "B7-H4 Expression and Increased Death Risk of Cancer Patients: A Meta-Analysis," Journal of Cancer Research and Clinical Oncology 8:229-234.

Jones, P.T. et al. (May 29, 1986). "Replacing the Complementarity-Determing Regions in a Human Antibody With Those From a Mouse," Nature 321:522-525.

Kabat, E.A. et al. (1971). "Attempts To Locate Complementarity-Determining Residues In The Variable Positions of Light and Heavy Chains," Ann NY Acad Sci 190:382-391.

Kabat, E.A et al. (1991). Sequences of Proteins of Immunological Interest, 5th ed., Public Health Service, National Institutes of Health, Bethesda, MD. TOC, 21 pages.

Kamimura, Y. et al. (Aug. 2009, e-pub. Aug. 31, 2009). "Possible Involvement of Soluble B7-H4 in T Cell-mediated Inflammatory Immune Responses," Biochemical and Biophysical Research Communications 389(2):349-353.

Kanda, Y. et al. (Jan. 2007, e-pub. Sep. 29, 2006). "Comparison of Biological Activity Among Nonfucosylated Therapeutic Igg1 Antibodies With Three Different N-Linked Fc Oligosaccharides: The High-Mannose, Hybrid, and Complex Types," Glycobiology 17(1):104-118.

Kaplan, C. et al. (2017). "FPA 150, a Novel B7-H4 Therapeutic Antibody with Checkpoint Blockade and ADCC Activities," Five Prime Therapeutics ADIMAB, 1 page.

Kaplan, C.D. et al. (Sep. 10, 2017). "6PD-FPA150, a Novel B7-H4 Therapeutic Antibody with Checkpoint Blockade and ADCC Activities," European Society for Medical Oncology2 Abstract, 2 pages.

Kettleborough, C.A. et al. (Apr. 1994). "Isolation of Tumor Cell-Specific Single-Chain Fv From Immunized Mice Using Phage-Antibody Libraries and the Re-Construction of Whole Antibodies From These Antibody Fragments," Eur. J. Immunol. 24(4):952-958.

Khan, L. et al. (Mar. 23, 2017). "Cross-Neutralizing Anti-HIV-1 Human Single Chain Variable Fragments(scFvs) Against CD4 Binding Site and N332 Glycan Identified From a Recombinant Phage Library," Sci. Rep. 7:451163, 12 pages.

Kim, J.Y. et al. (May 7, 2017). "Immune Signature of Metastatic Breast Cancer: Identifying Predictive Markers of Immunotherapy Response," Oncotarget 8(29):47400-47411.

Kim, S.J. et al. (Dec. 2007). "Guided Selection of Human Antibody Light Chains Against TAG-72 Using a Phage Display Chain Shuffling Approach," J Microbiol 45(6):572-577.

Kirkland, T.N. et al. (Dec. 1, 1986). "Analysis of the Fine Specificity and Cross-Reactivity of Monoclonal Anti-Lipid A Antibodies," J Immunol 137(11):3614-3619.

Kitamura, H. et al. (Jan.-Mar. 2008). "Prognostic Biomarkers of Renal Cell Carcinoma: Recent Advances," Indian J. Urol. 24(1):10-15, retrieved from https://www.ncbi.nlm.gove/pmc/articles/PMC2684243/?report-printable, last visited Apr. 30, 2020, 12 pages.

Klatte, T et al. (May 20-25, 2006). "Best of the 2006 AUA Annual Meeting: Highlights from the 2006 Annual Meeting of the Am. Urological Assoc.," 8(3): 120-164.

Konitzer, J.D. et al. (2017, e-pub. Feb. 3, 2017). "Generation of a Highly Diverse Panel of Antagonistic Chicken Monoclonal Antibodies Against the GIP Receptor," mAbs 9(3):536-549.

Krambeck, A.E. et al. (Jul. 5, 2006). "B7-H4 Expression in Renal Cell Carcinoma and Tumor Vasculature: Associations With Cancer Progression and Survival," Proc. Nat. Acad. Sci. USA 103(27):10391-10396.

Kryczek, I. et al. (Apr. 17, 2006), "B7-H4 Expression Identifies a Novel Suppressive Macrophage Population in Human Ovarian Carcinoma," The Journal of Experimental Medicine 203(4):871-881.

Kryczek, I. et al. (Sep. 15, 2007). "Relationship Between B7-H4, Regulatory T Cells, and Patient Outcome in Human Ovarian Carcinoma," Cancer Research 67(18):8900-8905.

Kuroki, M. et al. (Aug. 1992). "Biochemical Characterization of 25 Distinct Carcinoembryonic Antigen (CEA) Epitopes Recognized By 57 Monoclonal Antibodies and Categorized Into Seven Groups in Terms of Domain Structure of the CEA Molecule," Hybridoma 11(4):391-407.

Kuroki, M et al. (Oct. 1992, e-pub. Jul. 7, 2009). "Determination of Epitope Specificities of a Large No. of Monoclonal Antibodies By Solid-Phase Mutual Inhibition Assays Using Biotinylated Antigen," Immunol Invest 21 (6):523-538.

Kuroki, M. et al. (Aug. 15, 1990). "Serological Mapping of the TAG-72 Tumor-Associated Antigen Using 19 Distinct Monoclonal Antibodies," Cancer Res 50:4872-4879.

Köhler, G et al. (Aug. 7, 1975). "Continuous Cultures of Fused Cells Secreting Antibody of Predefined Specificity," Nature 256:495-497.

Lee, J. et al. (Dec. 2016). "Molecular-Level Analysis of the Serum Antibody Repertoire in Young Adults Before and After Seasonal Influenza Vaccination," Nature Medicine 22(12):1456-1464, 39 pages.

Lefranc, M.- P. (1999). "The IMGT Unique Numbering for Immunoglobulins, T-Cell Receptors, and Ig-Like Domains," The Immunologist 7(4):132-136.

Lefranc, M.-P. et al. (1999). "IMGT, The International ImMunoGeneTics Databse," Nucleic Acids Res 27(1):209-212.

Leong, S. R. et al. (Apr. 8, 2015). "An Anti-B7-H4 Antibody-drug Conjugate for the Treatment of Breast Cancer," Molecular Pharmaceutics 12(6):1717-1729, 56 pages.

Leung, J. et al. (Jan. 2017, e-pub. Jan. 10, 2017). "Synergistic Effects of Host B7-H4 Deficiency and Gemcitabine Treatment on Tumor Regression and Anti-tumor T Cell Immunity in a Mouse Model," Cancer Immunology 66(4):491-502.

Leung, J. et al. (Jun. 2013). "Host B7-H4 Regulates Antitumor T Cell Responses Through Inhibition of Myeloid-derived Suppressor Cells in a 4T1 Tumor Transplantation Model," Journal of Immunology 190(12):6651-6661, and supplemental information.

Li, J. et al.(Apr. 17, 2018). "Co-inhibitory Molecule B7 Superfamily Member 1 Expressed by Tumor-infiltrating Myeloid Cells Induces Dysfunction of Anti-tumor CD8+ T Cells," Immunity Cell Press 48:773-786.

Li, Y. et al. (Jan. 28, 2009). "Summary of the Primer on Tumor Immunology and the Biological Therapy of Cancer," J. Translational Medicine 7:11, 5 pages.

Liu, J et al. (2015, e-pub. Aug. 28, 2015). "Expression of Immune Checkpoint Molecules in Endometrial Carcinoma," Experimental and Therapeutic Medicine 10(5):1947-1952, 11 pages.

Liu, L. et al. (2016, e-pub. Jul. 13, 2016). "B7-H4 Expression in Human Infiltrating Ductal Carcinoma-Associated Macrophages," Molecular Medicine Report 14(3):2135-2142, 12 pages.

Liu, W-H et al. (2014, e-pub. Sep. 11, 2014). "B7-H4 Expression in Bladder Urothelial Carcinoma and Immune Escape Mechanisms," Oncology Letters 8(6):2527-2534, 12 pages.

Liu, Y. et al. (Mar./Apr. 2014. e-pub. Dec. 6, 2013). "High-Throughput Screening For Developability During Early-Stage Antibody Discovery Using Self-Interaction Nanoparticle Spectroscopy," MAbs 6(2):483-492.

Loke, P. et al. (Aug. 6, 2004). "Emerging Mechanisms of Immune Regulation: The Extended B7 Family and Regulatory T Cells," Arthritis Research & Therapy 6(5):208-214.

Longmore, G.D. et al. (Mar. 1, 1982). "Product-Identification and Substrate-Specificity Studies of the GDP-L-fucose:2-acetamido-2-deoxy-beta-D-glucoside (FUC Goes to Asn-Linked GlcNAc) 6-alpha-L-fucosyltransferase in a Golgi-Rich Fraction From Porcine Liver," Carbohydr Res 100:365-392.

MacCallum, R.M et al. (1996). "Antibody-Antigen Interactions: Contact Analysis and Binding Site Topography," J. Mol. Biol. 262:732-745.

MacGregor, H.-L. et al. (Jun. 15, 2017, e-pub. Mar. 21, 2017). "Molecular Pathways: Evaluating the Potential for B7-H4 as an Immunoregulatory Target," Clinical Cancer Research 23(12):2934-2941.

Mao, Y. et al. (Jun. 2006). "Recombinant Human B7-H4 Expressed in *Escherichia coli* Inhibits T Lymphocyte Proliferation and IL-2 Secretion in Vitro," Acta Pharmacologica Sinica 27(6):741-746.

(56) References Cited

OTHER PUBLICATIONS

Martin, A.C.R. (2001). "Protein Sequence and Structure Analysis of Antibody Variable Domains," in Antibody Engineering, Kontermann and Dithel, eds., Chapter 31, pp. 422-439.

Matsunaga, T. et al. (2011). "Increased B7-H1 and B7-H4 Expressions on Circulating Monocytes and Tumor-associated Macrophages are Involved in Immune Evasion in Patients With Gastric Cancer," Yonago Acta Medica 54 (1):1-10.

McPherson, A. (1990). "Current Approaches To Macromolecular Crystallization," Eur J Biochem 189:1-23.

McPherson, A. (Oct. 25, 1976). "Crystallization of Proteins from Polyethylene Glycol," J Biol Chem 251 (20):6300-6303.

Meng, Z. et al. (Jun. 19, 2017). "B7-H4 as an Independent Prognostic Indicator of Cancer Patients: a Metaanalysis," Oncotarget 8(40):68825-68836.

Miyatake, T. et al. (2007, e-pub. May 16, 2007). "B7-H4 (DD-O110) Is Overexpressed in High Risk Uterine Endometrioid Adenocarcinomas and Inversely Correlated With Tumor T-cell Infiltration," Gynecologic Oncology 106(1):119-127.

Miyatake, T. et al. (Apr. 2006). "B7-H4 (DD-O110) Immunocytochemistry Improves the Sensitivity of Cancer Cell Detection in Pelvic Wash Specimens of Metastatic Ovarian Cancer," Cancer Research, Abstract 4502, retrieved from https://cancerres.aacrjounals.org/content/66/8_Supplement/1056.4, last visited Apr. 30, 2020, 4 pages.

Miyatake, T. et al. (May 2005). "B7-H4 (DD-0110) is Overexpressed in Uterine Endometrioid Carcinomas Independent of Tumor Grade, T Cell Infiltration, or Apoptotic Index," Cancer Research, Abstract 3604, retrieved from https://canceres.aacrjournals.org/content/65/9_Supplement/849.5, last visited May 1, 2020, 4 pages.

Moldenhauer, G. et al. (Aug. 1990). "Identity of HML-1 Antigen on Intestinal Intraepithelial T Cells and of B-ly7 Antigen on Hairy Cell Leukaemia," Scand J Immunol 32(2):77-82.

Morel, G.A. et al. (Jan. 1988). "Monoclonal Antibodies to Bovine Serum Albumin: Affinity and Specificity Determinations," Mol Immunol 25(1):7-15.

Mugler, K.C. et al. (Dec. 2007), "B7-H4 Expression in a Range of Breast Pathology: Correlation With Tumor T-cell Infiltration," Applied Immunohistochemistry and Molecular Morphology 15(4):363-370.

Murillo, O. et al. (Nov. 15, 2013). "Potentiation of Therapeutic Immune Responses Against Malignancies With Monoclonal Antibodies," Clinical Cancer Research 9:5454-5464.

Niwa, R. et al. (Mar. 15, 2005). "Enhanced Natural Killer Cell Binding and Activation by Low-fucose IgG1 Antibody Results in Potent Antibody-dependent Cellular Cytotoxicity Induction at Lower Antigen Density," Clinical Cancer Research 11(6):2327-2336.

Niwa, R. et al. (Sep. 15, 2004). "Enhancement of the Antibody-Dependent Cellular Cytotoxicity of Low-Fucose IgG1 Is Independent of FcγRIIIa Functional Polymorphism," Clin Cancer Res 10:6248-6255.

Ohaegbulam, K. et al. (Sep. 20, 2017). "Tumor-expressed Immune Checkpoint B7X Promotes Cancer Progression and Antigen-Specific CD8 T Cell Exhaustion and Suppressive Innate Immune Cells," Oncotarget 8 (47):82740-82753.

Palena, C. et al. (2010). "Review Article: Vaccines Against Human Carcinomas: Strategies to Improve Antitumor Immune Responses," J. Biomedicine and Biotechnology 2010(380697):1-12.

Parola, C. et al. (2018). "Integrating High-Throughput Screening and Sequencing For Monoclonal Antibody Discovery and Engineering," Immunology 153:31-41.

Persic, L. et al. (Mar. 10, 1997). "An Integrated Vector System for the Eukaryotic Expression of Antibodies or Their Fragments After Selection From Phage Display Libraries," Gene 187(1):9-18.

Podojil, J. et al. (Mar. 2017). "Potential Targeting of B7-H4 for the Treatment of Cancer," Immunological Reviews 276(1):40-51, 22 pages.

Prasad, D. V.R. et al. (Jun. 2003). "B7S1, a Novel B7 Family Member That Negatively Regulates T Cell Activation," Immunity 18(6):863-873.

Presta, L.G. et al. (2002). "Engineering Therapeutic Antibodies for Improved Function," Biochemical Society Transactions 30(4):487-490.

Qian, Y. et al. (2011, e-pub. Dec. 29, 2010). "B7-H4 Expression in Various Tumors Determined Using a Novel Developed Monoclonal Antibody," Clinical and Experimental Medicine 11(3):163-170.

Qian, Y. et al. (Jul. 25, 2011). "Development of a Novel Monoclonal Antibody to B7-H4: Characterization and Biological Activity," European Journal of Medical Research 16(7):295-302.

Rabinovich, G.A. et al. (2007). "Immunosuppressive Strategies That are Mediated By Tumor Cells," Annu. Rev. Immunol. 25:267-296, 34 pages.

Rader, C. et al. (Jul. 1998). "A Phage Display Approach for Rapid Antibody Humanization: Designed Combinatorial V Gene Libraries," PNAS 95:8910-8915.

Rahbar, R. et al. (Feb. 2015, e-pub. Dec. 19, 2014). "B7-H4 Expression by Nonhematopoietic Cells in the Tumor Microenvironment Promotes Antitumor Immunity," Cancer Immunology Research 3(2):184-195.

Rahbar, R. et al. (Jan. 2016, e-pub. Jan. 4, 2016). "B7-H4 is a Positive Regulator of Antitumor Immunity," Oncoimmunology, 5(1):e1050575, 3 pages.

Raju, T.S. (Apr. 2003). "Glycosylation Variations with Expression Systems and Their Impact on Biological Activity of Therapeutic Immunoglobulins," BioProcess International 1(4): 44-53.

Riechmann, L. et al. (Mar. 24, 1988). "Reshaping Human Antibodies for Therapy," Nature 332:323-329.

Roguska, M.A. et al. (Feb. 1994). "Humanization of Murine Monoclonal Antibodies Through Variable Domain Resurfacing." Proc. Natl. Acad. Sci. USA 91(3):969-973.

Roguska, M.A. et al. (Oct. 1996). "A Comparison of Two Murine Monoclonal Antibodies Humanized By CDR-Grafting and Variable Domain Resurfacing," Protein Eng. 9(10):895-904.

Routier, F.H et al. (1997). "The Glycosylation Pattern of a Humanized IgGl Antibody (D1.3) Expressed in CHO Cells," Glycoconjugate Journal 14:201-207.

Roversi, P et al. (2000). "Modelling Prior Distributions of Atoms for Macro-Molecular Refinement and Completion," Acta Crystallogr D Biol Crystallogr D56:1316-1323.

Sadun, R.E. et al. (Jul. 1, 2007). "Immune Signatures of Murine and Human Cancers Reveal Unique Mechanisms of Tumor Escape and New Targets for Cancer Immunotherapy." Cancer Therapy: Preclinical 13(13):4016-4025.

Salceda, S. et al. (May 2005, e-pub. Mar. 9, 2005). "The Immunomodulatory Protein B7-H4 is Overexpressed in Breast and Ovarian Cancers and Promotes Epithelial Cell Transformation," Experimental Cell Research 306 (1):128-141.

Sambrook, J. et al. (2001). "Molecular Cloning: A Laboratory Manual," 3rd edition, J.F. Sambrook and D.W. Russell, ed., Cold Spring Harbor Laboratory Press: Cold Spring Harbor, NY, 2:107 pages.

Sankin, A. et al. (Oct. 2018). "The Expanding Repertoire of Targets for Immune Checkpoint Inhibition in Bladder Cancer: What Lies Beneath the Tip of the Iceberg, PD-L1," Urologic Oncology 36(10):459-468, 19 pages.

Schalper, K. et al. (Jan. 15, 2017, e-pubs. Jul. 20, 2016). "Differential Expression and Significance of PD-L1, IDO-1, and B7-H4 in Human Lung Cancer," Clinical Cancer Research 23(2):370-378.

Seliger, B. et al. (Dec. 2008). "The Complex Role of B7 Molecules in Tumor Immunology," Trends Mol. Med. 14(12):550-559, 19 pages.

Shaffer, D. et al. (2015). "Dissecting the Tumor Micro-environment in Triple Negative Breast Cancer Identifies a Mutually Exclusive Expression Pattern of the Immune Co-inhibitory Molecules B7-H 4 and PD-L1," Journal for Immunotherapy of Cancer 3(2):O17, 1 page.

Sheehan, J. et al. (Feb. 6, 2015). "Phage and Yeast Display," Microbiol. Spectr. 3(1):AID-0028-2014, 17 pages.

Shen, L. et al. (Aug. 2017). "B7-H4 Is a Prognostic Biomarker for Poor Survival in Patients With Pancreatic Cancer," Human Pathology 66:79-85.

(56) References Cited

OTHER PUBLICATIONS

Shi, H. et al. (2014) "Serum B7-H4 Expression is a Significant Prognostic Indicator for Patients With Gastric Cancer," World Journal of Surgical Oncology, 12:188, 5 pages.

Shields, R.L. et al. (Jul. 26, 2002, e-pub. May 1, 2002). "Lack of Fucose on Human IgG1 N-Linked Oligosaccharide Improves Binding to Human FcγRIII and Antibody-dependent Cellular Toxicity," J. Biol. Chem. 277:26733-26740.

Shields, R.L. et al. (Mar. 2, 2001). "High Resolution Mapping of the Binding Site on Human IgG1 for FcγRI, FcγII. FcγIII, and FcRn and Design of IgG1 Variants With Improved Binding to the FcγR," J. Biol. Chem. 276(9):6591-6604.

Shinkawa, T. et al. (Jan. 31, 2003). "The Absence of Fucose But Not The Presence of Galactose or Bisecting N-Acetylglucosamine of Human IgG1 Complex-Type Oligosaccharides Shows the Critical Role of Enhancing Antibody-Dependent Cellular Cytotoxicity," Journal of Biological Chemistry 278(5):3466-3473.

Shrestha, R. et al. (Jul. 13, 2018), "Monitoring Immune Checkpoint Regulators as Predictive Biomarkers in Hepatocellular Carcinoma," Frontiers in Oncology 8(269):1-17.

Sica, G. et al. (Jun. 2003). "B7-H4, a Molecule of the B7 Family, Negatively Regulates T Cell Immunity," Immunity 18 (6):849-861.

Siegel, R.W. et al. (2004). "High Efficiency Recovery and Epitope-Specific Sorting of an scFv Yeast Display Library." J Immunol Methods 286(1-2):141-153.

Simon, I. et al. (Aug. 2007, e-pub. May 11, 2007). "B7-H4 is Over-expressed in Early-stage Ovarian Cancer and is Independent of CA125 Expression," Gynecologic Oncology 106(2):334-341.

Simon, I. et al. (Feb. 1, 2006). "B7-H4 Is a Novel Membrane-bound Protein and a Candidate Serum and Tissue Biomarker for Ovarian Cancer," Cancer Research, 66(3):1570-1575.

Simon, I. et al. (May 2005). "Evaluation of B7-H4 (DD-O110) as a Prognostic Marker in Tissue and Serum of Ovarian Cancer Patients," Cancer Research, Abstract 4882, retrieved from https://cancerres.aacrjournals.org/content/65/9_Supplement/1153.2, last visited Apr. 30, 2020, 4 pages.

Smith, J. et al. (Jul. 2014). "B7-H4 as a Potential Target for Immunotherapy for Gynecologic Cancers: A Closer Look," Gynecologic Oncology 134(1):181-189, 20 pages.

Smith, J. et al. (Nov. 2016, e-pub. Oct. 4, 2016). "Tumor Regression and Delayed Onset Toxicity Following B7-H4 Car T Cell Therapy," Molecular Therapy 24(11): 1987-1999.

Smith, P. et al. (Apr. 17, 2012, e-pub. Apr. 2, 2012). "Mouse Model Recapitulating Human Fcγ Receptor Structural and Functional Diversity," PNAS 109(16):6181-6186, 6 pages.

Song, X. et al. (Apr. 5, 2016). "Prognostic Role of High B7-H4 Expression in Patients With Solid Tumors: A Meta-Analysis," Oncotarget 7(47):76523-76533.

Sood, A.K. (2010, e-pub. Sep. 10, 2009). "PDEF and PDEF-Induced Proteins as Candidate Tumor Antigens for T Cell and Antibody-Mediated Immunotherapy of Breast Cancer," Immunol. Res. 46:206-215.

Sun, Y. et al. (Aug. 2006). "B7-H3 and B7-H4 Expression in Non-small-cell Lung Cancer," Lung Cancer 53 (2):143-151.

Tan, Z. et al. (Feb. 23, 2017). "Prognostic Role of B7-H4 in Patients With Non-Small Cell Lung Cancer: A Meta-Analysis," Oncotarget 8(16):27137-27144.

Terrett, J. et al. (May 2008). "Preclinical Development of Anti B7-H4 Therapeutic Antibodies," Cancer Research, Abstract 4986, retrieved from https://canerres.acorjournals.org/content/68/9_Supplement/4986, last visited Apr. 30, 2020, 3 pages.

Thompson, R. et al. (Aug. 1, 2008). "Serum-Soluble B7x Is Elevated in Renal Cell Carcinoma Patients and is Associated With Advanced Stage," Cancer Research 68(15):6054-6058.

Thompson, R.H. et al. (2005). "B7-H1, Glycoprotein Blockade: A Novel Strategy to Enhance Immunotherapy in Patients With Renal Cell Carcinoma," Urology 66(Suppl. 5A):10-14.

Tramontano, A et al. (Sep. 1990). "Framework Residue 71 is a Major Determinant of the Position and Conformation of the Second Hypervariable Region in the VH Domains of Immunoglobulins," J Mol Biol 215 (1): 175-182.

Tringler, B. et al. (Jan. 2006, e-pub. Oct. 26, 2005). "B7-H4 Overexpression in Ovarian Tumors," Gynecologic Oncology 100(1):44-52.

Tringler, B. et al. (Mar. 1, 2005). "B7-H4 is Highly Expressed in Ductal and Lobular Breast Cancer," Clinical Cancer Research 11(5):1842-1848.

Umaña, P et al. (Feb. 1999). "Engineered Glycoforms of an Antineuro-Blastoma IgG 1 With Optimized Antibody-Dependent Cellular Cytotoxic Activity," Nat. Biotechnol. 17:176-180.

Van Regenmortel, M.H.V. (Jan. 12, 2018). "Development of a Preventive HIV Vaccine Requires Solving Inverse Problems Which is Unattainable by Rational Vaccine Design," Front. Immunol. 8(2009):1-11.

Verhoeyen, M. et al. (Mar. 25, 1988). "Reshaping Human Antibodies: Grafting An Antilysozyme Activity, " Science 239(4857):1534-1536.

Von Horsten, H.H. et al. (2010, e-pub. Jul. 15, 2010). "Production of Non-Fucosylated Antibodies by Co-expression of Heterologous GDP-6-Deoxy-D-Lyxo-4-Hexulose Reductase," Glycobiology 20(12):1607-1618.

Wagener, C et al. (Mar. 30, 1984). "Use of Biotin-Labeled Monoclonal Antibodies and Avidin-Peroxidase Conjugates for the Determination of Epitope Specificities in a Solid-Phase Competitive Enzyme Immunoassay," J Immunol Methods 68(1-2):269-274.

Wagener, C. et al. (May 1983). "Monoclonal Antibodies for Carcinoembryonic Antigen and Related Antigens as a Model System: a Systematic Approach for the Determination of Epitope Specificities of Monoclonal Antibodies," J Immunol 130(5):2308-2315.

Wang, L. et al. (2016, e-pub. Jun. 1, 2016). "Could B7-H4 Serve as a Target to Activate Anti-Cancer Immunity?" International Immunopharmacology 38:97-103.

Wang, L. et al. (Jul. 2018), "B7-H4 Overexpression Contributes to Poor Prognosis and Drug-Resistance in Triple-Negative Breast Cancer," Cancer Cell International 18:100, 12 pages.

Wang, L. et al. (Sep. 2015, e-pub. Sep. 28, 2015). "Roles of Coinhibitory Molecules B7-H3 and B7-H4 in Esophageal Squamous Cell Carcinoma," Tumour Biology pp. 1-11.

Wilcox, R.A. et al. (2009). "CD14+ hla-DR-/Lo Myeloid-Derived Suppressor Cells Express Immunosuppressive B7-H Family Members and Are Depleted Following Taxane-Based Chemotherapy in Melanoma," Blood 114(22):464, Abstract 464, retrieved from https://ashpublication.org/blood/article/114/22/464/64311/CD14-hlaDRlo-MyeloidDerived-Suppressor-Cell, last visited Apr. 30, 2020, 6 pages.

Wu, T.C. et al. (No Date). "Abstract 547: Development of Antigen-Targeted Vaccines and Immune Checkpoint Inhibitors for Cancer Therapy," Immune Response Modifiers: Cancer Vaccines, 1 page.

Xu, H. et al. (Mar. 2016, e-pub. Jan. 19, 2016). "B7-H3 and B7-H4 Are Independent Predictors of a Poor Prognosis in Patients With Pancreatic Cancer," Oncology Letters 11(3): 1841-1846, 10 pages.

Xu, Y. et al. (2013, e-pub. Sep. 17, 2013). "Addressing Polyspecificity of Antibodies Selected From an in Vitro Yeast Presentation System: A FACS-Based, High-Throughput Selection and Analytical Tool," PEDS (26) 10:663-670.

Yamane-Ohnuki, N. et al. (2004, e-pub. Aug. 6, 2004). "Establishment of FUT8 Knockout Chinese hamster Ovary Cells: An Ideal Host Cell Line for Producing Completely Defucosylated Antibodies With Enhances Antibody-Dependent Cellular Cytotoxicity," Biotech. Bloeng. 87:614-622.

Ye, Y. et al. (Aug. 2018). "Does B7-H4 Expression Correlate With Clinicopathologic Characteristics and Survival in Ovarian Cancer ?: A Systematic Review and Prisma-compliant Meta-analysis," Medicine 97(32):e11821, 8 pages.

Zang, X. et al. (Dec. 4, 2007). "B7-H3 and B7x Are Highly Expressed in Human Prostate Cancer and Associated With Disease Spread and Poor Outcome," Proc. Nat. Acad. Sci. USA 104(49): 19458-19463.

(56) References Cited

OTHER PUBLICATIONS

Zang, X. et al. (Sep. 2, 2003). "B7x: a Widely Expressed B7 Family Member That Inhibits T Cell Activation," Proc. Nat. Acad. Sci. USA 100(18):10388-10392.

Zhang, L. et al. (Nov. 2013, e-pub. Jan. 14, 2013). "The Costimulatory Molecule B7-H4 Promote Tumor Progression and Cell Proliferation Through Translocating Into Nucleus," Oncogene 32(46):5347-5358.

Zhang, N. et al. (Aug. 2014). "Preparation and Characterization of Monocional Antibody Against Human B7-H4 Molecule," Monoclonal Antibodies in Immunodiagnosis and Immunotherapy 33(4):270-274.

Zhang, S. et al. (Oct. 2015). "Circulating B7-H4 in Serum Predicts Prognosis in Patients With Hepatocellular Carcinoma," Genetics and Molecular Research 14(4):13041-13048.

Zhang, X. et al. (Jan. 3, 2017). "B7-H4 Promotes Tumor Growth and Metastatic Progression in Lung Cancer by Impacting Cell Proliferation and Survival," Oncotarget 8(12):18861-18871.

Zhou, D. et al. (Apr. 2018, e-pub. Feb. 13, 2018). "Silencing of B7-H4 Suppresses the Tumorigenicity of the Mgc-803 Human Gastric Cancer Cell Line and Promotes Cell Apoptosis via the Mitochondrial Signaling Pathway." International Journal of Oncology 52(4):1267-1276, 12 pages.

Zhou, T. et al. (Jun. 4, 2015), "Structural Repertoire of HIV-1-Neutralizing Antibodies Targeting the CD4 Supersite in 14 Donors," Cell 161:1280-1292, 46 pages.

Zhu, J. et al. (May 2013). "B7-H4 Expression is Associated With Cancer Progression and Predicts Patient Survival in Human Thyroid Cancer," Asian Pacific Journal of Cancer Prevention 14(5):3011-3015.

Zou, W. (Apr. 2005, e-pub. Mar. 18, 2015). "Immunosuppressive Networks in The Tumour Environment and Their Therapeutic Relevance," Nature Reviews 5:263-274.

Caldas et al. Humanization of the anti-CD18 antibody 6.7: an unexpected effect of a framework residue in binding to antigen, Mol. Immunol., 39(15):941-952 (2003).

Casadevall et al., Immunoglobulin isotype influences affinity and specificity, Proceedings of the National Academy of Sciences, 109(31): 12272-12273 (2012).

Daugherty et al., "CHAPTER 8: Formulation and delivery issues for monoclonal antibody therapeutics", Curr. Tren. In Mon. Ant. Dev. Man., 103-129 (2010).

Du et al., Molecular Basis of Recognition of Human Osteopontin by 23C3, a Potential Therapeutic Antibody for Treatment of Rheumatoid Arthritis, Journal of Molecular Biology, 382(4):835-842 (2008).

Kaplan et al., FPA 150, a novel B7-H4 therapeutic antibody with checkpoint blockade and ADCC activities, ESMO 2017 congress, Madrid, Spain; Poster, 1 (2017).

Khan et al., Cross-neutralizing anti-HIV-1 human single chain variable fragments(scFvs) against CD4 binding site and N332 glycan identified from a recombinant phage library, Sci. Rep., 7:45163 (2017).

Kunik et al., Structural Consensus among Antibodies Defines the Antigen Binding Site, PLOS Computational Biology, 8(2):e 1002388(2012).

Lee et al., Molecular-level analysis of the serum antibody repertoire in young adults before and after seasonal influenza vaccination, Nature Medicine, 22:1456-1464 (2016).

Wang et al., Antibody Structure, Instability, and Formulation, Journal of Pharmaceutical Sciences, 96(1):1-26 (2007).

Abadi, Y.M. et al. (Mar. 2013). "Host B7x Promotes Pulmonary Metastasis of Breast Cancer," Journal of Immunology 190(7):3806-3814.

Abdiche, Y.N. et al. (2016, e-pub. Feb. 8, 2016). "Assessing Kinetic and Epitopic Diversity Across Orthogonal Monoclonal Antibody Generation Platforms," mAbs 8(2):264-277.

Abdiche, Y.N. et al. (Mar. 15, 2009, e-pub. Dec. 7, 2008). "Exploring Blocking Assays Using Octet, ProteOn, and Biacore Biosensors," Analytical Biochem 386(2):172-180.

Al-Lazikani, B. et al. (1997). "Standard Conformations for the Canonical Structures of Immunoglobulins," J. Mol. Biol. 273:927-948.

Ames, R.S. et al. (Aug. 18, 1995). "Conversion of Murine Fabs Isolated From a Combinatorial Phage Display Library to Full Length Immunoglobulins," J. Immunol. Methods 184(2):177-186.

\* cited by examiner

H score (J516)=101

SEQUENCE LISTING

<160> NUMBER OF SEQ ID NOS: 98

<210> SEQ ID NO 1
<211> LENGTH: 282
<212> TYPE: PRT
<213> ORGANISM: Artificial Sequence
<220> FEATURE:
<223> OTHER INFORMATION: Human B7-H4

<400> SEQUENCE: 1

Met Ala Ser Leu Gly Gln Ile Leu Phe Trp Ser Ile Ile Ser Ile Ile
1               5                   10                  15

Ile Ile Leu Ala Gly Ala Ile Ala Leu Ile Ile Gly Phe Gly Ile Ser
                20                  25                  30

Gly Arg His Ser Ile Thr Val Thr Thr Val Ala Ser Ala Gly Asn Ile
            35                  40                  45

Gly Glu Asp Gly Ile Leu Ser Cys Thr Phe Glu Pro Asp Ile Lys Leu
        50                  55                  60

Ser Asp Ile Val Ile Gln Trp Leu Lys Glu Gly Val Leu Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
    130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

```
Glu Val Ser Asn Thr Ser Phe Glu Leu Asn Ser Glu Asn Val Thr Met
            195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser His Leu Gln Leu Leu Asn Ser
                245                 250                 255

Lys Ala Ser Leu Cys Val Ser Ser Phe Phe Ala Ile Ser Trp Ala Leu
                260                 265                 270

Leu Pro Leu Ser Pro Tyr Leu Met Leu Lys
            275                 280
```

```
<210> SEQ ID NO 2
<211> LENGTH: 57
<212> TYPE: DNA
<213> ORGANISM: Artificial Sequence
<220> FEATURE:
<223> OTHER INFORMATION: VH signal peptide

<400> SEQUENCE: 2
atgggcaggc ttacttcttc attcctgcta ctgattgtcc ctgcatatgt cctgtcc      57
```

```
<210> SEQ ID NO 3
<211> LENGTH: 57
<212> TYPE: DNA
<213> ORGANISM: Artificial Sequence
<220> FEATURE:
<223> OTHER INFORMATION: VL signal peptide

<400> SEQUENCE: 3
atgaagttgc ctgttaggct gttggtgctg atgttctgga ttcctgcttc cggcagt      57
```

```
<210> SEQ ID NO 4
<211> LENGTH: 19
<212> TYPE: PRT
<213> ORGANISM: Artificial Sequence
<220> FEATURE:
<223> OTHER INFORMATION: VH signal peptide

<400> SEQUENCE: 4

Met Gly Arg Leu Thr Ser Ser Phe Leu Leu Leu Ile Val Pro Ala Tyr
1               5                   10                  15

Val Leu Ser
```

```
<210> SEQ ID NO 5
<211> LENGTH: 19
<212> TYPE: PRT
<213> ORGANISM: Artificial Sequence
<220> FEATURE:
<223> OTHER INFORMATION: VL signal peptide

<400> SEQUENCE: 5

Met Lys Leu Pro Val Arg Leu Leu Val Leu Met Phe Trp Ile Pro Ala
1               5                   10                  15

Ser Gly Ser
```

```
<210> SEQ ID NO 6
<211> LENGTH: 120
<212> TYPE: PRT
<213> ORGANISM: Artificial Sequence
<220> FEATURE:
<223> OTHER INFORMATION: M6 VH
```

<400> SEQUENCE: 6

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Tyr
            20                  25                  30

Gly Leu Gly Val Gly Trp Ile Arg Gln Pro Ser Gly Lys Gly Leu Asp
        35                  40                  45

Trp Leu Ala Asn Ile Trp Trp Asn Asp Asp Lys Tyr Tyr Asn Ser Ala
    50                  55                  60

Leu Lys Ser Arg Leu Thr Ile Ser Lys Asp Thr Ser Asn Asn Gln Val
65                  70                  75                  80

Phe Leu Lys Ile Ser Ser Val Asp Thr Ala Asp Thr Gly Thr Tyr Tyr
                85                  90                  95

Cys Ala Gln Val Asp Gly Tyr Tyr Trp Tyr Phe Asp Val Trp Gly Ala
            100                 105                 110

Gly Thr Thr Val Thr Val Ser Ser
        115                 120

<210> SEQ ID NO 7
<211> LENGTH: 120
<212> TYPE: PRT
<213> ORGANISM: Artificial Sequence
<220> FEATURE:
<223> OTHER INFORMATION: M11 VH

<400> SEQUENCE: 7

Gln Val Thr Leu Lys Glu Ser Gly Pro Gly Ile Leu Gln Pro Ser Gln
1               5                   10                  15

Thr Leu Ser Leu Thr Cys Ser Leu Ser Gly Phe Ser Leu Ser Thr Tyr
            20                  25                  30

Gly Leu Gly Val Gly Trp Ile Arg Gln Pro Ser Gly Lys Gly Leu Gly
        35                  40                  45

Trp Leu Ala Asn Ile Trp Trp Asn Asp Asp Lys Tyr Tyr Asn Ser Ala
    50                  55                  60

Leu Lys Ser Arg Leu Thr Ile Ser Lys Asp Thr Ser Asn Asn Gln Val
65                  70                  75                  80

Phe Leu Lys Ile Ser Ser Val Asp Thr Ala Asp Thr Gly Thr Tyr Tyr
                85                  90                  95

Cys Ala Gln Val Asp Gly Tyr Tyr Trp Tyr Phe Asp Val Trp Gly Ala
            100                 105                 110

Gly Thr Thr Val Thr Val Ser Ser
        115                 120

<210> SEQ ID NO 8
<211> LENGTH: 120
<212> TYPE: PRT
<213> ORGANISM: Artificial Sequence
<220> FEATURE:
<223> OTHER INFORMATION: M15 VH

<400> SEQUENCE: 8

Gln Val Thr Leu Lys Glu Ser Gly Pro Gly Ile Leu Gln Ser Ser Gln
1               5                   10                  15

Thr Leu Ser Leu Thr Cys Ser Phe Ser Gly Phe Ser Leu Ser Thr Tyr
            20                  25                  30

Gly Leu Gly Val Gly Trp Ile Arg Gln Pro Ser Gly Lys Gly Leu Asp
        35                  40                  45

```
Trp Leu Ala Asn Ile Trp Trp Asn Asp Asp Lys Tyr Tyr Asn Ser Ala
 50                  55                  60

Leu Lys Ser Arg Leu Thr Ile Ser Lys Asp Thr Ser Asn Asn Gln Val
 65                  70                  75                  80

Phe Leu Lys Ile Ser Ser Val Asp Thr Ala Asp Thr Gly Thr Tyr Tyr
                 85                  90                  95

Cys Ala Gln Val Asp Gly Tyr Tyr Trp Tyr Phe Asp Val Trp Gly Ala
                100                 105                 110

Gly Thr Thr Val Thr Val Ser Ser
            115                 120

<210> SEQ ID NO 9
<211> LENGTH: 112
<212> TYPE: PRT
<213> ORGANISM: Artificial Sequence
<220> FEATURE:
<223> OTHER INFORMATION: M6, M11, M15 VL

<400> SEQUENCE: 9

Asp Val Leu Met Thr Gln Thr Pro Leu Ser Leu Pro Val Ser Leu Gly
 1               5                  10                  15

Asp Gln Ala Ser Ile Ser Cys Arg Ser Ser Gln Ser Ile Val His Ser
                 20                  25                  30

Asn Arg Asn Thr Tyr Leu Glu Trp Tyr Leu Gln Lys Pro Gly Gln Ser
             35                  40                  45

Pro Lys Leu Leu Ile Tyr Asn Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Val Pro Leu Thr Phe Gly Ala Gly Thr Lys Leu Glu Leu Lys
                100                 105                 110

<210> SEQ ID NO 10
<211> LENGTH: 112
<212> TYPE: PRT
<213> ORGANISM: Artificial Sequence
<220> FEATURE:
<223> OTHER INFORMATION: De-N-glycosylated VL

<400> SEQUENCE: 10

Asp Val Leu Met Thr Gln Thr Pro Leu Ser Leu Pro Val Ser Leu Gly
 1               5                  10                  15

Asp Gln Ala Ser Ile Ser Cys Arg Ser Ser Gln Ser Ile Val His Ser
                 20                  25                  30

Asn Arg Asn Thr Tyr Leu Glu Trp Tyr Leu Gln Lys Pro Gly Gln Ser
             35                  40                  45

Pro Lys Leu Leu Ile Tyr Asn Val Ala Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Val Pro Leu Thr Phe Gly Ala Gly Thr Lys Leu Glu Leu Lys
                100                 105                 110
```

<210> SEQ ID NO 11
<211> LENGTH: 112
<212> TYPE: PRT
<213> ORGANISM: Artificial Sequence
<220> FEATURE:
<223> OTHER INFORMATION: De-N-glycosylated VL

<400> SEQUENCE: 11

```
Asp Val Leu Met Thr Gln Thr Pro Leu Ser Leu Pro Val Ser Leu Gly
1               5                   10                  15

Asp Gln Ala Ser Ile Ser Cys Arg Ser Gln Ser Ile Val His Ser
            20                  25                  30

Asn Arg Asn Thr Tyr Leu Glu Trp Tyr Leu Gln Lys Pro Gly Gln Ser
        35                  40                  45

Pro Lys Leu Leu Ile Tyr Gln Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Ala Gly Thr Lys Leu Glu Leu Lys
            100                 105                 110
```

<210> SEQ ID NO 12
<211> LENGTH: 1395
<212> TYPE: DNA
<213> ORGANISM: Artificial Sequence
<220> FEATURE:
<223> OTHER INFORMATION: antibody J512, J517, J518 Heavy chain

<400> SEQUENCE: 12

```
atgggcaggc ttacttcttc attcctgcta ctgattgtcc ctgcatatgt cctgtcccag     60
gtcactctga aagagtctgg ccctgggata ttgcagccct cccagaccct cagtctgact    120
tgttctttct ctgggttttc actgagcact tatggtctgg gtgtaggttg gattcgtcag    180
ccttcaggga agggtctgga ctggctggcc acatttggt ggaatgatga taaatactat    240
aactcagccc tgaagagccg gctcacaatc tccaaggata cctccaacaa ccaggtattc    300
ctcaagatct ccagtgtgga cactgcagat actggcacat actactgtgc tcaagttgat    360
ggttactact ggtacttcga tgtctggggc cagggaccac ggtcaccgt ctcctcagcc    420
aaaacgacac caccaagtgt ctatccactg gccctggat ctgctgccca aactaactcc    480
atggtgaccc tgggatgcct ggtcaagggc tatttcctg agccagtgac agtgacctgg    540
aactctggat ccctgtccag cggtgtgcac accttccag ctgtcctgga gtctgacctc    600
tacactctga gcagctcagt gactgtcccc tccagcccctc ggcccagcga accgtcacc    660
tgcaacgttg cccacccggc cagcagcacc aaagtggaca gaaaattgt gcccagggat    720
tgtggttgta agccttgcat atgtacagtc cagaagtat catctgtctt catcttcccc    780
ccaaagatca aggatgtact catgatctcc ctgagcccca agtcacatg tgtggtggtg    840
gatgtgagcg aggatgaccc agatgtccag atcagctggt ttgtgaacaa cgtggaagta    900
cacacagctc agacacaaac ccatagagag gattacaaca gtactctccg ggtggtcagt    960
gccctcccca tccagcacca ggactggatg agtggcaagg agttcaaatg caaggtcaac    1020
aacaaagacc tcccagcgcc catcgagaga accatctcaa aacccaaagg gtcagtaaga    1080
gctccacagg tatatgtctt gcctccacca gaagaagaga tgactaagaa acaggtcact    1140
ctgacctgca tggtcacaga cttcatgcct gaagacattt acgtggagtg gaccaacaac    1200
```

| | |
|---|---|
| gggaaaacag agctaaacta caagaacact gaaccagtcc tggactctga tggttcttac | 1260 |
| ttcatgtaca gcaagctgag agtggaaaag aagaactggg tggaaagaaa tagctactcc | 1320 |
| tgttcagtgg tccacgaggg tctgcacaat caccacacga ctaagagctt ctcccggact | 1380 |
| ccgggtaaat agtaa | 1395 |

```
<210> SEQ ID NO 13
<211> LENGTH: 1395
<212> TYPE: DNA
<213> ORGANISM: Artificial Sequence
<220> FEATURE:
<223> OTHER INFORMATION: antibody J514, J519, J520 Heavy chain

<400> SEQUENCE: 13
```

| | |
|---|---|
| atgggcaggc ttacttcttc attcctgcta ctgattgtcc ctgcatatgt cctgtcccag | 60 |
| gtcactctga aagagtctgg ccctgggata ttgcagccct cccagaccct cagtctgact | 120 |
| tgttctctct ctgggttttc actgagcact tatggtctgg gtgtaggttg gattcgtcag | 180 |
| ccttcaggga agggtctggg ctggctggcc aacatttggt ggaatgatga taaatactat | 240 |
| aactcagccc tgaagagccg gctcacaatc tccaaggata cctccaacaa ccaggtattc | 300 |
| ctcaagatct ccagtgtgga cactgcagat actggcacat actactgtgc tcaagttgat | 360 |
| ggttactact ggtacttcga tgtctggggc cagggacca cggtcaccgt ctcctcagcc | 420 |
| aaaacgacac caccaagtgt ctatccactg gcccctggat ctgctgccca aactaactcc | 480 |
| atggtgaccc tgggatgcct ggtcaagggc tatttccctg agccagtgac agtgacctgg | 540 |
| aactctggat ccctgtccag cggtgtgcac accttcccag ctgtcctgga gtctgacctc | 600 |
| tacactctga gcagctcagt gactgtcccc tccagccctc ggcccagcga gaccgtcacc | 660 |
| tgcaacgttg cccacccggc cagcagcacc aaggtggaca agaaaattgt gcccagggat | 720 |
| tgtggttgta agccttgcat atgtacagtc ccagaagtat catctgtctt catcttcccc | 780 |
| ccaaagatca aggatgtact catgatctcc ctgagcccca tagtcacatg tgtggtggtg | 840 |
| gatgtgagcg aggatgaccc agatgtccag atcagctggt ttgtaacaa cgtggaagta | 900 |
| cacacagctc agacacaaac ccatagagag gattacaaca gtactctccg ggtggtcagt | 960 |
| gccctcccca tccagcacca ggactggatg agtggcaagg agttcaaatg caaggtcaac | 1020 |
| aacaaagacc tcccagcgcc catcgagaga accatctcaa acccaaagg gtcagtaaga | 1080 |
| gctccacagg tatatgtctt gcctccacca gaagaagaga tgactaagaa acaggtcact | 1140 |
| ctgacctgca tggtcacaga cttcatgcct gaagacattt acgtggagtg gaccaacaac | 1200 |
| gggaaaacag agctaaacta caagaacact gaaccagtcc tggactctga tggttcttac | 1260 |
| ttcatgtaca gcaagctgag agtggaaaag aagaactggg tggaaagaaa tagctactcc | 1320 |
| tgttcagtgg tccacgaggg tctgcacaat caccacacga ctaagagctt ctcccggact | 1380 |
| ccgggtaaat agtaa | 1395 |

```
<210> SEQ ID NO 14
<211> LENGTH: 1395
<212> TYPE: DNA
<213> ORGANISM: Artificial Sequence
<220> FEATURE:
<223> OTHER INFORMATION: antibody J516, J521, J522 Heavy chain

<400> SEQUENCE: 14
```

| | |
|---|---|
| atgggcaggc ttacttcttc attcctgcta ctgattgtcc ctgcatatgt cctgtcccag | 60 |

| | |
|---|---|
| gtcactctga aagagtctgg ccctgggata ttgcagtcct cccagaccct cagtctgact | 120 |
| tgttctttct ctgggttttc actgagcact tatggtctgg gtgtaggttg gattcgtcag | 180 |
| ccttcaggga agggtctgga ctggctggcc aacatttggt ggaatgatga taaatactat | 240 |
| aactcagccc tgaagagccg gctcacaatc tccaaggata cctccaacaa ccaggtattc | 300 |
| ctcaagatct ccagtgtgga cactgcagat actggcacat actactgtgc tcaagttgat | 360 |
| ggttactact ggtacttcga tgtctggggc cagggaccac ggtcaccgtc tcctcagcc | 420 |
| aaaacgacac caccaagtgt ctatccactg gcccctggat ctgctgccca aactaactcc | 480 |
| atggtgaccc tgggatgcct ggtcaagggc tatttccctg agccagtgac agtgacctgg | 540 |
| aactctggat ccctgtccag cggtgtgcac accttcccag ctgtcctgga gtctgacctc | 600 |
| tacactctga gcagctcagt gactgtcccc tccagccctc ggcccagcga gaccgtcacc | 660 |
| tgcaacgttg cccacccggc cagcagcacc aaggtggaca gaaaaattgt gcccagggat | 720 |
| tgtggttgta agccttgcat atgtacagtc ccagaagtat catctgtctt catcttcccc | 780 |
| ccaaagatca aggatgtact catgatctcc ctgagcccca tagtcacatg tgtggtggtg | 840 |
| gatgtgagcg aggatgaccc agatgtccag atcagctggt ttgtgaacaa cgtggaagta | 900 |
| cacacagctc agacacaaac ccatagagag gattacaaca gtactctccg ggtggtcagt | 960 |
| gccctcccca tccagcacca ggactggatg agtggcaagg agttcaaatg caaggtcaac | 1020 |
| aacaaagacc tcccagcgcc catcgagaga accatctcaa acccaaaggg tcagtaaga | 1080 |
| gctccacagg tatatgtctt gcctccacca gaagaagaga tgactaagaa acaggtcact | 1140 |
| ctgacctgca tggtcacaga cttcatgcct gaagacattt acgtggagtg gaccaacaac | 1200 |
| gggaaaacag agctaaacta caagaacact gaaccagtcc tggactctga tggttcttac | 1260 |
| ttcatgtaca gcaagctgag agtggaaaag aagaactggg tggaaagaaa tagctactcc | 1320 |
| tgttcagtgg tccacgaggg tctgcacaat caccacacga ctaagagctt ctcccggact | 1380 |
| ccgggtaaat agtaa | 1395 |

<210> SEQ ID NO 15
<211> LENGTH: 717
<212> TYPE: DNA
<213> ORGANISM: Artificial Sequence
<220> FEATURE:
<223> OTHER INFORMATION: antibody J511 to J516 Light chain

<400> SEQUENCE: 15

| | |
|---|---|
| atgaagttgc ctgttaggct gttggtgctg atgttctgga ttcctgcttc cggcagtgat | 60 |
| gttttgatga cccaaactcc actctccctg cctgtcagtc ttggagatca agcctccatc | 120 |
| tcttgcagat ctagtcagag cattgtacat agtaatagaa cacctatttt agaatggtac | 180 |
| ctgcagaaac caggccagtc tccaaagctc ctgatctaca cgtttccaa ccgatttct | 240 |
| ggggtcccag acaggttcag tggcagtgga tcaggacaga atttcacact caagatcagc | 300 |
| agagtggagg ctgaggatct gggagtttat tactgctttc aaggttcaca tgttccgctc | 360 |
| acgttcggtg ctgggaccaa gctggagctg aaacgggctg atgctgcacc aactgtatcc | 420 |
| atcttcccac catccagtga gcagttgaca tctggaggtg cctcagtcgt gtgcttcttg | 480 |
| aacaacttct accccaaaga catcaatgtc aagtggaaga ttgatggcag tgaacgacaa | 540 |
| aatggcgtcc tgaacagttg gactgatcag gacagcaaag acagcaccta cagcatgagc | 600 |
| agcaccctca cgttgaccaa ggacgagtat gaacgacata acagctatac ctgtgaggcc | 660 |
| actcacaaga catcaacttc acccattgtc aagagcttca caggaatga gtgttag | 717 |

<210> SEQ ID NO 16
<211> LENGTH: 444
<212> TYPE: PRT
<213> ORGANISM: Artificial Sequence
<220> FEATURE:
<223> OTHER INFORMATION: M6 H (J512, J517, J518) Heavy Chain

<400> SEQUENCE: 16

```
Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Tyr
            20                  25                  30

Gly Leu Gly Val Gly Trp Ile Arg Gln Pro Ser Gly Lys Gly Leu Asp
        35                  40                  45

Trp Leu Ala Asn Ile Trp Trp Asn Asp Asp Lys Tyr Tyr Asn Ser Ala
    50                  55                  60

Leu Lys Ser Arg Leu Thr Ile Ser Lys Asp Thr Ser Asn Asn Gln Val
65                  70                  75                  80

Phe Leu Lys Ile Ser Ser Val Asp Thr Ala Asp Thr Gly Thr Tyr Tyr
                85                  90                  95

Cys Ala Gln Val Asp Gly Tyr Tyr Trp Tyr Phe Asp Val Trp Gly Ala
            100                 105                 110

Gly Thr Thr Val Thr Val Ser Ser Ala Lys Thr Thr Pro Pro Ser Val
        115                 120                 125

Tyr Pro Leu Ala Pro Gly Ser Ala Ala Gln Thr Asn Ser Met Val Thr
    130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Glu Ser Asp Leu Tyr Thr Leu Ser Ser Ser Val Thr Val Pro Ser
            180                 185                 190

Ser Pro Arg Pro Ser Glu Thr Val Thr Cys Asn Val Ala His Pro Ala
        195                 200                 205

Ser Ser Thr Lys Val Asp Lys Lys Ile Val Pro Arg Asp Cys Gly Cys
    210                 215                 220

Lys Pro Cys Ile Cys Thr Val Pro Glu Val Ser Ser Val Phe Ile Phe
225                 230                 235                 240

Pro Pro Lys Ile Lys Asp Val Leu Met Ile Ser Leu Ser Pro Ile Val
                245                 250                 255

Thr Cys Val Val Val Asp Val Ser Glu Asp Asp Pro Asp Val Gln Ile
            260                 265                 270

Ser Trp Phe Val Asn Asn Val Glu Val His Thr Ala Gln Thr Gln Thr
        275                 280                 285

His Arg Glu Asp Tyr Asn Ser Thr Leu Arg Val Val Ser Ala Leu Pro
    290                 295                 300

Ile Gln His Gln Asp Trp Met Ser Gly Lys Glu Phe Lys Cys Lys Val
305                 310                 315                 320

Asn Asn Lys Asp Leu Pro Ala Pro Ile Glu Arg Thr Ile Ser Lys Pro
                325                 330                 335

Lys Gly Ser Val Arg Ala Pro Gln Val Tyr Val Leu Pro Pro Pro Glu
            340                 345                 350

Glu Glu Met Thr Lys Lys Gln Val Thr Leu Thr Cys Met Val Thr Asp
        355                 360                 365
```

```
Phe Met Pro Glu Asp Ile Tyr Val Glu Trp Thr Asn Asn Gly Lys Thr
        370                 375                 380

Glu Leu Asn Tyr Lys Asn Thr Glu Pro Val Leu Asp Ser Asp Gly Ser
385                 390                 395                 400

Tyr Phe Met Tyr Ser Lys Leu Arg Val Glu Lys Lys Asn Trp Val Glu
            405                 410                 415

Arg Asn Ser Tyr Ser Cys Ser Val Val His Glu Gly Leu His Asn His
                420                 425                 430

His Thr Thr Lys Ser Phe Ser Arg Thr Pro Gly Lys
            435                 440
```

<210> SEQ ID NO 17
<211> LENGTH: 444
<212> TYPE: PRT
<213> ORGANISM: Artificial Sequence
<220> FEATURE:
<223> OTHER INFORMATION: M11 H (J514, J519, J520) Heavy Chain

<400> SEQUENCE: 17

```
Gln Val Thr Leu Lys Glu Ser Gly Pro Gly Ile Leu Gln Pro Ser Gln
1               5                   10                  15

Thr Leu Ser Leu Thr Cys Ser Leu Ser Gly Phe Ser Leu Ser Thr Tyr
            20                  25                  30

Gly Leu Gly Val Gly Trp Ile Arg Gln Pro Ser Gly Lys Gly Leu Gly
        35                  40                  45

Trp Leu Ala Asn Ile Trp Trp Asn Asp Asp Lys Tyr Tyr Asn Ser Ala
50                  55                  60

Leu Lys Ser Arg Leu Thr Ile Ser Lys Asp Thr Ser Asn Asn Gln Val
65                  70                  75                  80

Phe Leu Lys Ile Ser Ser Val Asp Thr Ala Asp Thr Gly Thr Tyr Tyr
                85                  90                  95

Cys Ala Gln Val Asp Gly Tyr Tyr Trp Tyr Phe Asp Val Trp Gly Ala
            100                 105                 110

Gly Thr Thr Val Thr Val Ser Ser Ala Lys Thr Thr Pro Pro Ser Val
        115                 120                 125

Tyr Pro Leu Ala Pro Gly Ser Ala Ala Gln Thr Asn Ser Met Val Thr
    130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Glu Ser Asp Leu Tyr Thr Leu Ser Ser Ser Val Thr Val Pro Ser
            180                 185                 190

Ser Pro Arg Pro Ser Glu Thr Val Thr Cys Asn Val Ala His Pro Ala
        195                 200                 205

Ser Ser Thr Lys Val Asp Lys Lys Ile Val Pro Arg Asp Cys Gly Cys
    210                 215                 220

Lys Pro Cys Ile Cys Thr Val Pro Glu Val Ser Ser Val Phe Ile Phe
225                 230                 235                 240

Pro Pro Lys Ile Lys Asp Val Leu Met Ile Ser Leu Ser Pro Ile Val
                245                 250                 255

Thr Cys Val Val Val Asp Val Ser Glu Asp Asp Pro Asp Val Gln Ile
            260                 265                 270

Ser Trp Phe Val Asn Asn Val Glu Val His Thr Ala Gln Thr Gln Thr
        275                 280                 285
```

-continued

```
His Arg Glu Asp Tyr Asn Ser Thr Leu Arg Val Val Ser Ala Leu Pro
        290                 295                 300

Ile Gln His Gln Asp Trp Met Ser Gly Lys Glu Phe Lys Cys Lys Val
305                 310                 315                 320

Asn Asn Lys Asp Leu Pro Ala Pro Ile Glu Arg Thr Ile Ser Lys Pro
                325                 330                 335

Lys Gly Ser Val Arg Ala Pro Gln Val Tyr Val Leu Pro Pro Pro Glu
                340                 345                 350

Glu Glu Met Thr Lys Lys Gln Val Thr Leu Thr Cys Met Val Thr Asp
                355                 360                 365

Phe Met Pro Glu Asp Ile Tyr Val Glu Trp Thr Asn Asn Gly Lys Thr
370                 375                 380

Glu Leu Asn Tyr Lys Asn Thr Glu Pro Val Leu Asp Ser Asp Gly Ser
385                 390                 395                 400

Tyr Phe Met Tyr Ser Lys Leu Arg Val Glu Lys Lys Asn Trp Val Glu
                405                 410                 415

Arg Asn Ser Tyr Ser Cys Ser Val Val His Glu Gly Leu His Asn His
                420                 425                 430

His Thr Thr Lys Ser Phe Ser Arg Thr Pro Gly Lys
                435                 440

<210> SEQ ID NO 18
<211> LENGTH: 444
<212> TYPE: PRT
<213> ORGANISM: Artificial Sequence
<220> FEATURE:
<223> OTHER INFORMATION: M15 H (J516, J521, J522) Heavy Chain

<400> SEQUENCE: 18

Gln Val Thr Leu Lys Glu Ser Gly Pro Gly Ile Leu Gln Ser Ser Gln
1               5                   10                  15

Thr Leu Ser Leu Thr Cys Ser Phe Ser Gly Phe Ser Leu Ser Thr Tyr
                20                  25                  30

Gly Leu Gly Val Gly Trp Ile Arg Gln Pro Ser Gly Lys Gly Leu Asp
            35                  40                  45

Trp Leu Ala Asn Ile Trp Trp Asn Asp Asp Lys Tyr Tyr Asn Ser Ala
50                  55                  60

Leu Lys Ser Arg Leu Thr Ile Ser Lys Asp Thr Ser Asn Asn Gln Val
65                  70                  75                  80

Phe Leu Lys Ile Ser Ser Val Asp Thr Ala Asp Thr Gly Thr Tyr Tyr
                85                  90                  95

Cys Ala Gln Val Asp Gly Tyr Tyr Trp Tyr Phe Asp Val Trp Gly Ala
                100                 105                 110

Gly Thr Thr Val Thr Val Ser Ser Ala Lys Thr Thr Pro Pro Ser Val
            115                 120                 125

Tyr Pro Leu Ala Pro Gly Ser Ala Ala Gln Thr Asn Ser Met Val Thr
            130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Glu Ser Asp Leu Tyr Thr Leu Ser Ser Val Thr Val Pro Ser
            180                 185                 190

Ser Pro Arg Pro Ser Glu Thr Val Thr Cys Asn Val Ala His Pro Ala
            195                 200                 205
```

```
Ser Ser Thr Lys Val Asp Lys Lys Ile Val Pro Arg Asp Cys Gly Cys
    210                 215                 220

Lys Pro Cys Ile Cys Thr Val Pro Glu Val Ser Ser Val Phe Ile Phe
225                 230                 235                 240

Pro Pro Lys Ile Lys Asp Val Leu Met Ile Ser Leu Ser Pro Ile Val
                245                 250                 255

Thr Cys Val Val Val Asp Val Ser Glu Asp Asp Pro Asp Val Gln Ile
            260                 265                 270

Ser Trp Phe Val Asn Asn Val Glu Val His Thr Ala Gln Thr Gln Thr
        275                 280                 285

His Arg Glu Asp Tyr Asn Ser Thr Leu Arg Val Val Ser Ala Leu Pro
    290                 295                 300

Ile Gln His Gln Asp Trp Met Ser Gly Lys Glu Phe Lys Cys Lys Val
305                 310                 315                 320

Asn Asn Lys Asp Leu Pro Ala Pro Ile Glu Arg Thr Ile Ser Lys Pro
                325                 330                 335

Lys Gly Ser Val Arg Ala Pro Gln Val Tyr Val Leu Pro Pro Pro Glu
            340                 345                 350

Glu Glu Met Thr Lys Lys Gln Val Thr Leu Thr Cys Met Val Thr Asp
        355                 360                 365

Phe Met Pro Glu Asp Ile Tyr Val Glu Trp Thr Asn Asn Gly Lys Thr
    370                 375                 380

Glu Leu Asn Tyr Lys Asn Thr Glu Pro Val Leu Asp Ser Asp Gly Ser
385                 390                 395                 400

Tyr Phe Met Tyr Ser Lys Leu Arg Val Glu Lys Lys Asn Trp Val Glu
                405                 410                 415

Arg Asn Ser Tyr Ser Cys Ser Val Val His Glu Gly Leu His Asn His
            420                 425                 430

His Thr Thr Lys Ser Phe Ser Arg Thr Pro Gly Lys
        435                 440

<210> SEQ ID NO 19
<211> LENGTH: 219
<212> TYPE: PRT
<213> ORGANISM: Artificial Sequence
<220> FEATURE:
<223> OTHER INFORMATION: M6, M11, M15 L (J5l1 to J5l6) Light Chain

<400> SEQUENCE: 19

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Arg Asn Thr Tyr Leu Glu Trp Tyr Leu Gln Lys Pro Gly Gln Ser
        35                  40                  45

Pro Lys Leu Leu Ile Tyr Asn Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Ala Gly Thr Lys Leu Glu Leu Lys
            100                 105                 110

Arg Ala Asp Ala Ala Pro Thr Val Ser Ile Phe Pro Pro Ser Ser Glu
        115                 120                 125
```

```
Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
                180                 185                 190

Arg His Asn Ser Tyr Thr Cys Glu Ala Thr His Lys Thr Ser Thr Ser
                195                 200                 205

Pro Ile Val Lys Ser Phe Asn Arg Asn Glu Cys
    210                 215

<210> SEQ ID NO 20
<211> LENGTH: 493
<212> TYPE: PRT
<213> ORGANISM: Artificial Sequence
<220> FEATURE:
<223> OTHER INFORMATION: B7H4 extra cellular domain (ECD) protein

<400> SEQUENCE: 20

Met Ala Ser Leu Gly Gln Ile Leu Phe Trp Ser Ile Ile Ser Ile Ile
1               5                   10                  15

Ile Ile Leu Ala Gly Ala Ile Ala Leu Ile Ile Gly Phe Gly Ile Ser
                20                  25                  30

Gly Arg His Ser Ile Thr Val Thr Thr Val Ala Ser Ala Gly Asn Ile
            35                  40                  45

Gly Glu Asp Gly Ile Leu Ser Cys Thr Phe Glu Pro Asp Ile Lys Leu
50                  55                  60

Ser Asp Ile Val Ile Gln Trp Leu Lys Glu Gly Val Leu Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
    130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
                180                 185                 190

Glu Val Ser Asn Thr Ser Phe Glu Leu Asn Ser Glu Asn Val Thr Met
                195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser His Leu Gln Leu Leu Asn Ser
                245                 250                 255

Lys Ala Ser Gly Ser Glu Pro Lys Ser Ser Asp Lys Thr His Thr Cys
                260                 265                 270
```

```
Pro Pro Cys Pro Ala Pro Glu Leu Leu Gly Gly Pro Ser Val Phe Leu
            275                 280                 285

Phe Pro Pro Lys Pro Lys Asp Thr Leu Met Ile Ser Arg Thr Pro Glu
    290                 295                 300

Val Thr Cys Val Val Val Asp Val Ser His Glu Asp Pro Glu Val Lys
305                 310                 315                 320

Phe Asn Trp Tyr Val Asp Gly Val Glu Val His Asn Ala Lys Thr Lys
                325                 330                 335

Pro Arg Glu Glu Gln Tyr Asn Ser Thr Tyr Arg Val Val Ser Val Leu
            340                 345                 350

Thr Val Leu His Gln Asp Trp Leu Asn Gly Lys Glu Tyr Lys Cys Lys
        355                 360                 365

Val Ser Asn Lys Ala Leu Pro Ala Pro Ile Glu Lys Thr Ile Ser Lys
370                 375                 380

Ala Lys Gly Gln Pro Arg Glu Pro Gln Val Tyr Thr Leu Pro Pro Ser
385                 390                 395                 400

Arg Asp Glu Leu Thr Lys Asn Gln Val Ser Leu Thr Cys Leu Val Lys
                405                 410                 415

Gly Phe Tyr Pro Ser Asp Ile Ala Val Glu Trp Glu Ser Asn Gly Gln
            420                 425                 430

Pro Glu Asn Asn Tyr Lys Thr Thr Pro Pro Val Leu Asp Ser Asp Gly
        435                 440                 445

Ser Phe Phe Leu Tyr Ser Lys Leu Thr Val Asp Lys Ser Arg Trp Gln
    450                 455                 460

Gln Gly Asn Val Phe Ser Cys Ser Val Met His Glu Ala Leu His Asn
465                 470                 475                 480

His Tyr Thr Gln Lys Ser Leu Ser Leu Ser Pro Gly Lys
                485                 490

<210> SEQ ID NO 21
<211> LENGTH: 385
<212> TYPE: PRT
<213> ORGANISM: Artificial Sequence
<220> FEATURE:
<223> OTHER INFORMATION: B7-H4 N-Terminal IgV-domain (amino acids
      1-151)-huIgG Fc fusion protein

<400> SEQUENCE: 21

Met Ala Ser Leu Gly Gln Ile Leu Phe Trp Ser Ile Ile Ser Ile Ile
1               5                   10                  15

Ile Ile Leu Ala Gly Ala Ile Ala Leu Ile Ile Gly Phe Gly Ile Ser
            20                  25                  30

Gly Arg His Ser Ile Thr Val Thr Thr Val Ala Ser Ala Gly Asn Ile
        35                  40                  45

Gly Glu Asp Gly Ile Leu Ser Cys Thr Phe Glu Pro Asp Ile Lys Leu
    50                  55                  60

Ser Asp Ile Val Ile Gln Trp Leu Lys Glu Gly Val Leu Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
```

```
                130                 135                 140
Tyr Lys Thr Gly Ala Phe Ser Gly Ser Glu Pro Lys Ser Ser Asp Lys
145                 150                 155                 160

Thr His Thr Cys Pro Pro Cys Pro Ala Pro Glu Leu Leu Gly Gly Pro
                165                 170                 175

Ser Val Phe Leu Phe Pro Pro Lys Pro Lys Asp Thr Leu Met Ile Ser
                180                 185                 190

Arg Thr Pro Glu Val Thr Cys Val Val Val Asp Val Ser His Glu Asp
                195                 200                 205

Pro Glu Val Lys Phe Asn Trp Tyr Val Asp Gly Val Glu Val His Asn
            210                 215                 220

Ala Lys Thr Lys Pro Arg Glu Glu Gln Tyr Asn Ser Thr Tyr Arg Val
225                 230                 235                 240

Val Ser Val Leu Thr Val Leu His Gln Asp Trp Leu Asn Gly Lys Glu
                245                 250                 255

Tyr Lys Cys Lys Val Ser Asn Lys Ala Leu Pro Ala Pro Ile Glu Lys
                260                 265                 270

Thr Ile Ser Lys Ala Lys Gly Gln Pro Arg Glu Pro Gln Val Tyr Thr
            275                 280                 285

Leu Pro Pro Ser Arg Asp Glu Leu Thr Lys Asn Gln Val Ser Leu Thr
290                 295                 300

Cys Leu Val Lys Gly Phe Tyr Pro Ser Asp Ile Ala Val Glu Trp Glu
305                 310                 315                 320

Ser Asn Gly Gln Pro Glu Asn Asn Tyr Lys Thr Thr Pro Pro Val Leu
                325                 330                 335

Asp Ser Asp Gly Ser Phe Phe Leu Tyr Ser Lys Leu Thr Val Asp Lys
                340                 345                 350

Ser Arg Trp Gln Gln Gly Asn Val Phe Ser Cys Ser Val Met His Glu
            355                 360                 365

Ala Leu His Asn His Tyr Thr Gln Lys Ser Leu Ser Leu Ser Pro Gly
        370                 375                 380

Lys
385

<210> SEQ ID NO 22
<211> LENGTH: 8
<212> TYPE: PRT
<213> ORGANISM: Artificial Sequence
<220> FEATURE:
<223> OTHER INFORMATION: VH-complementarity determining region 1

<400> SEQUENCE: 22

Gly Phe Ser Leu Ser Thr Tyr Gly
1               5

<210> SEQ ID NO 23
<211> LENGTH: 5
<212> TYPE: PRT
<213> ORGANISM: Artificial Sequence
<220> FEATURE:
<223> OTHER INFORMATION: VH-complementarity determining region 2

<400> SEQUENCE: 23

Trp Trp Asn Asp Asp
1               5

<210> SEQ ID NO 24
<211> LENGTH: 10
```

```
<212> TYPE: PRT
<213> ORGANISM: Artificial Sequence
<220> FEATURE:
<223> OTHER INFORMATION: VH-complementarity determining region 3

<400> SEQUENCE: 24

Val Asp Gly Tyr Tyr Trp Tyr Phe Asp Val
1               5                   10

<210> SEQ ID NO 25
<211> LENGTH: 16
<212> TYPE: PRT
<213> ORGANISM: Artificial Sequence
<220> FEATURE:
<223> OTHER INFORMATION: VL-complementarity determining region 1

<400> SEQUENCE: 25

Arg Ser Ser Gln Ser Ile Val His Ser Asn Arg Asn Thr Tyr Leu Glu
1               5                   10                  15

<210> SEQ ID NO 26
<211> LENGTH: 7
<212> TYPE: PRT
<213> ORGANISM: Artificial Sequence
<220> FEATURE:
<223> OTHER INFORMATION: VL-complementarity determining region 2

<400> SEQUENCE: 26

Asn Val Ser Asn Arg Phe Ser
1               5

<210> SEQ ID NO 27
<211> LENGTH: 7
<212> TYPE: PRT
<213> ORGANISM: Artificial Sequence
<220> FEATURE:
<223> OTHER INFORMATION: VL-CDR2, De-N-glycosylated (1)

<400> SEQUENCE: 27

Asn Val Ala Asn Arg Phe Ser
1               5

<210> SEQ ID NO 28
<211> LENGTH: 7
<212> TYPE: PRT
<213> ORGANISM: Artificial Sequence
<220> FEATURE:
<223> OTHER INFORMATION: VL-CDR2, De-N-glycosylated (2)

<400> SEQUENCE: 28

Gln Val Ser Asn Arg Phe Ser
1               5

<210> SEQ ID NO 29
<211> LENGTH: 9
<212> TYPE: PRT
<213> ORGANISM: Artificial Sequence
<220> FEATURE:
<223> OTHER INFORMATION: VL-complementarity determining region 3

<400> SEQUENCE: 29

Phe Gln Gly Ser His Val Pro Leu Thr
1               5

<210> SEQ ID NO 30
<211> LENGTH: 219
<212> TYPE: PRT
```

<213> ORGANISM: Artificial Sequence
<220> FEATURE:
<223> OTHER INFORMATION: De-N-glycosylated Light chain (1)

<400> SEQUENCE: 30

```
Asp Val Leu Met Thr Gln Thr Pro Leu Ser Leu Pro Val Ser Leu Gly
1               5                   10                  15
Asp Gln Ala Ser Ile Ser Cys Arg Ser Ser Gln Ser Ile Val His Ser
            20                  25                  30
Asn Arg Asn Thr Tyr Leu Glu Trp Tyr Leu Gln Lys Pro Gly Gln Ser
        35                  40                  45
Pro Lys Leu Leu Ile Tyr Asn Val Ala Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Leu Gly Val Tyr Tyr Cys Phe Gln Gly
                85                  90                  95
Ser His Val Pro Leu Thr Phe Gly Ala Gly Thr Lys Leu Glu Leu Lys
            100                 105                 110
Arg Ala Asp Ala Ala Pro Thr Val Ser Ile Phe Pro Pro Ser Ser Glu
        115                 120                 125
Gln Leu Thr Ser Gly Gly Ala Ser Val Val Cys Phe Leu Asn Asn Phe
    130                 135                 140
Tyr Pro Lys Asp Ile Asn Val Lys Trp Lys Ile Asp Gly Ser Glu Arg
145                 150                 155                 160
Gln Asn Gly Val Leu Asn Ser Trp Thr Asp Gln Asp Ser Lys Asp Ser
                165                 170                 175
Thr Tyr Ser Met Ser Ser Thr Leu Thr Leu Thr Lys Asp Glu Tyr Glu
            180                 185                 190
Arg His Asn Ser Tyr Thr Cys Glu Ala Thr His Lys Thr Ser Thr Ser
        195                 200                 205
Pro Ile Val Lys Ser Phe Asn Arg Asn Glu Cys
    210                 215
```

<210> SEQ ID NO 31
<211> LENGTH: 219
<212> TYPE: PRT
<213> ORGANISM: Artificial Sequence
<220> FEATURE:
<223> OTHER INFORMATION: De-N-glycosylated Light chain (2)

<400> SEQUENCE: 31

```
Asp Val Leu Met Thr Gln Thr Pro Leu Ser Leu Pro Val Ser Leu Gly
1               5                   10                  15
Asp Gln Ala Ser Ile Ser Cys Arg Ser Ser Gln Ser Ile Val His Ser
            20                  25                  30
Asn Arg Asn Thr Tyr Leu Glu Trp Tyr Leu Gln Lys Pro Gly Gln Ser
        35                  40                  45
Pro Lys Leu Leu Ile Tyr Gln Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Leu Gly Val Tyr Tyr Cys Phe Gln Gly
                85                  90                  95
Ser His Val Pro Leu Thr Phe Gly Ala Gly Thr Lys Leu Glu Leu Lys
            100                 105                 110
```

Arg Ala Asp Ala Ala Pro Thr Val Ser Ile Phe Pro Pro Ser Ser Glu
            115                 120                 125

Gln Leu Thr Ser Gly Gly Ala Ser Val Val Cys Phe Leu Asn Asn Phe
        130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
            165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
            195                 200                 205

Pro Ile Val Lys Ser Phe Asn Arg Asn Glu Cys
        210                 215

<210> SEQ ID NO 32
<211> LENGTH: 11
<212> TYPE: PRT
<213> ORGANISM: Artificial Sequence
<220> FEATURE:
<223> OTHER INFORMATION: VH complementarity determining region 1 (AA)

<400> SEQUENCE: 32

Gly Ser Ile Gly Arg Gly Ser Tyr Tyr Trp Gly
1               5                   10

<210> SEQ ID NO 33
<211> LENGTH: 16
<212> TYPE: PRT
<213> ORGANISM: Artificial Sequence
<220> FEATURE:
<223> OTHER INFORMATION: VH complementarity determining region 2 (AA)

<400> SEQUENCE: 33

Asn Ile Tyr Tyr Ser Gly Ser Thr Tyr Tyr Asn Pro Ser Leu Lys Ser
1               5                   10                  15

<210> SEQ ID NO 34
<211> LENGTH: 12
<212> TYPE: PRT
<213> ORGANISM: Artificial Sequence
<220> FEATURE:
<223> OTHER INFORMATION: VH complementarity determining region 3 (AA)

<400> SEQUENCE: 34

Ala Arg Glu Gly Ser Tyr Thr Thr Val Leu Asn Val
1               5                   10

<210> SEQ ID NO 35
<211> LENGTH: 12
<212> TYPE: PRT
<213> ORGANISM: Artificial Sequence
<220> FEATURE:
<223> OTHER INFORMATION: VL complementarity determining region 1 (AA)

<400> SEQUENCE: 35

Arg Ala Ser Gln Ser Val Ala Ser Ser His Leu Ala
1               5                   10

<210> SEQ ID NO 36
<211> LENGTH: 7
<212> TYPE: PRT
<213> ORGANISM: Artificial Sequence
<220> FEATURE:

<223> OTHER INFORMATION: VL complementarity determining region 2 (AA)

<400> SEQUENCE: 36

Asp Ala Val Ser Arg Ala Thr
1               5

<210> SEQ ID NO 37
<211> LENGTH: 9
<212> TYPE: PRT
<213> ORGANISM: Artificial Sequence
<220> FEATURE:
<223> OTHER INFORMATION: VL complementarity determining region3 (AA)

<400> SEQUENCE: 37

Gln Gln Ala Ala Ser Tyr Pro Leu Thr
1               5

<210> SEQ ID NO 38
<211> LENGTH: 25
<212> TYPE: PRT
<213> ORGANISM: Artificial Sequence
<220> FEATURE:
<223> OTHER INFORMATION: M6 VH Framework 1

<400> SEQUENCE: 38

Gln Val Thr Leu Lys Glu Ser Gly Pro Gly Ile Leu Gln Pro Ser Gln
1               5                   10                  15

Thr Leu Ser Leu Thr Cys Ser Phe Ser
            20                  25

<210> SEQ ID NO 39
<211> LENGTH: 19
<212> TYPE: PRT
<213> ORGANISM: Artificial Sequence
<220> FEATURE:
<223> OTHER INFORMATION: M6 VH Framework 2

<400> SEQUENCE: 39

Gly Val Gly Trp Ile Arg Gln Pro Ser Gly Lys Gly Leu Asp Trp Leu
1               5                   10                  15

Ala Asn Ile

<210> SEQ ID NO 40
<211> LENGTH: 41
<212> TYPE: PRT
<213> ORGANISM: Artificial Sequence
<220> FEATURE:
<223> OTHER INFORMATION: M6 VH Framework 3

<400> SEQUENCE: 40

Lys Tyr Tyr Asn Ser Ala Leu Lys Ser Arg Leu Thr Ile Ser Lys Asp
1               5                   10                  15

Thr Ser Asn Asn Gln Val Phe Leu Lys Ile Ser Ser Val Asp Thr Ala
            20                  25                  30

Asp Thr Gly Thr Tyr Tyr Cys Ala Gln
                35                  40

<210> SEQ ID NO 41
<211> LENGTH: 11
<212> TYPE: PRT
<213> ORGANISM: Artificial Sequence
<220> FEATURE:
<223> OTHER INFORMATION: M6 VH Framework 4

<400> SEQUENCE: 41

Trp Gly Ala Gly Thr Thr Val Thr Val Ser Ser
1               5                   10

<210> SEQ ID NO 42
<211> LENGTH: 25
<212> TYPE: PRT
<213> ORGANISM: Artificial Sequence
<220> FEATURE:
<223> OTHER INFORMATION: M11 VH Framework 1

<400> SEQUENCE: 42

Gln Val Thr Leu Lys Glu Ser Gly Pro Gly Ile Leu Gln Pro Ser Gln
1               5                   10                  15

Thr Leu Ser Leu Thr Cys Ser Leu Ser
            20                  25

<210> SEQ ID NO 43
<211> LENGTH: 19
<212> TYPE: PRT
<213> ORGANISM: Artificial Sequence
<220> FEATURE:
<223> OTHER INFORMATION: M11 VH Framework 2

<400> SEQUENCE: 43

Gly Val Gly Trp Ile Arg Gln Pro Ser Gly Lys Gly Leu Gly Trp Leu
1               5                   10                  15

Ala Asn Ile

<210> SEQ ID NO 44
<211> LENGTH: 41
<212> TYPE: PRT
<213> ORGANISM: Artificial Sequence
<220> FEATURE:
<223> OTHER INFORMATION: M11 VH Framework 3

<400> SEQUENCE: 44

Lys Tyr Tyr Asn Ser Ala Leu Lys Ser Arg Leu Thr Ile Ser Lys Asp
1               5                   10                  15

Thr Ser Asn Asn Gln Val Phe Leu Lys Ile Ser Ser Val Asp Thr Ala
            20                  25                  30

Asp Thr Gly Thr Tyr Tyr Cys Ala Gln
            35                  40

<210> SEQ ID NO 45
<211> LENGTH: 11
<212> TYPE: PRT
<213> ORGANISM: Artificial Sequence
<220> FEATURE:
<223> OTHER INFORMATION: M11 VH Framework 4

<400> SEQUENCE: 45

Trp Gly Ala Gly Thr Thr Val Thr Val Ser Ser
1               5                   10

<210> SEQ ID NO 46
<211> LENGTH: 25
<212> TYPE: PRT
<213> ORGANISM: Artificial Sequence
<220> FEATURE:
<223> OTHER INFORMATION: M15 VH Framework 1

<400> SEQUENCE: 46

Gln Val Thr Leu Lys Glu Ser Gly Pro Gly Ile Leu Gln Ser Ser Gln
1               5                   10                  15

Thr Leu Ser Leu Thr Cys Ser Phe Ser
            20                  25

<210> SEQ ID NO 47
<211> LENGTH: 19
<212> TYPE: PRT
<213> ORGANISM: Artificial Sequence
<220> FEATURE:
<223> OTHER INFORMATION: M15 VH Framework 2

<400> SEQUENCE: 47

Gly Val Gly Trp Ile Arg Gln Pro Ser Gly Lys Gly Leu Asp Trp Leu
1               5                   10                  15

Ala Asn Ile

<210> SEQ ID NO 48
<211> LENGTH: 41
<212> TYPE: PRT
<213> ORGANISM: Artificial Sequence
<220> FEATURE:
<223> OTHER INFORMATION: M15 VH Framework 3

<400> SEQUENCE: 48

Lys Tyr Tyr Asn Ser Ala Leu Lys Ser Arg Leu Thr Ile Ser Lys Asp
1               5                   10                  15

Thr Ser Asn Asn Gln Val Phe Leu Lys Ile Ser Val Asp Thr Ala
            20                  25                  30

Asp Thr Gly Thr Tyr Tyr Cys Ala Gln
        35                  40

<210> SEQ ID NO 49
<211> LENGTH: 11
<212> TYPE: PRT
<213> ORGANISM: Artificial Sequence
<220> FEATURE:
<223> OTHER INFORMATION: M15 VH Framework 4

<400> SEQUENCE: 49

Trp Gly Ala Gly Thr Thr Val Thr Val Ser Ser
1               5                   10

<210> SEQ ID NO 50
<211> LENGTH: 23
<212> TYPE: PRT
<213> ORGANISM: Artificial Sequence
<220> FEATURE:
<223> OTHER INFORMATION: M6, M11, M15 VL Framework 1

<400> SEQUENCE: 50

Asp Val Leu Met Thr Gln Thr Pro Leu Ser Leu Pro Val Ser Leu Gly
1               5                   10                  15

Asp Gln Ala Ser Ile Ser Cys
            20

<210> SEQ ID NO 51
<211> LENGTH: 14
<212> TYPE: PRT
<213> ORGANISM: Artificial Sequence
<220> FEATURE:
<223> OTHER INFORMATION: M6, M11, M15 VL Framework 2

<400> SEQUENCE: 51

Tyr Leu Gln Lys Pro Gly Gln Ser Pro Lys Leu Leu Ile Tyr
1               5                   10

-continued

<210> SEQ ID NO 52
<211> LENGTH: 32
<212> TYPE: PRT
<213> ORGANISM: Artificial Sequence
<220> FEATURE:
<223> OTHER INFORMATION: M6, M11, M15 VL Framework 3

<400> SEQUENCE: 52

Gly Val Pro Asp Arg Phe Ser Gly Ser Gly Ser Gly Thr Asp Phe Thr
1               5                   10                  15

Leu Lys Ile Ser Arg Val Glu Ala Glu Asp Leu Gly Val Tyr Tyr Cys
            20                  25                  30

<210> SEQ ID NO 53
<211> LENGTH: 10
<212> TYPE: PRT
<213> ORGANISM: Artificial Sequence
<220> FEATURE:
<223> OTHER INFORMATION: M6, M11, M15 VL Framework 4

<400> SEQUENCE: 53

Phe Gly Ala Gly Thr Lys Leu Glu Leu Lys
1               5                   10

<210> SEQ ID NO 54
<211> LENGTH: 120
<212> TYPE: PRT
<213> ORGANISM: Artificial Sequence
<220> FEATURE:
<223> OTHER INFORMATION: VH (AA)

<400> SEQUENCE: 54

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Gly Arg Gly
            20                  25                  30

Ser Tyr Tyr Trp Gly Trp Ile Arg Gln Pro Pro Gly Lys Gly Leu Glu
        35                  40                  45

Trp Ile Gly Asn Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Gly Ser Tyr Thr Thr Val Leu Asn Val Trp Gly Gln
            100                 105                 110

Gly Thr Met Val Thr Val Ser Ser
        115                 120

<210> SEQ ID NO 55
<211> LENGTH: 108
<212> TYPE: PRT
<213> ORGANISM: Artificial Sequence
<220> FEATURE:
<223> OTHER INFORMATION: VL (AA)

<400> SEQUENCE: 55

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ala Ser Ser
            20                  25                  30

His Leu Ala Trp Tyr Gln Gln Lys Pro Gly Gln Ala Pro Arg Leu Leu
         35                  40                  45

Ile Tyr Asp Ala Val Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Ala Ala Ser Tyr Pro
                 85                  90                  95

Leu Thr Phe Gly Gly Gly Thr Lys Val Glu Ile Lys
             100                 105

<210> SEQ ID NO 56
<211> LENGTH: 450
<212> TYPE: PRT
<213> ORGANISM: Artificial Sequence
<220> FEATURE:
<223> OTHER INFORMATION: Heavy Chain (AA)

<400> SEQUENCE: 56

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Gly Arg Gly
            20                  25                  30

Ser Tyr Tyr Trp Gly Trp Ile Arg Gln Pro Pro Gly Lys Gly Leu Glu
         35                  40                  45

Trp Ile Gly Asn Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Glu Gly Ser Tyr Thr Thr Val Leu Asn Val Trp Gly Gln
            100                 105                 110

Gly Thr Met Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

```
Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 57
<211> LENGTH: 215
<212> TYPE: PRT
<213> ORGANISM: Artificial Sequence
<220> FEATURE:
<223> OTHER INFORMATION: Light Chain (AA)

<400> SEQUENCE: 57

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ala Ser Ser
            20                  25                  30

His Leu Ala Trp Tyr Gln Gln Lys Pro Gly Gln Ala Pro Arg Leu Leu
        35                  40                  45

Ile Tyr Asp Ala Val Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ala Ala Ser Tyr Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190
```

```
Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 58
<211> LENGTH: 11
<212> TYPE: PRT
<213> ORGANISM: Artificial Sequence
<220> FEATURE:
<223> OTHER INFORMATION: VH complementarity determining region 1  (AA)

<400> SEQUENCE: 58

Gly Ser Ile Lys Ser Gly Ser Tyr Tyr Trp Gly
1               5                   10

<210> SEQ ID NO 59
<211> LENGTH: 16
<212> TYPE: PRT
<213> ORGANISM: Artificial Sequence
<220> FEATURE:
<223> OTHER INFORMATION: VH complementarity determining region 2 (AA)

<400> SEQUENCE: 59

Asn Ile Tyr Tyr Ser Gly Ser Thr Tyr Tyr Asn Pro Ser Leu Arg Ser
1               5                   10                  15

<210> SEQ ID NO 60
<211> LENGTH: 12
<212> TYPE: PRT
<213> ORGANISM: Artificial Sequence
<220> FEATURE:
<223> OTHER INFORMATION: VH complementarity determining region 3 (AA)

<400> SEQUENCE: 60

Ala Arg Glu Gly Ser Tyr Pro Asn Gln Phe Asp Pro
1               5                   10

<210> SEQ ID NO 61
<211> LENGTH: 11
<212> TYPE: PRT
<213> ORGANISM: Artificial Sequence
<220> FEATURE:
<223> OTHER INFORMATION: VL complementarity determining region 1 (AA)

<400> SEQUENCE: 61

Arg Ala Ser Gln Ser Val Ser Ser Asn Leu Ala
1               5                   10

<210> SEQ ID NO 62
<211> LENGTH: 7
<212> TYPE: PRT
<213> ORGANISM: Artificial Sequence
<220> FEATURE:
<223> OTHER INFORMATION: VL complementarity determining region 2 (AA)

<400> SEQUENCE: 62

Gly Ala Ser Thr Arg Ala Thr
1               5

<210> SEQ ID NO 63
<211> LENGTH: 9
<212> TYPE: PRT
<213> ORGANISM: Artificial Sequence
<220> FEATURE:
<223> OTHER INFORMATION: VL complementarity determining region 3 (AA)
```

<400> SEQUENCE: 63

Gln Gln Tyr His Ser Phe Pro Phe Thr
1               5

<210> SEQ ID NO 64
<211> LENGTH: 120
<212> TYPE: PRT
<213> ORGANISM: Artificial Sequence
<220> FEATURE:
<223> OTHER INFORMATION: VH (AA)

<400> SEQUENCE: 64

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Lys Ser Gly
            20                  25                  30

Ser Tyr Tyr Trp Gly Trp Ile Arg Gln Pro Pro Gly Lys Gly Leu Glu
        35                  40                  45

Trp Ile Gly Asn Ile Tyr Tyr Ser Gly Ser Thr Tyr Tyr Asn Pro Ser
    50                  55                  60

Leu Arg Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Gly Ser Tyr Pro Asn Gln Phe Asp Pro Trp Gly Gln
            100                 105                 110

Gly Thr Leu Val Thr Val Ser Ser
        115                 120

<210> SEQ ID NO 65
<211> LENGTH: 107
<212> TYPE: PRT
<213> ORGANISM: Artificial Sequence
<220> FEATURE:
<223> OTHER INFORMATION: VL (AA)

<400> SEQUENCE: 65

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr His Ser Phe Pro Phe
                85                  90                  95

Thr Phe Gly Gly Gly Thr Lys Val Glu Ile Lys
            100                 105

<210> SEQ ID NO 66
<211> LENGTH: 26
<212> TYPE: PRT
<213> ORGANISM: Artificial Sequence
<220> FEATURE:
<223> OTHER INFORMATION: VH Framework 1 (AA)

-continued

```
<400> SEQUENCE: 66

Gln Leu Gln Leu Gln Glu Ser Gly Pro Gly Leu Val Lys Pro Ser Glu
1               5                   10                  15

Thr Leu Ser Leu Thr Cys Thr Val Ser Gly
            20                  25

<210> SEQ ID NO 67
<211> LENGTH: 14
<212> TYPE: PRT
<213> ORGANISM: Artificial Sequence
<220> FEATURE:
<223> OTHER INFORMATION: VH Framework2 (AA)

<400> SEQUENCE: 67

Trp Ile Arg Gln Pro Pro Gly Lys Gly Leu Glu Trp Ile Gly
1               5                   10

<210> SEQ ID NO 68
<211> LENGTH: 30
<212> TYPE: PRT
<213> ORGANISM: Artificial Sequence
<220> FEATURE:
<223> OTHER INFORMATION: VH Framework 3 (AA)

<400> SEQUENCE: 68

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys
            20                  25                  30

<210> SEQ ID NO 69
<211> LENGTH: 11
<212> TYPE: PRT
<213> ORGANISM: Artificial Sequence
<220> FEATURE:
<223> OTHER INFORMATION: VH Framework 4 (AA)

<400> SEQUENCE: 69

Trp Gly Gln Gly Thr Leu Val Thr Val Ser Ser
1               5                   10

<210> SEQ ID NO 70
<211> LENGTH: 23
<212> TYPE: PRT
<213> ORGANISM: Artificial Sequence
<220> FEATURE:
<223> OTHER INFORMATION: VL Framework 1 (AA)

<400> SEQUENCE: 70

Glu Ile Val Met Thr Gln Ser Pro Ala Thr Leu Ser Val Ser Pro Gly
1               5                   10                  15

Glu Arg Ala Thr Leu Ser Cys
            20

<210> SEQ ID NO 71
<211> LENGTH: 15
<212> TYPE: PRT
<213> ORGANISM: Artificial Sequence
<220> FEATURE:
<223> OTHER INFORMATION: VL Framework 2 (AA)

<400> SEQUENCE: 71

Trp Tyr Gln Gln Lys Pro Gly Gln Ala Pro Arg Leu Leu Ile Tyr
1               5                   10                  15
```

<210> SEQ ID NO 72
<211> LENGTH: 32
<212> TYPE: PRT
<213> ORGANISM: Artificial Sequence
<220> FEATURE:
<223> OTHER INFORMATION: VL Framework 3 (AA)

<400> SEQUENCE: 72

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30

<210> SEQ ID NO 73
<211> LENGTH: 10
<212> TYPE: PRT
<213> ORGANISM: Artificial Sequence
<220> FEATURE:
<223> OTHER INFORMATION: VL Framework 4 (AA)

<400> SEQUENCE: 73

Phe Gly Gly Gly Thr Lys Val Glu Ile Lys
1               5                   10

<210> SEQ ID NO 74
<211> LENGTH: 450
<212> TYPE: PRT
<213> ORGANISM: Artificial Sequence
<220> FEATURE:
<223> OTHER INFORMATION: Heavy Chain (AA)

<400> SEQUENCE: 74

Gln Leu Gln Leu Gln Glu Ser Gly Pro Gly Leu Val Lys Pro Ser Glu
1               5                   10                  15

Thr Leu Ser Leu Thr Cys Thr Val Ser Gly Ser Ile Lys Ser Gly
            20                  25                  30

Ser Tyr Tyr Trp Gly Trp Ile Arg Gln Pro Pro Gly Lys Gly Leu Glu
        35                  40                  45

Trp Ile Gly Asn Ile Tyr Tyr Ser Gly Ser Thr Tyr Tyr Asn Pro Ser
    50                  55                  60

Leu Arg Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Gly Ser Tyr Pro Asn Gln Phe Asp Pro Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp

```
            210                 215                 220
Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 75
<211> LENGTH: 214
<212> TYPE: PRT
<213> ORGANISM: Artificial Sequence
<220> FEATURE:
<223> OTHER INFORMATION: Light Chain (AA)

<400> SEQUENCE: 75

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr His Ser Phe Pro Phe
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
```

```
            115                 120                 125
Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 76
<211> LENGTH: 360
<212> TYPE: PRT
<213> ORGANISM: Artificial Sequence
<220> FEATURE:
<223> OTHER INFORMATION: VH (N)

<400> SEQUENCE: 76

Cys Ala Gly Cys Thr Gly Cys Ala Gly Cys Thr Gly Cys Ala Gly Gly
1               5                   10                  15

Ala Gly Thr Cys Gly Gly Gly Cys Cys Cys Ala Gly Gly Ala Cys Thr
            20                  25                  30

Gly Gly Thr Gly Ala Ala Gly Cys Cys Thr Cys Gly Gly Ala Cys Ala
        35                  40                  45

Cys Cys Cys Thr Gly Thr Cys Cys Cys Thr Cys Ala Cys Cys Thr
    50                  55                  60

Gly Cys Ala Cys Thr Gly Thr Cys Thr Cys Thr Gly Gly Thr Gly Gly
65                  70                  75                  80

Cys Thr Cys Cys Ala Thr Cys Ala Ala Thr Ala Gly Thr Gly Gly Thr
                85                  90                  95

Ala Gly Thr Thr Ala Cys Thr Ala Cys Thr Gly Gly Gly Gly Cys Thr
            100                 105                 110

Gly Gly Ala Thr Cys Cys Gly Cys Cys Ala Gly Cys Cys Cys Cys Cys
        115                 120                 125

Ala Gly Gly Gly Ala Ala Gly Gly Gly Cys Thr Gly Gly Ala Gly Thr
    130                 135                 140

Thr Gly Gly Ala Thr Thr Gly Gly Gly Ala Ala Cys Ala Thr Cys Thr
145                 150                 155                 160

Ala Thr Thr Ala Thr Ala Gly Thr Gly Gly Gly Ala Gly Cys Ala Cys
                165                 170                 175

Cys Thr Ala Cys Thr Ala Cys Ala Ala Cys Cys Cys Gly Thr Cys Cys
            180                 185                 190

Cys Thr Cys Ala Ala Gly Ala Gly Thr Cys Gly Ala Gly Thr Cys Ala
        195                 200                 205

Cys Cys Ala Thr Ala Thr Cys Cys Gly Thr Ala Gly Ala Cys Ala Cys
    210                 215                 220

Gly Thr Cys Cys Ala Ala Gly Ala Ala Cys Cys Ala Gly Thr Thr Cys
225                 230                 235                 240

Thr Cys Cys Cys Thr Gly Ala Ala Gly Cys Thr Gly Ala Gly Thr Thr
                245                 250                 255

Cys Thr Gly Thr Gly Ala Cys Cys Gly Cys Cys Gly Cys Ala Gly Ala
```

260                 265                 270
Cys Ala Cys Gly Gly Cys Gly Thr Gly Thr Ala Cys Thr Ala Cys
            275                 280                 285
Thr Gly Cys Gly Cys Cys Ala Gly Ala Gly Ala Gly Gly Ala Thr
            290                 295                 300
Cys Thr Thr Ala Cys Cys Cys Ala Ala Thr Cys Ala Gly Thr Thr
305                 310                 315                 320
Thr Gly Ala Thr Cys Ala Thr Gly Gly Gly Ala Cys Ala Gly
            325                 330                 335
Gly Gly Thr Ala Cys Ala Thr Thr Gly Gly Thr Cys Ala Cys Cys Gly
            340                 345                 350
Thr Cys Thr Cys Cys Thr Cys Ala
            355                 360

<210> SEQ ID NO 77
<211> LENGTH: 321
<212> TYPE: DNA
<213> ORGANISM: Artificial Sequence
<220> FEATURE:
<223> OTHER INFORMATION: VL(N)

<400> SEQUENCE: 77
gaaatagtga tgacgcagtc tccagccacc ctgtctgtgt ctccagggga aagagccacc    60
ctctcctgca gggccagtca gagtgttagc agcaacttag cctggtacca gcagaaacct   120
ggccaggctc ccaggctcct catctatggt gcatccacca gggccactgg tatcccagcc   180
aggttcagtg gcagtgggtc tgggacagag ttcactctca ccatcagcag cctgcagtct   240
gaagattttg cagtttatta ctgtcagcag taccactcct tccctttcac ttttggcgga   300
gggaccaagg ttgagatcaa a                                              321

<210> SEQ ID NO 78
<211> LENGTH: 26
<212> TYPE: PRT
<213> ORGANISM: Artificial Sequence
<220> FEATURE:
<223> OTHER INFORMATION: VH Framework 1 (AA)

<400> SEQUENCE: 78

Gln Leu Gln Leu Gln Glu Ser Gly Pro Gly Leu Val Lys Pro Ser Glu
1               5                   10                  15
Thr Leu Ser Leu Thr Cys Thr Val Ser Gly
            20                  25

<210> SEQ ID NO 79
<211> LENGTH: 14
<212> TYPE: PRT
<213> ORGANISM: Artificial Sequence
<220> FEATURE:
<223> OTHER INFORMATION: VH Framework 2 (AA)

<400> SEQUENCE: 79

Trp Ile Arg Gln Pro Pro Gly Lys Gly Leu Glu Trp Ile Gly
1               5                   10

<210> SEQ ID NO 80
<211> LENGTH: 30
<212> TYPE: PRT
<213> ORGANISM: Artificial Sequence
<220> FEATURE:
<223> OTHER INFORMATION: VH FR3 (AA)

```
<400> SEQUENCE: 80

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys
            20                  25                  30

<210> SEQ ID NO 81
<211> LENGTH: 11
<212> TYPE: PRT
<213> ORGANISM: Artificial Sequence
<220> FEATURE:
<223> OTHER INFORMATION: VH Framework4 (AA)

<400> SEQUENCE: 81

Trp Gly Gln Gly Thr Met Val Thr Val Ser Ser
1               5                   10

<210> SEQ ID NO 82
<211> LENGTH: 23
<212> TYPE: PRT
<213> ORGANISM: Artificial Sequence
<220> FEATURE:
<223> OTHER INFORMATION: VL Framework 1 (AA)

<400> SEQUENCE: 82

Glu Ile Val Leu Thr Gln Ser Pro Gly Thr Leu Ser Leu Ser Pro Gly
1               5                   10                  15

Glu Arg Ala Thr Leu Ser Cys
            20

<210> SEQ ID NO 83
<211> LENGTH: 15
<212> TYPE: PRT
<213> ORGANISM: Artificial Sequence
<220> FEATURE:
<223> OTHER INFORMATION: VL Framework 2 (AA)

<400> SEQUENCE: 83

Trp Tyr Gln Gln Lys Pro Gly Gln Ala Pro Arg Leu Leu Ile Tyr
1               5                   10                  15

<210> SEQ ID NO 84
<211> LENGTH: 32
<212> TYPE: PRT
<213> ORGANISM: Artificial Sequence
<220> FEATURE:
<223> OTHER INFORMATION: VL Framework 3 (AA)

<400> SEQUENCE: 84

Gly Ile Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
            20                  25                  30

<210> SEQ ID NO 85
<211> LENGTH: 360
<212> TYPE: DNA
<213> ORGANISM: Artificial Sequence
<220> FEATURE:
<223> OTHER INFORMATION: VH (N)

<400> SEQUENCE: 85
cagctgcagc tgcaggagtc gggcccagga ctggtgaagc cttcggagac cctgtccctc      60
acctgcactg tctctggtgg ctccatcggg agggggagtt actactgggg ctggatccgc     120
```

```
cagcccccag ggaaggggct ggagtggatt gggaacatct attatagtgg gagcacctac    180
tacaacccgt ccctcaagag tcgagtcacc atatccgtag acacgtccaa gaaccagttc    240
tccctgaagc tgagttctgt gaccgccgca gacacggcgg tgtactactg cgccagagaa    300
ggatcttaca caaccgtgtt aaacgtatgg ggtcaggggta caatggtcac cgtctcctca    360
```

<210> SEQ ID NO 86
<211> LENGTH: 324
<212> TYPE: DNA
<213> ORGANISM: Artificial Sequence
<220> FEATURE:
<223> OTHER INFORMATION: VL (N)

<400> SEQUENCE: 86

```
gaaattgtgt tgacgcagtc tccaggcacc ctgtctttgt ctccagggga aagagccacc     60
ctctcctgca gggccagtca gagtgttgcc agcagccact tagcctggta ccagcagaaa    120
cctggccagg ctcccaggct cctcatctat gacgcagtca gcagggccac tggcatccca    180
gacaggttca gtggcagtgg gtctgggaca gacttcactc tcaccatcag cagactggag    240
cctgaagatt ttgcagtgta ttactgtcag caggccgcca gttaccctct cactttggc    300 ggagggacca aggttgagat caaa                                           324
```

<210> SEQ ID NO 87
<211> LENGTH: 324
<212> TYPE: PRT
<213> ORGANISM: Artificial Sequence
<220> FEATURE:
<223> OTHER INFORMATION: constant region of the heavy chain

<400> SEQUENCE: 87

```
Ala Lys Thr Thr Pro Pro Ser Val Tyr Pro Leu Ala Pro Gly Ser Ala
 1               5                  10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Glu Ser Asp Leu Tyr Thr Leu
    50                  55                  60

Ser Ser Ser Val Thr Val Pro Ser Ser Pro Arg Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Ile Lys Asp Val Leu
        115                 120                 125

Met Ile Ser Leu Ser Pro Ile Val Thr Cys Val Val Val Asp Val Ser
    130                 135                 140

Glu Asp Asp Pro Asp Val Gln Ile Ser Trp Phe Val Asn Asn Val Glu
145                 150                 155                 160

Val His Thr Ala Gln Thr Gln Thr His Arg Glu Asp Tyr Asn Ser Thr
                165                 170                 175

Leu Arg Val Val Ser Ala Leu Pro Ile Gln His Gln Asp Trp Met Ser
            180                 185                 190

Gly Lys Glu Phe Lys Cys Lys Val Asn Asn Lys Asp Leu Pro Ala Pro
        195                 200                 205
```

```
Ile Glu Arg Thr Ile Ser Lys Pro Lys Gly Ser Val Arg Ala Pro Gln
    210                 215                 220

Val Tyr Val Leu Pro Pro Glu Glu Met Thr Lys Lys Gln Val
225                 230                 235                 240

Thr Leu Thr Cys Met Val Thr Asp Phe Met Pro Glu Asp Ile Tyr Val
                245                 250                 255

Glu Trp Thr Asn Asn Gly Lys Thr Glu Leu Asn Tyr Lys Asn Thr Glu
                260                 265                 270

Pro Val Leu Asp Ser Asp Gly Ser Tyr Phe Met Tyr Ser Lys Leu Arg
            275                 280                 285

Val Glu Lys Lys Asn Trp Val Glu Arg Asn Ser Tyr Ser Cys Ser Val
        290                 295                 300

Val His Glu Gly Leu His Asn His His Thr Thr Lys Ser Phe Ser Arg
305                 310                 315                 320

Thr Pro Gly Lys

<210> SEQ ID NO 88
<211> LENGTH: 107
<212> TYPE: PRT
<213> ORGANISM: Artificial Sequence
<220> FEATURE:
<223> OTHER INFORMATION: constant region of the heavy chain

<400> SEQUENCE: 88

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105

<210> SEQ ID NO 89
<211> LENGTH: 444
<212> TYPE: PRT
<213> ORGANISM: Artificial Sequence
<220> FEATURE:
<223> OTHER INFORMATION: M6 H (J511) Heavy Chain

<400> SEQUENCE: 89

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Tyr
            20                  25                  30

Gly Leu Gly Val Gly Trp Ile Arg Gln Pro Ser Gly Lys Gly Leu Asp
        35                  40                  45

Trp Leu Ala Asn Ile Trp Trp Asn Asp Asp Lys Tyr Tyr Asn Ser Ala
    50                  55                  60

Leu Lys Ser Arg Leu Thr Ile Ser Lys Asp Thr Ser Asn Asn Gln Val
65                  70                  75                  80
```

```
Phe Leu Lys Ile Ser Ser Val Asp Thr Ala Asp Thr Gly Thr Tyr Tyr
                85                  90                  95

Cys Ala Gln Val Asp Gly Tyr Tyr Trp Tyr Phe Asp Val Trp Gly Ala
            100                 105                 110

Gly Thr Thr Val Thr Val Ser Ser Ala Lys Thr Thr Pro Pro Ser Val
        115                 120                 125

Tyr Pro Leu Ala Pro Gly Ser Ala Ala Gln Thr Asn Ser Met Val Thr
    130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Glu Ser Asp Leu Tyr Thr Leu Ser Ser Val Val Thr Val Pro Ser
            180                 185                 190

Ser Pro Arg Pro Ser Glu Thr Val Thr Cys Asn Val Ala His Pro Ala
        195                 200                 205

Ser Ser Thr Lys Val Asp Lys Lys Ile Val Pro Arg Asp Cys Gly Cys
    210                 215                 220

Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
                245                 250                 255

Thr Cys Val Val Val Asp Ile Ser Lys Asp Asp Pro Glu Val Gln Phe
            260                 265                 270

Ser Trp Phe Val Asp Asp Val Glu Val His Thr Ala Gln Thr Gln Pro
        275                 280                 285

Arg Glu Glu Gln Phe Asn Ser Thr Phe Arg Ser Val Ser Glu Leu Pro
    290                 295                 300

Ile Met His Gln Asp Trp Leu Asn Gly Lys Glu Phe Lys Cys Arg Val
305                 310                 315                 320

Asn Ser Ala Ala Phe Pro Ala Pro Ile Glu Lys Thr Ile Ser Lys Thr
                325                 330                 335

Lys Gly Arg Pro Lys Ala Pro Gln Val Tyr Thr Ile Pro Pro Pro Lys
            340                 345                 350

Glu Gln Met Ala Lys Asp Lys Val Ser Leu Thr Cys Met Ile Thr Asp
        355                 360                 365

Phe Phe Pro Glu Asp Ile Thr Val Glu Trp Gln Trp Asn Gly Gln Pro
    370                 375                 380

Ala Glu Asn Tyr Lys Asn Thr Gln Pro Ile Met Asn Thr Asn Gly Ser
385                 390                 395                 400

Tyr Phe Val Tyr Ser Lys Leu Asn Val Gln Lys Ser Asn Trp Glu Ala
                405                 410                 415

Gly Asn Thr Phe Thr Cys Ser Val Leu His Glu Gly Leu His Asn His
            420                 425                 430

His Thr Glu Lys Ser Leu Ser His Ser Pro Gly Lys
        435                 440

<210> SEQ ID NO 90
<211> LENGTH: 444
<212> TYPE: PRT
<213> ORGANISM: Artificial Sequence
<220> FEATURE:
<223> OTHER INFORMATION: M11 H (J513) Heavy Chain

<400> SEQUENCE: 90
```

-continued

```
Gln Val Thr Leu Lys Glu Ser Gly Pro Gly Ile Leu Gln Pro Ser Gln
1               5                   10                  15
Thr Leu Ser Leu Thr Cys Ser Leu Ser Gly Phe Ser Leu Ser Thr Tyr
            20                  25                  30
Gly Leu Gly Val Gly Trp Ile Arg Gln Pro Ser Gly Lys Gly Leu Gly
            35                  40                  45
Trp Leu Ala Asn Ile Trp Trp Asn Asp Asp Lys Tyr Tyr Asn Ser Ala
50                  55                  60
Leu Lys Ser Arg Leu Thr Ile Ser Lys Asp Thr Ser Asn Asn Gln Val
65                  70                  75                  80
Phe Leu Lys Ile Ser Ser Val Asp Thr Ala Asp Thr Gly Thr Tyr Tyr
                85                  90                  95
Cys Ala Gln Val Asp Gly Tyr Tyr Trp Tyr Phe Asp Val Trp Gly Ala
                100                 105                 110
Gly Thr Thr Val Thr Val Ser Ser Ala Lys Thr Thr Pro Pro Ser Val
            115                 120                 125
Tyr Pro Leu Ala Pro Gly Ser Ala Ala Gln Thr Asn Ser Met Val Thr
        130                 135                 140
Leu Gly Cys Leu Val Lys Gly Tyr Phe Pro Glu Pro Val Thr Val Thr
145                 150                 155                 160
Trp Asn Ser Gly Ser Leu Ser Ser Gly Val His Thr Phe Pro Ala Val
                165                 170                 175
Leu Glu Ser Asp Leu Tyr Thr Leu Ser Ser Ser Val Thr Val Pro Ser
            180                 185                 190
Ser Pro Arg Pro Ser Glu Thr Val Thr Cys Asn Val Ala His Pro Ala
        195                 200                 205
Ser Ser Thr Lys Val Asp Lys Lys Ile Val Pro Arg Asp Cys Gly Cys
210                 215                 220
Lys Pro Cys Ile Cys Thr Val Pro Glu Val Ser Ser Val Phe Ile Phe
225                 230                 235                 240
Pro Pro Lys Pro Lys Asp Val Leu Thr Ile Thr Leu Thr Pro Lys Val
                245                 250                 255
Thr Cys Val Val Val Asp Ile Ser Lys Asp Asp Pro Glu Val Gln Phe
            260                 265                 270
Ser Trp Phe Val Asp Asp Val Glu Val His Thr Ala Gln Thr Gln Pro
        275                 280                 285
Arg Glu Glu Gln Phe Asn Ser Thr Phe Arg Ser Val Ser Glu Leu Pro
290                 295                 300
Ile Met His Gln Asp Trp Leu Asn Gly Lys Glu Phe Lys Cys Arg Val
305                 310                 315                 320
Asn Ser Ala Ala Phe Pro Ala Pro Ile Glu Lys Thr Ile Ser Lys Thr
                325                 330                 335
Lys Gly Arg Pro Lys Ala Pro Gln Val Tyr Thr Ile Pro Pro Pro Lys
            340                 345                 350
Glu Gln Met Ala Lys Asp Lys Val Ser Leu Thr Cys Met Ile Thr Asp
        355                 360                 365
Phe Phe Pro Glu Asp Ile Thr Val Glu Trp Gln Trp Asn Gly Gln Pro
370                 375                 380
Ala Glu Asn Tyr Lys Asn Thr Gln Pro Ile Met Asn Thr Asn Gly Ser
385                 390                 395                 400
Tyr Phe Val Tyr Ser Lys Leu Asn Val Gln Lys Ser Asn Trp Glu Ala
                405                 410                 415
```

-continued

```
Gly Asn Thr Phe Thr Cys Ser Val Leu His Glu Gly Leu His Asn His
                420                 425                 430

His Thr Glu Lys Ser Leu Ser His Ser Pro Gly Lys
        435                 440
```

<210> SEQ ID NO 91
<211> LENGTH: 444
<212> TYPE: PRT
<213> ORGANISM: Artificial Sequence
<220> FEATURE:
<223> OTHER INFORMATION: M15 H (J515) Heavy Chain

<400> SEQUENCE: 91

```
Gln Val Thr Leu Lys Glu Ser Gly Pro Gly Ile Leu Gln Ser Ser Gln
1               5                   10                  15

Thr Leu Ser Leu Thr Cys Ser Phe Ser Gly Phe Ser Leu Ser Thr Tyr
            20                  25                  30

Gly Leu Gly Val Gly Trp Ile Arg Gln Pro Ser Gly Lys Gly Leu Asp
        35                  40                  45

Trp Leu Ala Asn Ile Trp Trp Asn Asp Asp Lys Tyr Tyr Asn Ser Ala
    50                  55                  60

Leu Lys Ser Arg Leu Thr Ile Ser Lys Asp Thr Ser Asn Asn Gln Val
65                  70                  75                  80

Phe Leu Lys Ile Ser Ser Val Asp Thr Ala Asp Thr Gly Thr Tyr Tyr
                85                  90                  95

Cys Ala Gln Val Asp Gly Tyr Tyr Trp Tyr Phe Asp Val Trp Gly Ala
            100                 105                 110

Gly Thr Thr Val Thr Val Ser Ser Ala Lys Thr Thr Pro Pro Ser Val
        115                 120                 125

Tyr Pro Leu Ala Pro Gly Ser Ala Ala Gln Thr Asn Ser Met Val Thr
    130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Glu Ser Asp Leu Tyr Thr Leu Ser Ser Ser Val Thr Val Pro Ser
            180                 185                 190

Ser Pro Arg Pro Ser Glu Thr Val Thr Cys Asn Val Ala His Pro Ala
        195                 200                 205

Ser Ser Thr Lys Val Asp Lys Lys Ile Val Pro Arg Asp Cys Gly Cys
    210                 215                 220

Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
                245                 250                 255

Thr Cys Val Val Val Asp Ile Ser Lys Asp Asp Pro Glu Val Gln Phe
            260                 265                 270

Ser Trp Phe Val Asp Asp Val Glu Val His Thr Ala Gln Thr Gln Pro
        275                 280                 285

Arg Glu Glu Gln Phe Asn Ser Thr Phe Arg Ser Val Ser Glu Leu Pro
    290                 295                 300

Ile Met His Gln Asp Trp Leu Asn Gly Lys Glu Phe Lys Cys Arg Val
305                 310                 315                 320

Asn Ser Ala Ala Phe Pro Ala Pro Ile Glu Lys Thr Ile Ser Lys Thr
                325                 330                 335
```

```
Lys Gly Arg Pro Lys Ala Pro Gln Val Tyr Thr Ile Pro Pro Pro Lys
            340                 345                 350

Glu Gln Met Ala Lys Asp Lys Val Ser Leu Thr Cys Met Ile Thr Asp
        355                 360                 365

Phe Phe Pro Glu Asp Ile Thr Val Glu Trp Gln Trp Asn Gly Gln Pro
    370                 375                 380

Ala Glu Asn Tyr Lys Asn Thr Gln Pro Ile Met Asn Thr Asn Gly Ser
385                 390                 395                 400

Tyr Phe Val Tyr Ser Lys Leu Asn Val Gln Lys Ser Asn Trp Glu Ala
                405                 410                 415

Gly Asn Thr Phe Thr Cys Ser Val Leu His Glu Gly Leu His Asn His
                420                 425                 430

His Thr Glu Lys Ser Leu Ser His Ser Pro Gly Lys
            435                 440

<210> SEQ ID NO 92
<211> LENGTH: 324
<212> TYPE: PRT
<213> ORGANISM: Artificial Sequence
<220> FEATURE:
<223> OTHER INFORMATION: constant region of heavy chain amino acid
      sequence

<400> SEQUENCE: 92

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Glu Ser Asp Leu Tyr Thr Leu
    50                  55                  60

Ser Ser Ser Val Thr Val Pro Ser Ser Pro Arg Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
        115                 120                 125

Thr Ile Thr Leu Thr Pro Lys Val Thr Cys Val Val Val Asp Ile Ser
    130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255
```

```
Glu Trp Gln Trp Asn Gly Gln Pro Ala Glu Asn Tyr Lys Asn Thr Gln
            260                 265                 270

Pro Ile Met Asn Thr Asn Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys
```

<210> SEQ ID NO 93
<211> LENGTH: 1391
<212> TYPE: DNA
<213> ORGANISM: Artificial Sequence
<220> FEATURE:
<223> OTHER INFORMATION: J511 Heavy chain

<400> SEQUENCE: 93

| | | | | | |
|---|---|---|---|---|---|
| tgggcaggct | tacttcttca | ttcctgctac | tgattgtccc | tgcatatgtc | ctgtcccagg | 60 |
| tcactctgaa | agagtctggc | cctgggatat | tgcagccctc | ccagaccctc | agtctgactt | 120 |
| gttctttctc | tgggttttca | ctgagcactt | atggtctggg | tgtaggttgg | attcgtcagc | 180 |
| cttcaggaa | gggtctggac | tggctggcca | acatttggtg | gaatgatgat | aaatactata | 240 |
| actcagccct | gaagagccgg | ctcacaatct | ccaaggatac | ctccaacaac | caggtattcc | 300 |
| tcaagatctc | cagtgtggac | actgcagata | ctggcacata | ctactgtgct | caagttgatg | 360 |
| gttactactg | gtacttcgat | gtctggggcg | cagggaccac | ggtcaccgtc | tcctcagcca | 420 |
| aaacgcacacc | accaagtgtc | tatccactgg | cccctggatc | tgctgcccaa | actaactcca | 480 |
| tggtgaccct | gggatgcctg | gtcaagggct | atttccctga | gccagtgaca | gtgacctgga | 540 |
| actctggatc | cctgtccagc | ggtgtgcaca | ccttcccagc | tgtcctggag | tctgacctct | 600 |
| acactctgag | cagctcagtg | actgtcccct | ccagccctcg | gcccagcgag | accgtcacct | 660 |
| gcaacgttgc | ccacccggcc | agcagcacca | aagtggacaa | gaaaattgtg | cccagggatt | 720 |
| gtggttgtaa | gccttgcata | tgtacagtcc | cagaagtatc | atctgtcttc | atcttccccc | 780 |
| caaagcccaa | ggatgtgctc | accattactc | tgactcctaa | ggtcacgtgt | gttgtggtag | 840 |
| acatcagcaa | ggatgatccc | gaggtccagt | tcagctggtt | tgtagatgat | gtggaggtgc | 900 |
| acacagctca | gacgcaaccc | cgggaggagc | agttcaacag | cactttccgc | tcagtcagtg | 960 |
| aacttcccat | catgcaccag | gactggctca | atggcaagga | gttcaaatgc | agggtcaaca | 1020 |
| gtgcagcttt | ccctgccccc | atcgagaaaa | ccatctccaa | aaccaaaggc | agaccgaagg | 1080 |
| ctccacaggt | gtacaccatt | ccacctccca | aggagcagat | ggccaaggat | aaagtcagtc | 1140 |
| tgacctgcat | gataacagac | ttcttccctg | aagacattac | tgtggagtgg | cagtggaatg | 1200 |
| ggcagccagc | ggagaactac | aagaacactc | agcccatcat | gaacacgaat | ggctcttact | 1260 |
| tcgtctacag | caagctcaat | gtgcagaaga | gcaactggga | ggcaggaaat | actttcacct | 1320 |
| gctctgtgtt | acatgagggc | ctgcacaacc | accatactga | agagagcctc | tcccactctc | 1380 |
| ctggtaaatg | a | | | | | 1391 |

<210> SEQ ID NO 94
<211> LENGTH: 1392
<212> TYPE: DNA
<213> ORGANISM: Artificial Sequence
<220> FEATURE:

<223> OTHER INFORMATION: J513 Heavy chain

<400> SEQUENCE: 94

| | | | | | |
|---|---|---|---|---|---|
| atgggcaggc | ttacttcttc | attcctgcta | ctgattgtcc | ctgcatatgt | cctgtcccag | 60 |
| gtcactctga | aagagtctgg | ccctgggata | ttgcagccct | cccagaccct | cagtctgact | 120 |
| tgttctctct | ctgggttttc | actgagcact | tatggtctgg | gtgtaggttg | gattcgtcag | 180 |
| ccttcaggga | agggtctggg | ctggctggcc | aacatttggt | ggaatgatga | taaatactat | 240 |
| aactcagccc | tgaagagccg | gctcacaatc | tccaaggata | cctccaacaa | ccaggtattc | 300 |
| ctcaagatct | ccagtgtgga | cactgcagat | actggcacat | actactgtgc | tcaagttgat | 360 |
| ggttactact | ggtacttcga | tgtctggggc | gcagggacca | cggtcaccgt | ctcctcagcc | 420 |
| aaaacgacac | caccaagtgt | ctatccactg | gcccctggat | ctgctgccca | aactaactcc | 480 |
| atggtgaccc | tgggatgcct | ggtcaagggc | tatttccctg | agccagtgac | agtgacctgg | 540 |
| aactctggat | ccctgtccag | cggtgtgcac | accttcccag | ctgtcctgga | gtctgacctc | 600 |
| tacactctga | gcagctcagt | gactgtcccc | tccagccctc | ggcccagcga | gaccgtcacc | 660 |
| tgcaacgttg | cccacccggc | cagcagcacc | aaggtggaca | agaaaattgt | gcccagggat | 720 |
| tgtggttgta | agccttgcat | atgtacagtc | ccagaagtat | catctgtctt | catcttcccc | 780 |
| ccaaagccca | aggatgtgct | caccattact | ctgactccta | aggtcacgtg | tgttgtggta | 840 |
| gacatcagca | aggatgatcc | cgaggtccag | ttcagctggt | ttgtagatga | tgtggaggtg | 900 |
| cacacagctc | agacgcaacc | ccgggaggag | cagttcaaca | gcactttccg | ctcagtcagt | 960 |
| gaacttccca | tcatgcacca | ggactggctc | aatggcaagg | agttcaaatg | cagggtcaac | 1020 |
| agtgcagctt | tccctgcccc | catcgagaaa | accatctcca | aaaccaaagg | cagaccgaag | 1080 |
| gctccacagg | tgtacaccat | tccacctccc | aaggagcaga | tggccaagga | taaagtcagt | 1140 |
| ctgacctgca | tgataacaga | cttcttccct | gaagacatta | ctgtggagtg | gcagtggaat | 1200 |
| gggcagccag | cggagaacta | caagaacact | cagcccatca | tgaacacgaa | tggctcttac | 1260 |
| ttcgtctaca | gcaagctcaa | tgtgcagaag | agcaactggg | aggcaggaaa | tactttcacc | 1320 |
| tgctctgtgt | tacatgaggg | cctgcacaac | caccatactg | agaagagcct | ctcccactct | 1380 |
| cctggtaaat | ga | | | | | 1392 |

<210> SEQ ID NO 95
<211> LENGTH: 1392
<212> TYPE: DNA
<213> ORGANISM: Artificial Sequence
<220> FEATURE:
<223> OTHER INFORMATION: J515 heavy Chain

<400> SEQUENCE: 95

| | | | | | |
|---|---|---|---|---|---|
| atgggcaggc | ttacttcttc | attcctgcta | ctgattgtcc | ctgcatatgt | cctgtcccag | 60 |
| gtcactctga | aagagtctgg | ccctgggata | ttgcagtcct | cccagaccct | cagtctgact | 120 |
| tgttctttct | ctgggttttc | actgagcact | tatggtctgg | gtgtaggttg | gattcgtcag | 180 |
| ccttcaggga | agggtctgga | ctggctggcc | aacatttggt | ggaatgatga | taaatactat | 240 |
| aactcagccc | tgaagagccg | gctcacaatc | tccaaggata | cctccaacaa | ccaggtattc | 300 |
| ctcaagatct | ccagtgtgga | cactgcagat | actggcacat | actactgtgc | tcaagttgat | 360 |
| ggttactact | ggtacttcga | tgtctggggc | gcagggacca | cggtcaccgt | ctcctcagcc | 420 |
| aaaacgacac | caccaagtgt | ctatccactg | gcccctggat | ctgctgccca | aactaactcc | 480 |
| atggtgaccc | tgggatgcct | ggtcaagggc | tatttccctg | agccagtgac | agtgacctgg | 540 |

```
aactctggat ccctgtccag cggtgtgcac accttcccag ctgtcctgga gtctgacctc    600
tacactctga gcagctcagt gactgtcccc tccagccctc ggcccagcga gaccgtcacc    660
tgcaacgttg cccacccggc cagcagcacc aaggtggaca gaaaattgt gcccagggat     720 tgtggttgta agccttgcat atgtacagtc ccagaagtat catctgtctt catcttcccc    780
ccaaagccca aggatgtgct caccattact ctgactccta aggtcacgtg tgttgtggta    840
gacatcagca aggatgatcc cgaggtccag ttcagctggt ttgtagatga tgtggaggtg    900
cacacagctc agacgcaacc ccgggaggag cagttcaaca gcactttccg ctcagtcagt    960
gaacttccca tcatgcacca ggactggctc aatggcaagg agttcaaatg cagggtcaac   1020
agtgcagctt tccctgcccc catcgagaaa accatctcca aaccaaagg cagaccgaag    1080 gctccacagg tgtacaccat tccacctccc aaggagcaga tggccaagga taaagtcagt   1140
ctgacctgca tgataacaga cttcttccct gaagacatta ctgtggagtg cagtggaat    1200 gggcagccag cggagaacta caagaacact cagcccatca tgaacacgaa tggctcttac   1260
ttcgtctaca gcaagctcaa tgtgcagaag agcaactggg aggcaggaaa tactttcacc   1320
tgctctgtgt tacatgaggg cctgcacaac caccatactg agaagagcct ctcccactct   1380
cctggtaaat ga                                                        1392

<210> SEQ ID NO 96
<211> LENGTH: 717
<212> TYPE: DNA
<213> ORGANISM: Artificial Sequence
<220> FEATURE:
<223> OTHER INFORMATION: J517, J519, and J521 Light Chain

<400> SEQUENCE: 96
atgaagttgc ctgttaggct gttggtgctg atgttctgga ttcctgcttc cggcagtgat     60
gttttgatga cccaaactcc actctcccty cctgtcagtc ttggagatca agcctccatc   120
tcttgcagat ctagtcagag cattgtacat agtaatagaa cacctatttt agaatggtac    180
ctgcagaaac caggccagtc tccaaagctc ctgatctaca cgttgccaa ccgattttct     240 ggggtcccag acaggttcag tggcagtgga tcagggacag atttcacact caagatcagc    300
agagtggagg ctgaggatct gggagtttat tactgctttc aaggttcaca tgttccgctc    360
acgttcggtc tgggaccaa gctggagctg aaacgggctg atgctgcacc aactgtatcc    420
atcttcccac catccagtga gcagttgaca tctggaggtg cctcagtcgt gtgcttcttg    480
aacaacttct accccaaaga catcaatgtc aagtggaaga ttgatggcag tgaacgacaa    540
aatggcgtcc tgaacagttg gactgatcag gacagcaaag acagcaccta cagcatgagc    600 agcacccttca cgttgaccaa ggacgagtat gaacgacata acagctatac ctgtgaggcc    660
actcacaaga tcaacttca cccattgtc aagagcttca caggaatga gtgttag          717

<210> SEQ ID NO 97
<211> LENGTH: 717
<212> TYPE: DNA
<213> ORGANISM: Artificial Sequence
<220> FEATURE:
<223> OTHER INFORMATION: J518, J520, and J522 Light Chain

<400> SEQUENCE: 97
atgaagttgc ctgttaggct gttggtgctg atgttctgga ttcctgcttc cggcagtgat     60
gttttgatga cccaaactcc actctcccty cctgtcagtc ttggagatca agcctccatc   120
```

-continued

```
tcttgcagat ctagtcagag cattgtacat agtaatagaa acacctattt agaatggtac    180
ctgcagaaac caggccagtc tccaaagctc ctgatctacc aggtttccaa ccgattttct    240
ggggtcccag acaggttcag tggcagtgga tcagggacag atttcacact caagatcagc    300
agagtggagg ctgaggatct gggagtttat tactgctttc aaggttcaca tgttccgctc    360
acgttcggtg ctgggaccaa gctggagctg aaacgggctg atgctgcacc aactgtatcc    420
atcttcccac catccagtga gcagttgaca tctggaggtg cctcagtcgt gtgcttcttg    480
aacaacttct accccaaaga catcaatgtc aagtggaaga ttgatggcag tgaacgacaa    540
aatggcgtcc tgaacagttg gactgatcag gacagcaaag acagcaccta cagcatgagc    600
agcaccctca cgttgaccaa ggacgagtat gaacgacata acagctatac ctgtgaggcc    660
actcacaaga catcaacttc acccattgtc aagagcttca acaggaatga gtgttag     717
```

<210> SEQ ID NO 98
<211> LENGTH: 10
<212> TYPE: PRT
<213> ORGANISM: Artificial Sequence
<220> FEATURE:
<223> OTHER INFORMATION: VL Framework 4 (AA)

<400> SEQUENCE: 98

Phe Gly Gly Gly Thr Lys Val Glu Ile Lys
1               5                   10

B7-H4 ANTIBODIES AND METHODS AND USE THEREOF

CROSS REFERENCE TO RELATED APPLICATIONS

This application is a Continuation application of International Patent Application No. PCT/US2019/020189, filed on Mar. 1, 2019, which claims the benefit of US Provisional Application No. 62/637,740, filed on Mar. 2, 2018, the contents of which are incorporated herein by reference their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 204122000401SEQLIST.TXT, date recorded: Aug. 21, 2020, size: 103 KB).

FIELD

The present disclosure relates to antibodies that specifically bind to human B7-H4 and methods of producing and using such antibodies, for example to detect B7-H4.

BACKGROUND

B7-H4 (also known as B7x, B7-S1, and VTCN1) is an immune regulatory molecule that shares homology with other B7 family members, include PD-L1. It is a type I transmembrane protein comprised of both IgV and IgC ectodomains. While B7-H4 expression in healthy tissues is relatively limited at the protein level, B7-H4 is expressed in several solid tumors such as gynecological carcinomas of the breast, ovary, and endometrium. Expression of B7-H4 in tumors tends to correlate with poor prognosis. The receptor for B7-H4 is unknown, but it is believed to be expressed on T cells. B7-H4 is believed to directly inhibit T cell activity.

Given the expression and function of B7-H4, antibodies that specifically bind to B7-H4 and the use of these antibodies to detect B7-H4, including, e.g., using immunohistochemistry (IHC) to detect B7-H4 in cancer samples, are needed.

SUMMARY

Provided herein are antibodies that specifically bind to B7-H4 and the use of these antibodies to detect B7-H4, including, e.g., using immunohistochemistry (IHC) to detect B7-H4 in cancer samples.

In certain embodiments, provided herein is an isolated antibody or antigen-binding fragment thereof that specifically binds to human B7-H4, comprising a heavy chain variable region (VH) complementarity determining region (CDR) 1 comprising the amino acid sequence of SEQ ID NO:22, a VH CDR2 comprising the amino acid sequence of SEQ ID NO:23, a VH CDR3 comprising the amino acid sequence of SEQ ID NO:24, a light chain variable region (VL) CDR1 comprising the amino acid sequence of SEQ ID NO:25, a VL CDR2 comprising the amino acid sequence of SEQ ID NO:26, 27, or 28, and a VL CDR3 sequence comprising the amino acid sequence of SEQ ID NO:29.

In certain embodiments, the antibody or antigen-binding fragment thereof comprises a VH comprising the amino acid sequence of SEQ ID NO-6, 7, or 8. In certain embodiments, the antibody or antigen-binding fragment thereof comprises a VL comprising the amino acid sequence of SEQ ID NO:9, 10, or 11.

In certain embodiments, provided herein is an isolated antibody or antigen-binding fragment thereof that specifically binds to human B7-H4, wherein the antibody or antigen-binding fragment thereof comprises a heavy chain variable region and a light chain variable region, wherein the heavy chain variable region comprises the amino acid sequence of SEQ ID NO:6, 7, or 8.

In certain embodiments, provided herein is an isolated antibody or antigen-binding fragment thereof that specifically binds to human B7-H4, wherein the antibody comprises a heavy chain variable region and a light chain variable region, wherein the light chain variable region comprises the amino acid sequence of SEQ ID NO:9, 10, or 11.

In certain embodiments, provided herein is an isolated antibody or antigen-binding fragment thereof that specifically binds to human B7-H4, comprising a heavy chain variable region and a light chain variable region comprising the amino acid sequences of: (a) SEQ ID NOs:6 and 9, respectively; (b) SEQ ID NOs:6 and 10, respectively; (c) SEQ ID NOs:6 and 11, respectively; (d) SEQ ID NOs:7 and 9, respectively; (e) SEQ ID NOs:7 and 10, respectively; (f) SEQ ID NOs:7 and 11, respectively; (g) SEQ ID NOs:8 and 9, respectively; (h) SEQ ID NOs:8 and 10, respectively; (i) SEQ ID NOs:8 and 11, respectively, (j) SEQ ID NOs: 89 and 19, respectively; (k) SEQ ID NOs: 90 and 19, respectively; or (l) SEQ ID NOs: 91 and 19, respectively.

In certain embodiments, the antibody or antigen-binding fragment thereof further comprises a heavy chain constant region. In certain embodiments, the heavy chain constant region is a murine IgG$_1$ or IgG$_{2a}$ heavy chain constant region.

In certain embodiments, the antibody or antigen-binding fragment further comprises a light chain constant region. In certain embodiments, light chain constant region is a murine IgGκ light chain constant region.

In certain embodiments, the antibody or antigen-binding fragment thereof comprises a heavy chain comprising the amino acid sequence of SEQ ID NO:16, 17, 18, 89, 90, or 91. In certain embodiments, the antibody or antigen-binding fragment thereof comprises a light chain comprising the amino acid sequence of SEQ ID NO:19, 30, or 31.

In certain embodiments, the antibody or antigen-binding fragment comprises a heavy chain and a light chain comprising the amino acid sequences of: (a) SEQ ID NOs:16 and 19, respectively; (b) SEQ ID NOs:16 and 30, respectively; (c) SEQ ID NOs:16 and 31, respectively; (d) SEQ ID NOs:17 and 19, respectively; (e) SEQ ID NOs: 17 and 30, respectively; (f) SEQ ID NOs:17 and 31, respectively; (g) SEQ ID NOs:18 and 19, respectively; (h) SEQ ID NOs:18 and 30, respectively; or (i) SEQ ID NOs:18 and 31, respectively.

In certain embodiments, provided herein is an isolated antibody or antigen-binding fragment thereof that specifically binds to human B7-H4, wherein the antibody or antigen-binding fragment thereof comprises the VH CDR1, VH CDR2, VH CDR3, VL CDR1, VL CDR2, and VL CDR3 of an antibody selected from the group consisting of J512, J513, J514, J515, J516, J517, J518, J519, J520, J521, and J522. In certain embodiments, the CDRs are the Kabat-defined CDRs, the Chothia-defined CDRs, or the AbM-defined CDRs.

In certain embodiments, provided herein is an isolated antibody or antigen-binding fragment thereof that specifically binds to the same epitope of human B7-H4 as an antibody or antigen-binding fragment thereof provided herein.

In certain embodiments, provided herein is an isolated antibody or antigen-binding fragment thereof that competitively inhibits binding of the antibody or antigen-binding fragment thereof of another antibody or antigen-binding fragment thereof provided herein to human B7-H4.

In certain embodiments, the antibody or antigen-binding fragment thereof is a murine antibody or antigen-binding fragment thereof.

In certain embodiments, the antibody or antigen-binding fragment thereof is a full length antibody. In certain embodiments, the antibody or antigen-binding fragment thereof is an antigen binding fragment. In certain embodiments, the antigen binding fragment comprises a Fab, Fab', F(ab')$_2$, single chain Fv (scFv), disulfide linked Fv, minibody, F(ab')$_3$, diabody, (scFv)$_2$, or scFv-Fc.

In certain embodiments, the antibody or antigen-binding fragment thereof further comprises a detectable label.

In certain embodiments, provided herein is an isolated polynucleotide comprising a nucleic acid molecule encoding the heavy chain variable region or heavy chain of an antibody or antigen-biding fragment thereof provided herein. In certain embodiments, the nucleic acid molecule encodes the VH of SEQ ID NO:6, 7, or 8 or the heavy chain of SEQ ID NO:16, 17, or 18.

In certain embodiments, the nucleic acid molecule comprises the sequence of SEQ ID NO:12, 13, 14, 93, 94, or 95.

In certain embodiments, provided herein is an isolated polynucleotide comprising a nucleic acid molecule encoding the light chain variable region or light chain of an antibody or antigen-biding fragment thereof provided herein. In certain embodiments, the nucleic acid molecule encodes the VL of SEQ ID NO:9, 10, or 11 or the light chain of SEQ ID NO:19, 30, or 31. In certain embodiments, the nucleic acid molecule comprises the sequence of SEQ ID NO:15, 96, or 97.

In certain embodiments, provided herein is an isolated polynucleotide comprising a nucleic acid molecule encoding the heavy chain variable region or heavy chain of an antibody or antigen-binding fragment thereof provided herein and the light chain variable region or light chain of the antibody or antigen-binding fragment thereof provided herein.

In certain embodiments, provided herein is an isolated vector comprising a polynucleotide provided herein.

In certain embodiments, provided herein is a host cell (e.g., an isolated host cell) comprising a polynucleotide provided herein, a vector provided herein, or a first vector comprising a polynucleotide encoding a light chain variable region or light chain provided herein and a second vector comprising a polynucleotide encoding a heavy chain variable region or heavy chain provided herein. In certain embodiments, the host cell is a CHO or HEK cell.

In certain embodiments, provided herein is a method of producing an antibody or antigen-binding fragment thereof that specifically binds to human B7-H4 comprising culturing a host cell of provided herein so that the nucleic acid molecule is expressed and the antibody or antigen-biding fragment thereof is produced.

In certain embodiments, provided herein is an isolated antibody or antigen-binding fragment thereof that specifically binds to human B7-H4 and is encoded by a polynucleotide provided herein.

In certain embodiments, provided herein is a method for detecting B7-H4 in a sample comprising contacting the sample with an antibody or antigen-binding fragment thereof provided herein. In certain embodiments, provided herein is a method for detecting B7-H4 in a sample comprising contacting the sample with an anti-B7-H4 antibody or antigen-binding fragment thereof provided herein and detecting binding of the antibody or antigen-binding fragment thereof to B7-H4. In certain embodiments, the sample is obtained from a cancer in a subject. In certain embodiments, the method further comprises administering a therapeutic anti-B7-H4 antibody or antigen-binding fragment thereof to the subject after B7-H4 has been detected.

In certain embodiments, provided herein is a method of treating a B7-H4 expressing cancer in a subject, the method comprising administering to the subject a therapeutic anti-B7-H4 antibody or antigen-binding fragment thereof, wherein B7-H4 was detected in a sample obtained from the cancer using an antibody or antigen-binding fragment thereof provided herein.

In certain embodiments, the method further comprises detecting the B7-H4 in the sample obtained from the cancer.

In certain embodiments, the detected B7-H4 is cell membrane B7-H4. In certain embodiments, the detected B7-H4 is cytoplasmic B7-H4. In certain embodiments, the detected B7-H4 is whole-cell B7-H4.

In certain embodiments, the B7-H4 is detected in circulating tumor cells.

In certain embodiments, the sample is solid tissue, biopsy, ascites, an aspirate, a fluidic extract, blood plasma, serum, spinal fluid, lymph fluid, the external section of the skin, respiratory, intestinal, or genitourinary tract, tears, saliva, milk, a tumor, or an organ from a subject.

In certain embodiments, the cancer is selected from the group consisting of breast cancer, ductal carcinoma, endometrial carcinoma, ovarian cancer, non-small cell lung cancer, pancreatic cancer, thyroid cancer, kidney cancer and bladder cancer. In certain embodiments, the breast cancer is triple negative breast cancer or wherein the non-small cell lung cancer is squamous cell carcinoma.

In certain embodiments, the method of detection uses an enzyme linked immunosorbent assay (ELISA), a fluorescence-activated cell sorter (FACS) assay, or immunohistochemistry (IHC). In certain embodiments, the method of detection uses IHC and the concentration of the antibody or antigen-binding fragment thereof provided herein is about 1 to about 50 μg/ml. In certain embodiments, the concentration of the antibody or antigen-binding fragment thereof provided herein is about 1 to about 20 μg/ml. In certain embodiments, the concentration of the antibody or antigen-binding fragment thereof provided herein is about 10 μg/mL.

In certain embodiments, the subject is human.

In certain embodiments, provided herein is a kit comprising an antibody or antigen-binding fragment thereof provided herein and a) a detection reagent, b) a B7-H4 antigen, c) a therapeutic anti-B7-H4 antibody, or d) a combination thereof.

In certain embodiments of the method or kit provided herein, the therapeutic antibody or antigen-binding fragment comprises the VH CDR1, VH CDR2, VH CDR3, VL CDR1, VL CDR2, and VL CDR3 of 20502 or 22213. In certain embodiments, the CDRs are the Kabat-defined CDRs, the Chothia-defined CDRs, or the AbM-defined CDR.

In certain embodiments, the VH CDR1, VH CDR2, VH CDR3, VL CDR1, VL CDR2, and VL CDR3 comprise the amino acid sequences of SEQ ID NOs:32-37, respectively or the amino acid sequences of SEQ ID NOs:58-63, respectively. In certain embodiments, the therapeutic antibody or antigen-binding fragment comprises a heavy chain variable region and a light chain variable region, wherein the heavy chain variable region comprises the amino acid sequence of SEQ ID NO:54 or SEQ ID NO:64. In certain embodiments, the therapeutic antibody or antigen-binding fragment comprises a heavy chain variable region and a light chain variable region, wherein the light chain variable region comprises the amino acid sequence of SEQ ID NO:55 or SEQ ID NO:65. In certain embodiments, the therapeutic antibody or antigen-binding fragment comprises (i) a heavy chain variable region comprising the amino acid sequence of SEQ ID NO:54 and a light chain variable region comprising the amino acid sequence of SEQ ID NO:55 or (ii) a heavy chain variable region comprising the amino acid sequence of SEQ ID NO:64 and a light chain variable region comprising the amino acid sequence of SEQ ID NO:65. In certain embodiments, the therapeutic antibody or antigen-binding fragment thereof comprises a heavy chain comprising the amino acid sequence of SEQ ID NO:56 or SEQ ID NO:74. In certain embodiments, the therapeutic antibody or antigen-binding fragment thereof comprises a light chain comprising the amino acid sequence of SEQ ID NO:57 or SEQ ID NO:75. In certain embodiments, the therapeutic antibody or antigen-binding fragment thereof comprises (i) a heavy chain comprising the amino acid sequence of SEQ ID NO:56 and a light chain comprising the amino acid sequence of SEQ ID NO:57 or (ii) a heavy chain comprising the amino acid sequence of SEQ ID NO:74 and a light chain comprising the amino acid sequence of SEQ ID NO:75.

BRIEF DESCRIPTION OF THE FIGURES

FIG. 5A shows the B7-H4 expression (DAB intensity) using A57.1 antibody. FIG. 5B shows the B7-H4 expression (DAB intensity) using J512 antibody. FIG. 5C shows the B7-H4 expression (DAB intensity) using J516 antibody. (See Example 4.)

DETAILED DESCRIPTION

Figure 1:
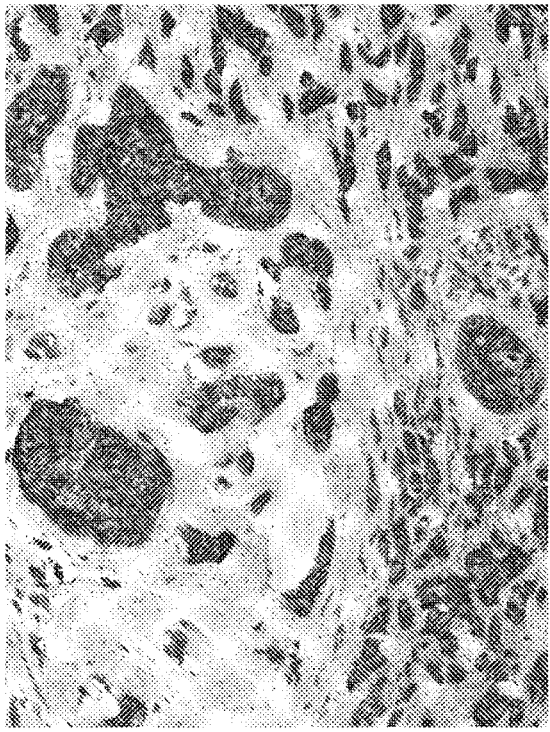
FIG. 1 shows IHC staining images generated using the anti-B7-H4 antibodies A57.1, AET_AB_J516, and AET_AB_J512. (See Example 4.)
Figure 1:
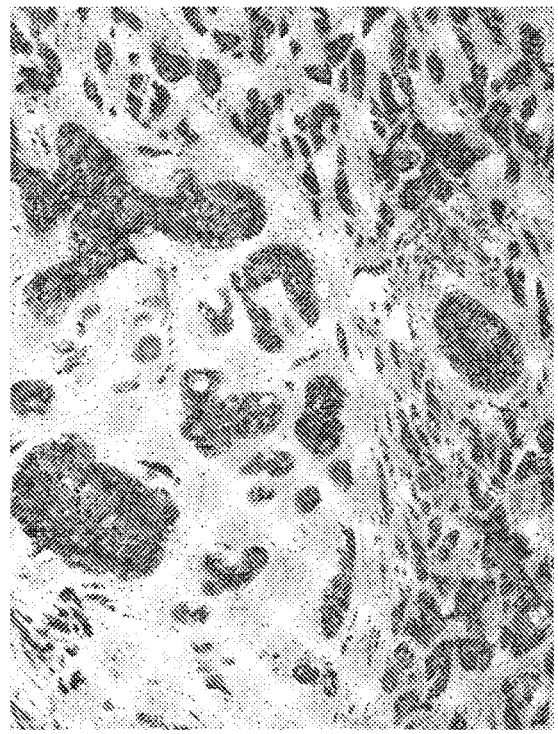
Figure 1:
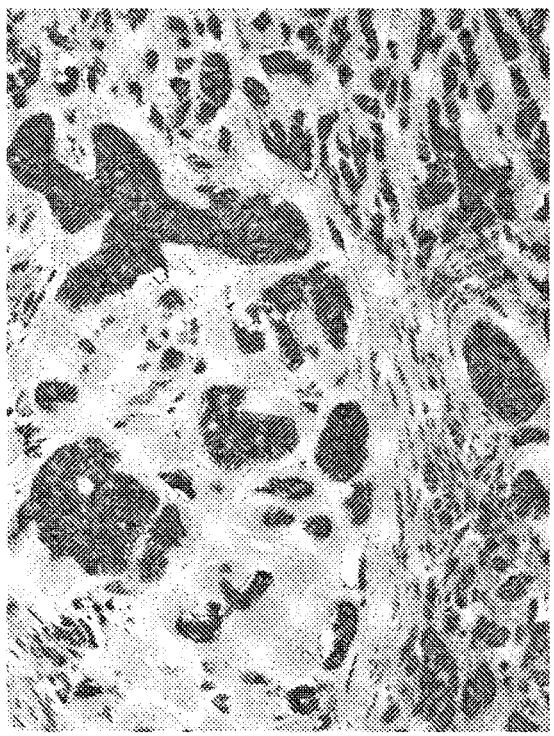

Provided herein are antibodies (e.g., monoclonal antibodies) and antigen-binding fragments thereof that specifically bind to B7-H4 (e.g., human B7-H4). The anti-B7-H4 antibodies and antigen-binding fragments thereof can be used to detect B7-H4, for example, using immunohistochemistry on a cancer sample.

Also provided are isolated nucleic acids (polynucleotides), such as complementary DNA (cDNA), encoding such antibodies and antigen-binding fragments thereof. Further provided are vectors (e.g., expression vectors) and cells (e.g., host cells) comprising nucleic acids (polynucleotides) encoding such antibodies and antigen-binding fragments thereof. Also provided are methods of making such antibodies and antigen-binding fragments thereof. In other aspects, provided herein are methods for detecting B7-H4, e.g., in a cancer sample. Related compositions (e.g., detection compositions), and kits are also provided.

Terminology

As used herein, the term "B7-H4" refers to mammalian B7-H4 polypeptides including, but not limited to, native B7-H4 polypeptides and isoforms of B7-H4 polypeptides. "B7-H4" encompasses full-length, unprocessed B7-H4 polypeptides as well as forms of B7-H4 polypeptides that result from processing within the cell. As used herein, the term "human B7-H4" refers to a polypeptide comprising the amino acid sequence of SEQ ID NO:1. A "B7-H4 polynucleotide," "B7-H4 nucleotide," or "B7-H4 nucleic acid" refer to a polynucleotide encoding B7-H4.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, chimeric antibodies, humanized antibodies, human antibodies, fusion proteins comprising an antibody, and any other modified immunoglobulin molecule so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

The term "antibody fragment" refers to a portion of an intact antibody. An "antigen-binding fragment," "antigen-binding domain," or "antigen-binding region," refers to a portion of an intact antibody that specifically binds to an antigen. An antigen-binding fragment can contain an antigen recognition site of an intact antibody (e.g., complementarity determining regions (CDRs) sufficient to specifically bind antigen). Examples of antigen-binding fragments of antibodies include, but are not limited to Fab, Fab', F(ab')2, and Fv fragments, linear antibodies, and single chain antibodies. An antigen-binding fragment of an antibody can be derived from any animal species, such as rodents (e.g., mouse, rat, or hamster) and humans or can be artificially produced.

The terms "anti-B7-H4 antibody," "B7-H4 antibody" and "antibody that binds to B7-H4" refer to an antibody that is capable of specifically binding B7-H4 with sufficient affinity such that the antibody is useful as a diagnostic and/or therapeutic agent in targeting B7-H4. As used herein, the terms "specifically binding," "immunospecifically binding," "immunospecifically recognizing," and "specifically recognizing" are analogous terms in the context of antibodies or antigen-binding fragments thereof. These terms indicate that the antibody or antigen-binding fragment thereof binds to an epitope via its antigen-binding domain and that the binding entails some complementarity between the antigen binding domain and the epitope. Accordingly, an antibody that "specifically binds" to human B7-H4 (SEQ ID NO:1) may also bind to B7-H4 from other species (e.g., cynomolgus monkey, mouse, and/or rat B7-H4) and/or B7-H4 proteins produced from other human alleles, but the extent of binding of an anti-B7-H4 antibody to an unrelated, non-B7-H4 protein (e.g., other B7 protein family members such as PD-L1) is less than about 10% of the binding of the antibody to B7-H4 as measured, e.g., by a radioimmunoassay (RIA).

A "monoclonal" antibody or antigen-binding fragment thereof refers to a homogeneous antibody or antigen-binding fragment population involved in the highly specific recognition and binding of a single antigenic determinant, or epitope. This is in contrast to polyclonal antibodies that typically include different antibodies directed against different antigenic determinants. The term "monoclonal" antibody or antigen-binding fragment thereof encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal" antibody or antigen-binding fragment thereof refers to such antibodies and antigen-binding fragments thereof made in any number of manners including but not limited to by hybridoma, phage selection, recombinant expression, and transgenic animals.

As used herein, the terms "variable region" or "variable domain" are used interchangeably and are common in the art. The variable region typically refers to a portion of an antibody, generally, a portion of a light or heavy chain, typically about the amino-terminal 110 to 120 amino acids or 110 to 125 amino acids in the mature heavy chain and about 90 to 115 amino acids in the mature light chain, which differ in sequence among antibodies and are used in the binding and specificity of a particular antibody for its particular antigen. The variability in sequence is concentrated in those regions called complementarity determining regions (CDRs) while the more highly conserved regions in the variable domain are called framework regions (FR). Without wishing to be bound by any particular mechanism or theory, it is believed that the CDRs of the light and heavy chains are primarily responsible for the interaction and specificity of the antibody with antigen. In certain embodiments, the variable region is a human variable region. In certain embodiments, the variable region is a rodent or murine variable region.

The terms "VL" and "VL domain" are used interchangeably to refer to the light chain variable region of an antibody.

The terms "VH" and "VH domain" are used interchangeably to refer to the heavy chain variable region of an antibody.

The term "Kabat numbering" and like terms are recognized in the art and refer to a system of numbering amino acid residues in the heavy and light chain variable regions of an antibody or an antigen-binding fragment thereof. In certain aspects, CDRs can be determined according to the Kabat numbering system (see, e.g., Kabat E A & Wu T T (1971) Ann NY Acad Sci 190: 382-391 and Kabat E A et al., (1991) Sequences of Proteins of Immunological Interest, Fifth Edition, U.S. Department of Health and Human Services, NIH Publication No. 91-3242). Using the Kabat numbering system, CDRs within an antibody heavy chain molecule are typically present at amino acid positions 31 to 35, which optionally can include one or two additional amino acids, following 35 (referred to in the Kabat numbering scheme as 35A and 35B) (CDR1), amino acid positions 50 to 65 (CDR2), and amino acid positions 95 to 102 (CDR3). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3).

In a specific embodiment, the CDRs of the antibodies described herein have been determined according to the Kabat numbering scheme.

Chothia refers instead to the location of the structural loops (Chothia and Lesk, J. Mol. Biol. 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software.

| Loop | Kabat | AbM | Chothia |
| --- | --- | --- | --- |
| L1 | L24-L34 | L24-L34 | L24-L34 |
| L2 | L50-L56 | L50-L56 | L50-L56 |
| L3 | L89-L97 | L89-L97 | L89-L97 |
| H1 | H31-H35B | H26-H35B (Kabat Numbering) | H26-H32..34 |
| H1 | H31-H35 | H26-H35 (Chothia Numbering) | H26-H32 |
| H2 | H50-H65 | H50-H58 | H52-H56 |
| H3 | H95-H102 | H95-H102 | H95-H102 |

As used herein, the terms "constant region" and "constant domain" are interchangeable and have their common meanings the art. The constant region is an antibody portion, e.g., a carboxyl terminal portion of a light and/or heavy chain which is not directly involved in binding of an antibody to antigen but which can exhibit various effector functions, such as interaction with the Fc receptor. The constant region of an immunoglobulin molecule generally has a more conserved amino acid sequence relative to an immunoglobulin variable domain. In certain aspects, an antibody or antigen-binding fragment comprises a constant region or portion thereof that is sufficient for antibody-dependent cell-mediated cytotoxicity (ADCC).

As used herein, the term "heavy chain" when used in reference to an antibody can refer to any distinct type, e.g., alpha (α), delta (δ), epsilon (ε), gamma (γ), and mu (μ), based on the amino acid sequence of the constant domain, which give rise to IgA, IgD, IgE, IgG, and IgM classes of antibodies, respectively, including subclasses of IgG, e.g., $IgG_1$, $IgG_2$, $IgG_3$, and $IgG_4$. Heavy chain amino acid sequences are well known in the art. In specific embodiments, the heavy chain is a human heavy chain. In specific embodiments, the heavy chain is a rodent or murine heavy chain.

As used herein, the term "light chain" when used in reference to an antibody can refer to any distinct type, e.g., kappa (κ) or lambda (λ) based on the amino acid sequence of the constant domains. Light chain amino acid sequences are well known in the art. In specific embodiments, the light chain is a human light chain. In specific embodiments, the light chain is a rodent or murine light chain.

The term "chimeric" antibodies or antigen-binding fragments thereof refers to antibodies or antigen-binding fragments thereof wherein the amino acid sequence is derived from two or more species. Typically, the variable region of both light and heavy chains corresponds to the variable region of antibodies or antigen-binding fragments thereof derived from one species of mammals (e.g. mouse, rat, rabbit, etc.) with the desired specificity, affinity, and capability while the constant regions are homologous to the sequences in antibodies or antigen-binding fragments thereof derived from another (usually human) to avoid eliciting an immune response in that species.

The term "humanized" antibody or antigen-binding fragment thereof refers to forms of non-human (e.g. murine) antibodies or antigen-binding fragments that are specific immunoglobulin chains, chimeric immunoglobulins, or fragments thereof that contain minimal non-human (e.g., murine) sequences. Typically, humanized antibodies or antigen-binding fragments thereof are human immunoglobulins in which residues from the complementary determining region (CDR) are replaced by residues from the CDR of a non-human species (e.g. mouse, rat, rabbit, hamster) that have the desired specificity, affinity, and capability ("CDR grafted") (Jones et al., Nature 321:522-525 (1986); Riechmann et al., Nature 332:323-327 (1988); Verhoeyen et al., Science 239:1534-1536 (1988)). In some instances, certain Fv framework region (FR) residues of a human immunoglobulin are replaced with the corresponding residues in an antibody or fragment from a non-human species that has the desired specificity, affinity, and capability. The humanized antibody or antigen-binding fragment thereof can be further modified by the substitution of additional residues either in the Fv framework region and/or within the non-human CDR residues to refine and optimize antibody or antigen-binding fragment thereof specificity, affinity, and/or capability. In general, the humanized antibody or antigen-binding fragment thereof will comprise variable domains containing all or substantially all of the CDR regions that correspond to the non-human immunoglobulin whereas all or substantially all of the FR regions are those of a human immunoglobulin consensus sequence. The humanized antibody or antigen-binding fragment thereof can also comprise at least a portion of an immunoglobulin constant region or domain (Fc), typically that of a human immunoglobulin. Examples of methods used to generate humanized antibodies are described in U.S. Pat. No. 5,225,539; Roguska et al., Proc. Natl. Acad. Sci., USA, 91(3):969-973 (1994), and Roguska el al., Protein Eng. 9(10):895-904 (1996). In some embodiments, a "humanized antibody" is a resurfaced antibody.

The term "human" antibody or antigen-binding fragment thereof means an antibody or antigen-binding fragment thereof having an amino acid sequence derived from a human immunoglobulin gene locus, where such antibody or antigen-binding fragment is made using any technique known in the art. This definition of a human antibody or antigen-binding fragment thereof includes intact or full-length antibodies and fragments thereof.

"Binding affinity" generally refers to the strength of the sum total of non-covalent interactions between a single binding site of a molecule (e.g., an antibody or antigen-binding fragment thereof) and its binding partner (e.g., an antigen). Unless indicated otherwise, as used herein, "binding affinity" refers to intrinsic binding affinity which reflects a 1:1 interaction between members of a binding pair (e.g., antibody or antigen-binding fragment thereof and antigen). The affinity of a molecule X for its partner Y can generally be represented by the dissociation constant ($K_D$). Affinity can be measured and/or expressed in a number of ways known in the art, including, but not limited to, equilibrium dissociation constant ($K_D$), and equilibrium association constant ($K_A$). The $K_D$ is calculated from the quotient of $k_{off}/k_{on}$, whereas $K_A$ is calculated from the quotient of $k_{on}/k_{off}$. $k_{on}$ refers to the association rate constant of, e.g., an antibody or antigen-binding fragment thereof to an antigen, and $k_{off}$ refers to the dissociation of, e.g., an antibody or antigen-binding fragment thereof from an antigen. The $k_{on}$ and $k_{off}$ can be determined by techniques known to one of ordinary skill in the art, such as BIAcore® or KinExA.

As used herein, an "epitope" is a term in the art and refers to a localized region of an antigen to which an antibody or antigen-binding fragment thereof can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In certain embodiments, the epitope to which an antibody or antigen-binding fragment thereof specifically binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligo-peptide scanning assays, and/or mutagenesis mapping (e.g., site-directed mutagenesis mapping). For X-ray crystallography, crystallization may be accomplished using any of the known methods in the art (e.g., Giegé R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303). Antibody/antigen-binding fragment thereof: antigen crystals can be studied using well known X-ray diffraction techniques and can be refined using computer software such as X-PLOR (Yale University, 1992, distributed by Molecular Simulations, Inc.; see, e.g., Meth Enzymol (1985) volumes 114 & 115, eds Wyckoff H W et al.; U.S. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al., (2000) Acta Crystallogr D Biol Crystallogr 56(Pt 10): 1316-1323). Mutagenesis mapping studies can be accomplished using any method known to one of skill in the art. See, e.g., Champe M et al., (1995) J Biol Chem 270: 1388-1394 and Cunningham B C & Wells J A (1989) Science 244: 1081-1085 for a description of mutagenesis techniques, including alanine scanning mutagenesis techniques.

A B7-H4 antibody that "binds to the same epitope" as a reference B7-H4 antibody refers to an antibody that binds to the same B7-H4 amino acid residues as the reference B7-H4 antibody. The ability of a B7-H4 antibody to bind to the same epitope as a reference B7-4 antibody is determined by a hydrogen/deuterium exchange assay (see Coales et al. Rapid Commun. Mass Spectrom. 2009; 23: 639-647).

An antibody is said to "competitively inhibit" binding of a reference antibody to a given epitope if it binds to the same epitope or an overlapping epitope of the reference antibody such that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cell or compositions include those which have been purified to a degree that they are no longer in a form in which they are found in nature. In some embodiments, an antibody, polynucleotide, vector, cell, or composition which is isolated is substantially pure. As used herein, "substantially pure" refers to material which is at least 50% pure (i.e., free from contaminants), at least 90% pure, at least 95% pure, at least 98% pure, or at least 99% pure.

The terms "polypeptide," "peptide," and "protein" are used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon antibodies, in certain embodiments, the polypeptides can occur as single chains or associated chains.

"Percent identity" refers to the extent of identity between two sequences (e.g., amino acid sequences or nucleic acid sequences). Percent identity can be determined by aligning two sequences, introducing gaps to maximize identity between the sequences. Alignments can be generated using programs known in the art. For purposes herein, alignment of nucleotide sequences can be performed with the blastn program set at default parameters, and alignment of amino acid sequences can be performed with the blastp program set at default parameters (see National Center for Biotechnology Information (NCBI) on the worldwide web, ncbi.nlm.nih.gov).

As used herein, the term "host cell" can be any type of cell, e.g., a primary cell, a cell in culture, or a cell from a cell line. In specific embodiments, the term "host cell" refers to a cell transfected with a nucleic acid molecule and the progeny or potential progeny of such a cell. Progeny of such a cell may not be identical to the parent cell transfected with the nucleic acid molecule, e.g., due to mutations or environmental influences that may occur in succeeding generations or integration of the nucleic acid molecule into the host cell genome.

The term "overexpression" of B7-H4 in a particular tumor, tissue, or cell sample refers to B7-H4 (a B7-H4 polypeptide or a nucleic acid encoding such a polypeptide) that is present at a level higher than that which is present in non-diseased tissue or cells of the same type or origin or other cells in the proximity of a tumor or cancer. Such overexpression can be caused, for example, by mutation, gene amplification, increased transcription, or increased translation.

The term "primary" antibody or antigen-binding fragment thereof herein refers to an antibody or fragment that binds specifically to the target antigen in a sample. A primary antibody is generally the first antibody used in an immunohistochemical (IHC) procedure. In one embodiment, the primary antibody is the only antibody used in an IHC procedure. The term "secondary" antibody or antigen-binding fragment thereof herein refers to an antibody or fragment that binds specifically to a primary antibody, thereby forming a bridge between the primary antibody and a subsequent reagent, if any. The secondary antibody is generally the second antibody used in an immunohistochemical procedure. The term "tertiary antibody" herein refers to an antibody that binds specifically to a secondary antibody, thereby forming a bridge between the secondary antibody and a subsequent reagent, if any.

A "sample" of the present invention is of biological origin. In preferred embodiments, the sample is a human sample, but animal samples may also be used in the practice of the invention. Non-limiting sources of a sample for use in the present invention include solid tissue, biopsy, ascites, aspirates, fluidic extracts, blood (including circulating tumor cells), plasma, serum, spinal fluid, lymph fluid, the external sections of the skin, respiratory, intestinal, and genitourinary tracts, tears, saliva, milk, tumors, organs, cell cultures and/or cell culture constituents, for example. A "cancerous sample" is a sample that contains a cancerous cell.

For the purposes herein, a "section" of a tissue sample refers to a single part or piece of a tissue sample, e.g., a thin slice of tissue or cells cut from a tissue sample. It is understood that multiple sections of tissue samples may be taken and subjected to analysis according to the present invention. In some cases, the selected portion or section of tissue comprises a homogeneous population of cells. In other cases, the selected portion comprises a region of tissue, e.g., the lumen as a non-limiting example. The selected portion can be as small as one cell or two cells, or could represent many thousands of cells, for example. In most cases, the collection of cells is important, and while the invention has been described for use in the detection of cellular components, the method may also be used for detecting non-cellular components of an organism (e.g., soluble components in the blood as a non-limiting example).

The word "label" when used herein refers to a detectable compound or composition which is conjugated directly or indirectly to the antibody so as to generate a "labeled" antibody. The label can be detectable by itself (e.g., radioisotope labels or fluorescent labels) or, in the case of an enzymatic label, can catalyze chemical alteration of a substrate compound or composition which is detectable.

The term "pharmaceutical formulation" refers to a preparation which is in such form as to permit the biological activity of the active ingredient to be effective, and which contains no additional components which are unacceptably toxic to a subject to which the formulation would be administered. The formulation can be sterile.

The terms "administer," "administering," "administration," and the like, as used herein, refer to methods that may be used to enable delivery of a drug, e.g., an anti-B7-H4 antibody or antigen-binding fragment thereof to the desired site of biological action (e.g., intravenous administration). Administration techniques that can be employed with the agents and methods described herein are found in e.g., Goodman and Gilman, *The Pharmacological Basis of Therapeutics*, current edition, Pergamon; and Remington's, *Pharmaceutical Sciences*, current edition, Mack Publishing Co., Easton, Pa.

As used herein, the terms "subject" and "patient" are used interchangeably. The subject can be an animal. In some embodiments, the subject is a mammal such as a non-human animal (e.g., cow, pig, horse, cat, dog, rat, mouse, monkey or other primate, etc.). In some embodiments, the subject is a human.

The term "therapeutically effective amount" refers to an amount of a drug, e.g., an anti-B7-H4 antibody or antigen-binding fragment thereof effective to treat a disease or disorder in a subject. In the case of cancer, the therapeutically effective amount of the drug can reduce the number of cancer cells; reduce the tumor size or burden; inhibit to some extent cancer cell infiltration into peripheral organs; inhibit to some extent tumor metastasis; inhibit, to some extent, tumor growth; relieve, to some extent one, or more of the symptoms associated with the cancer; and/or result in a favorable response such as increased progression-free survival (PFS), disease-free survival (DFS), overall survival (OS), complete response (CR), partial response (PR), or, in some cases, stable disease (SD), a decrease in progressive disease (PD), a reduced time to progression (TTP), or any combination thereof. To the extent the drug can prevent growth and/or kill existing cancer cells, it can be cytostatic and/or cytotoxic.

Terms such as "treating," "treatment," "to treat," "alleviating" and "to alleviate" refer to therapeutic measures that cure, slow down, lessen symptoms of, and/or halt progression of a pathologic condition or disorder. Thus, those in need of treatment include those already diagnosed with or suspected of having the disorder. In certain embodiments, a subject is successfully "treated" for cancer according to the methods of the present invention if the patient shows one or more of the following: a reduction in the number of or complete absence of cancer cells; a reduction in the tumor size, inhibition or an absence of cancer cell infiltration into peripheral organs including, for example, the spread of cancer into soft tissue and bone; inhibition of or an absence of tumor metastasis; inhibition or an absence of tumor growth; relief of one or more symptoms associated with the specific cancer; reduced morbidity and mortality; improvement in quality of life; reduction in tumorigenicity, tumorigenic frequency, or tumorigenic capacity, of a tumor; reduction in the number or frequency of cancer stem cells in a tumor; differentiation of tumorigenic cells to a non-tumorigenic state; increased progression-free survival (PFS), disease-free survival (DFS), overall survival (OS), complete response (CR), partial response (PR), stable disease (SD), a decrease in progressive disease (PD), a reduced time to progression (TTP), or any combination thereof.

The terms "cancer" and "cancerous" refer to or describe the physiological condition in mammals in which a population of cells are characterized by unregulated cell growth. Examples of cancer include, but are not limited to, gynecological cancers (e.g., breast cancer (including triple negative breast cancer, ductal carcinoma, ovarian cancer, and endometrial cancer), non-small cell lung cancer, pancreatic cancer, thyroid cancer, kidney cancer (e.g., renal cell carcinoma) and bladder cancer (e.g., urothelial cell carcinoma). The cancer can be a "cancer that expresses B7-H4" or a "B7-H4 expressing cancer." Such terms refer to a cancer comprising cells that express B7-H4. The cancer can be a solid tumor that expresses B7-H4. The cancer can be a primary tumor or may be advanced or metastatic cancer.

A "refractory" cancer is one that progresses even though an anti-tumor treatment, such as a chemotherapy, is administered to the cancer patient.

A "recurrent" cancer is one that has regrown, either at the initial site or at a distant site, after a response to initial therapy.

As used in the present disclosure and claims, the singular forms "a," "an," and "the" include plural forms unless the context clearly dictates otherwise.

It is understood that wherever embodiments are described herein with the language "comprising," otherwise analogous embodiments described in terms of "consisting of" and/or "consisting essentially of" are also provided. In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited are not changed by the presence of more than that which is recited, but excludes prior art embodiments Unless specifically stated or obvious from context, as used herein, the term "or" is understood to be inclusive. The term "and/or" as used in a phrase such as "A and/or B" herein is intended to include both "A and B," "A or B," "A," and "B." Likewise, the term "and/or" as used in a phrase such as "A, B, and/or C" is intended to encompass each of the following embodiments: A, B, and C; A, B, or C; A or C; A or B; B or C; A and B; B and C; A (alone); B (alone); and C (alone).

As used herein, the terms "about" and "approximately," when used to modify a numeric value or numeric range, indicate that deviations of 5% to 10% above and 5% to 10% below the value or range remain within the intended meaning of the recited value or range.

Any compositions or methods provided herein can be combined with one or more of any of the other compositions and methods provided herein.

Antibodies

In a specific aspect, provided herein are antibodies (e.g., monoclonal antibodies) and antigen-binding fragments thereof which specifically bind to B7-H4 (e.g., human B7-H4). The amino acid sequences for human B7-H4 is known in the art and also provided herein as represented by SEQ ID NO:1.

Human B7-H4:
(SEQ ID NO: 1)
MASLGQILFWSIISIIIILAGAIALIIGFGISGRHSITVTTVASAGNIGED

GILSCTFEPDIKLSDIVIQWLKEGVLGLVHEFKEGKDELSEQDEMFRGRTA

VFADQVIVGNASLRLKNVQLTDAGTYKCYIITSKGKGNANLEYKTGAFSMP

EVNVDYNASSETLRCEAPRWFPQPTATVVWASQVDQGANFSEVSNTSFELN

SENVTMKVVSVLYNVTINNTYSCMIENDIAKATGDIKVTESEIKRRSHLQL

LNSKASLCVSSFFAISWALLPLSPYLMLK

In certain embodiments, an anti-B7-H4 antibody or antigen-binding fragment thereof is an antibody disclosed in Table 1 or is an antibody or antigen-binding fragment thereof comprising the complementarity determining regions (CDRs), variable heavy chain and/or variable light chain, and/or heavy chain and/or light chain of an antibody disclosed in Table 1.

TABLE 1

Exemplary anti-B7-H4 antibodies

| Clone ID | Hybridoma VH/VL | Antibody Type | SEQ ID NOs | | | |
|---|---|---|---|---|---|---|
| | | | CDRs | VH | VL H | L |
| J511 | M6 | mIgG1 | 22-26, 29 | 6 | 9 89 | 19 |
| J512 | M6 | mIgG2a | 22-26, 29 | 6 | 9 16 | 19 |
| J517 | M6 De-N-gly (1), | mIgG2a | 22-25, 27, 29 | 6 | 10 16 | 30 |
| J518 | M6 De-N-gly (2) | mIgG2a | 22-25, 28, 29 | 6 | 11 16 | 31 |
| J513 | M11 | mIgG1 | 22-26, 29 | 7 | 9 90 | 19 |
| J514 | M11 | mIgG2a | 22-26, 29 | 7 | 9 17 | 19 |

TABLE 1-continued

Exemplary anti-B7-H4 antibodies

| Clone ID | Hybridoma VH/VL | Antibody Type | SEQ ID NOs CDRs | VH | VL | H | L |
|---|---|---|---|---|---|---|---|
| J519 | M11 - De-N-gly (1) | mIgG2a | 22-25, 27, 29 | 7 | 10 | 17 | 30 |
| J520 | M11 De-N-gly (2) | mIgG2a | 22-25, 28, 29 | 7 | 11 | 17 | 31 |
| J515 | M15 | mIgG1 | 22-26, 29 | 8 | 9 | 91 | 19 |
| J516 | M15 | mIgG2a | 22-26, 29 | 8 | 9 | 18 | 19 |
| J521 | M15 - De-N-gly (1) | mIgG2a | 22-25, 27, 29 | 8 | 10 | 18 | 30 |
| J522 | M15 De-N-gly (2) | mIgG2a | 22-25, 28 (29) | 8 | 11 | 18 | 31 |

In certain embodiments, an antibody or antigen-binding fragment thereof described herein specifically binds to human B7-H4 and comprises six CDRs listed in Table 2, i.e., the six CDRs of SEQ ID NO:22, SEQ ID NO:23, SEQ ID NO:24, SEQ ID NO:25, a sequence selected from the group consisting of SEQ ID NOs:26-28, and SEQ ID NO:29.

TABLE 2

CDR Amino Acid Sequences

| Description of CDR | CDR Amino Acid Sequence (SEQ ID NO) |
|---|---|
| VH-CDR1 | GFSLSTYG (SEQ ID NO: 22) |
| VH-CDR2 | WWNDD (SEQ ID NO: 23) |
| VH-CDR3 | VDGYYWYFDV (SEQ ID NO: 24) |
| VL-CDR1 | RSSQSIVHSNRNTYLE (SEQ ID NO: 25) |
| VL-CDR2 | NVSNRFS (SEQ ID NO: 26) |
| VL-CDR2, De-N-glycosylated (1) | NVANRFS (SEQ ID NO: 27) |
| VL-CDR2, De-N-glycosylated (2) | QVSNRFS (SEQ ID NO: 28) |
| VL-CDR3 | FQGSHVPLT (SEQ ID NO: 29) |

In certain embodiments, an antibody or antigen-binding fragment thereof described herein specifically binds to human B7-H4 and comprises a VH listed in Table 3, e.g., in combination with a VL.

TABLE 3

Variable Heavy Chain (VH) Amino Acid Sequences

| Description of VH | VH Amino Acid Sequence (SEQ ID NO) |
|---|---|
| M6 VH (J511 J512, J517, J518) | QVTLKESGPGILQPSQTLSLTCSFSGFSLSTYGLGVGWIRQP SGKGLDWLANIWWNDDKYYNSALKSRLTISKDTSNNQVF LKISSVDTADTGTYYCAQVDGYYWYFDVWGAGTTVTVSS (SEQ ID NO: 6) |
| M11 VH (J513, J514, J519, J520) | QVTLKESGPGILQPSQTLSLTCSLSGFSLSTYGLGVGWIRQP SGKGLGWLANIWWNDDKYYNSALKSRLTISKDTSNNQVF LKISSVDTADTGTYYCAQVDGYYWYFDVWGAGTTVTVSS (SEQ ID NO: 7) |
| M15 VH (J515, J516, J521, J522) | QVTLKESGPGILQSSQTLSLTCSFSGFSLSTYGLGVGWIRQP SGKGLDWLANIWWNDDKYYNSALKSRLTISKDTSNNQVF LKISSVDTADTGTYYCAQVDGYYWYFDVWGAGTTVTVSS (SEQ ID NO: 8) |

In certain embodiments, an antibody or antigen-binding fragment thereof described herein specifically binds to human B7-H4 and comprises a VL listed in Table 4, e.g., in combination with a VH.

TABLE 4

Variable Light Chain (VL) Amino Acid Sequences

| Description of VL | VL Amino Acid Sequence (SEQ ID NO) |
|---|---|
| M6, M11, M15 VL (J511-J516) | DVLMTQTPLSLPVSLGDQASISCRSSQSIVHSNRNTYLEWY LQKPGQSPKLLIYNVSNRFSGVPDRFSGSGSGTDFTLKISR VEAEDLGVYYCFQGSHVPLTFGAGTKLELK (SEQ ID NO: 9) |
| De-N-glycosylated VL (1) (J517, J519, J521) | DVLMTQTPLSLPVSLGDQASISCRSSQSIVHSNRNTYLEWY LQKPGQSPKLLIYNVANRFSGVPDRFSGSGSGTDFTLKISR VEAEDLGVYYCFQGSHVPLTFGAGTKLELK (SEQ ID NO: 10) |

TABLE 4-continued

Variable Light Chain (VL) Amino Acid Sequences

| Description of VL | VL Amino Acid Sequence (SEQ ID NO) |
|---|---|
| De-N-glycosylated VL (J518, J520, J522) | DVLMTQTPLSLPVSLGDQASISCRSSQSIVHSNRNTYLEWY LQKPGQSPKLLIYQVSNRFSGVPDRFSGSGSGTDFTLKISR VEAEDLGVYYCFQGSHVPLTFGAGTKLELK (SEQ ID NO: 11) |

In certain embodiments, an antibody or antigen-binding fragment thereof described herein specifically binds to human B7-H4 and comprises a VH listed in Table 3 and a VL of listed in Table 4. In certain embodiments, an antibody or antigen-binding fragment thereof described herein specifically binds to human B7-H4 and comprises a VH comprising or consisting of a sequence listed in Table 3 and a VL comprising or consisting of listed in Table 4.

In certain embodiments, an antibody or antigen-binding fragment thereof described herein specifically binds to human B7-H4, comprises a VH comprising a sequence at least 80% identical to a VH sequence in Table 3 and a VL comprising a sequence at least 80% identical to a VL sequence in Table 4. In certain embodiments, an antibody or antigen-binding fragment thereof described herein specifically binds to human B7-H4, comprises a VH comprising a sequence at least 85% identical to a VH sequence in Table 3 and a VL comprising a sequence at least 85% identical to a VL sequence in Table 4.

In certain embodiments, an antibody or antigen-binding fragment thereof described herein specifically binds to human B7-H4, comprises a VH consisting of a sequence at least 80% identical to a VH sequence in Table 3 and a VL consisting of a sequence at least 80% identical to a VL sequence in Table 4. In certain embodiments, an antibody or antigen-binding fragment thereof described herein specifically binds to human B7-H4, comprises a VH consisting of a sequence at least 85% identical to a VH sequence in Table 3 and a VL consisting of a sequence at least 85% identical to a VL sequence in Table 4.

In certain embodiments, an antibody or antigen-binding fragment thereof described herein specifically binds to human B7-H4, comprises a VH comprising a sequence at least 90% identical to a VH sequence in Table 3 and a VL comprising a sequence at least 90% identical to a VL sequence in Table 4. In certain embodiments, an antibody or antigen-binding fragment thereof described herein specifically binds to human B7-H4, comprises a VH comprising a sequence at least 95% identical to a VH sequence in Table 3 and a VL comprising a sequence at least 95% identical to a VL sequence in Table 4.

In certain embodiments, an antibody or antigen-binding fragment thereof described herein specifically binds to human B7-H4, comprises a VH comprising a sequence at least 96% identical to a VH sequence in Table 3 and a VL comprising a sequence at least 96% identical to a VL sequence in Table 4. In certain embodiments, an antibody or antigen-binding fragment thereof described herein specifically binds to human B7-H4, comprises a VH comprising a sequence at least 97% identical to a VH sequence in Table 3 and a VL comprising a sequence at least 97% identical to a VL sequence in Table 4. In certain embodiments, an antibody or antigen-binding fragment thereof described herein specifically binds to human B7-H4, comprises a VH comprising a sequence at least 98% identical to a VH sequence in Table 3 and a VL comprising a sequence at least 98% identical to a VL sequence in Table 4. In certain embodiments, an antibody or antigen-binding fragment thereof described herein specifically binds to human B7-H4, comprises a VH comprising a sequence at least 99% identical to a VH sequence in Table 3 and a VL comprising a sequence at least 99% identical to a VL sequence in Table 4.

In certain embodiments, an antibody or antigen-binding fragment thereof described herein specifically binds to human B7-H4, comprises a VH consisting of a sequence at least 96% identical to a VH sequence in Table 3 and a VL consisting of a sequence at least 96% identical to a VL sequence in Table 4. In certain embodiments, an antibody or antigen-binding fragment thereof described herein specifically binds to human B7-H4, comprises a VH consisting of a sequence at least 97% identical to a VH sequence in Table 3 and a VL consisting of a sequence at least 97% identical to a VL sequence in Table 4. In certain embodiments, an antibody or antigen-binding fragment thereof described herein specifically binds to human B7-H4, comprises a VH consisting of a sequence at least 98% identical to a VH sequence in Table 3 and a VL consisting of a sequence at least 98% identical to a VL sequence in Table 4. In certain embodiments, an antibody or antigen-binding fragment thereof described herein specifically binds to human B7-H4, comprises a VH consisting of a sequence at least 99% identical to a VH sequence in Table 3 and a VL consisting of a sequence at least 99% identical to a VL sequence in Table 4.

In certain aspects, an antibody or antigen-binding fragment thereof described herein is described by its VL domain alone, its VH domain alone, its 3 VL CDRs alone, or its 3 VH CDRs alone. See, for example, Rader C et al., (1998) PNAS 95: 8910-8915, which is incorporated herein by reference in its entirety, describing the humanization of the mouse anti-αvβ3 antibody by identifying a complementing light chain or heavy chain, respectively, from a human light chain or heavy chain library, resulting in humanized antibody variants having affinities as high or higher than the affinity of the original antibody. See also Clackson T et al., (1991) Nature 352: 624-628, which is incorporated herein by reference in its entirety, describing methods of producing antibodies that specifically bind a specific antigen by using a specific VL domain (or VH domain) and screening a library for the complementary VH domain (or VL domain). The screen produced 14 new partners for a specific VH domain and 13 new partners for a specific VL domain, which were strong binders, as determined by ELISA. See also Kim S J & Hong H J, (2007) J Microbiol 45: 572-577, which is incorporated herein by reference in its entirety, describing methods of producing antibodies that specifically bind a specific antigen by using a specific VH domain and screening a library (e.g., human VL library) for complementary VL domains; the selected VL domains in turn could be used to guide selection of additional complementary (e.g., human) VH domains.

In certain aspects, the CDRs of an antibody or antigen-binding fragment thereof can be determined according to the Chothia numbering scheme, which refers to the location of immunoglobulin structural loops (see, e.g., Chothia C & Lesk A M, (1987), J Mol Biol 196: 901-917; Al-Lazikani B et al., (1997) J Mol Biol 273: 927-948; Chothia C et al., (1992) J Mol Biol 227: 799-817; Tramontano A et al., (1990) J Mol Biol 215(1): 175-82; and U.S. Pat. No. 7,709,226). Typically, when using the Kabat numbering convention, the Chothia CDR-H1 loop is present at heavy chain amino acids 26 to 32, 33, or 34, the Chothia CDR-H2 loop is present at heavy chain amino acids 52 to 56, and the Chothia CDR-H3 loop is present at heavy chain amino acids 95 to 102, while the Chothia CDR-L1 loop is present at light chain amino acids 24 to 34, the Chothia CDR-L2 loop is present at light chain amino acids 50 to 56, and the Chothia CDR-L3 loop is present at light chain amino acids 89 to 97. The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34).

In certain aspects, provided herein are antibodies and antigen-binding fragments thereof that specifically bind to B7-H4 (e.g., human B7-H4) and comprise the Chothia VH and VL CDRs of an antibody. In certain embodiments, antibodies or antigen-binding fragments thereof that specifically bind to B7-H4 (e.g., human B7-H4) and comprise one or more CDRs, in which the Chothia and Kabat CDRs have the same amino acid sequence. In certain embodiments, provided herein are antibodies and antigen-binding fragments thereof that specifically bind to B7-H4 (e.g., human B7-H4) and comprise combinations of Kabat CDRs and Chothia CDRs.

In certain aspects, the CDRs of an antibody or antigen-binding fragment thereof can be determined according to the IMGT numbering system as described in Lefranc M-P, (1999) The Immunologist 7: 132-136 and Lefranc M-P et al., (1999) Nucleic Acids Res 27: 209-212. According to the IMGT numbering scheme, VH-CDR1 is at positions 26 to 35, VH-CDR2 is at positions 51 to 57, VH-CDR3 is at positions 93 to 102, VL-CDR1 is at positions 27 to 32, VL-CDR2 is at positions 50 to 52, and VL-CDR3 is at positions 89 to 97. In a particular embodiment, provided herein are antibodies and antigen-binding fragments thereof that specifically bind to B7-H4 (e.g., human B7-H4) and comprise the IMGT VH and VL CDRs of an antibody listed in Tables 3 and 4, for example, as described in Lefranc M-P (1999) supra and Lefranc M-P et al., (1999) supra).

In certain aspects, the CDRs of an antibody or antigen-binding fragment thereof can be determined according to MacCallum R M et al., (1996) J Mol Biol 262: 732-745. See also, e.g., Martin A. "Protein Sequence and Structure Analysis of Antibody Variable Domains," in *Antibody Engineering*, Kontermann and Dübel, eds., Chapter 31, pp. 422-439, Springer-Verlag, Berlin (2001). In a particular embodiment, provided herein are antibodies or antigen-binding fragments thereof that specifically bind to B7-H4 (e.g., human B7-H4) are determined by the method in MacCallum R M et al.

In certain aspects, the CDRs of an antibody or antigen-binding fragment thereof can be determined according to the AbM numbering scheme, which refers AbM hypervariable regions which represent a compromise between the Kabat CDRs and Chothia structural loops, and are used by Oxford Molecular's AbM antibody modeling software (Oxford Molecular Group, Inc.). In a particular embodiment, provided herein are antibodies or antigen-binding fragments thereof that specifically bind to B7-H4 (e.g., human B7-H4) are determined by the AbM numbering scheme.

In certain embodiments, an antibody or antigen-binding fragment thereof described herein specifically binds to human B7-H4 and comprises a heavy chain listed in Table 5, e.g., in combination with a light chain.

TABLE 5

Heavy Chain Amino Acid Sequences

| Description of Heavy Chain | Heavy Chain Amino Acid Secuence (SEQ ID NO) |
|---|---|
| M6 H (J511) | QVTLKESGPGILQPSQTLSLTCSFSGFSLSTYGLGVGWIRQP SGKGLDWLANIWWNDDKYYNSALKSRLTISKDTSNNQVF LKISSVDTADTGTYYCAQVDGYYWYFDVWGAGTTVTVSS AKTTPPSVYPLAPGSAAQTNSMVTLGCLVKGYFPEPVTVT WNSGSLSSGVHTFPAVLESDLYTLSSSVTVPSSPRPSETVTC NVAHPASSTKVDKKIVPRDCGCKPCICTVPEVSSVFIFPPKP KDVLTITLTPKVTCVVVDISKDDPEVQFSWFVDDVEVHTA QTQPREEQFNSTFRSVSELPIMHQDWLNGKEFKCRVNSAA FPAPIEKTISKTKGRPKAPQVYTIPPPKEQMAKDKVSLTCMI TDFFPEDITVEWQWNGQPAENYKNTQPIMNTNGSYFVYSK LNVQKSNWEAGNTFTCSVLHEGLHNHHTEKSLSHSPGK (SEQ ID NO: 89) |
| M6 H (J512, J517, J518) | QVTLKESGPGILQPSQTLSLTCSFSGFSLSTYGLGVGWIRQP SGKGLDWLANIWWNDDKYYNSALKSRLTISKDTSNNQVF LKISSVDTADTGTYYCAQVDGYYWYFDVWGAGTTVTVSS AKTTPPSVYPLAPGSAAQTNSMVTLGCLVKGYFPEPVTVT WNSGSLSSGVHTFPAVLESDLYTLSSSVTVPSSPRPSETVTC NVAHPASSTKVDKKIVPRDCGCKPCICTVPEVSSVFIFPPKI KDVLMISLSPIVTCVVVDVSEDDPDVQISWFVNNVEVHTA QTQTHREDYNSTLRVVSALPIQHQDWMSGKEFKCKVNNK DLPAPIERTISKPKGSVRAPQVYVLPPPEEEMTKKQVTLTC MVTDFMPEDIYVEWTNNGKTELNYKNTEPVLDSDGSYFM YSKLRVEKKNWVERNSYSCSVVHEGLHNHHTTKSFSRTPG K (SEQ ID NO. 16) |

TABLE 5-continued

Heavy Chain Amino Acid Sequences

| Description of Heavy Chain | Heavy Chain Amino Acid Sequence (SEQ ID NO) |
| --- | --- |
| M11 H (J513) | QVTLKESGPGILQPSQTLSLTCSLSGFSLSTYGLGVGWIRQP SGKGLGWLANIWWNDDKYYNSALKSRLTISKDTSNNQVF LKISSVDTADTGTYYCAQVDGYYWYFDVWGAGTTVTVSS AKTTPPSVYPLAPGSAAQTNSMVTLGCLVKGYFPEPVTVT WNSGSLSSGVHTFPAVLESDLYTLSSSVTVPSSPRPSETVTC NVAHPASSTKVDKKIVPRDCGCKPCICTVPEVSSVFIFPPKP KDVLTITLTPKVTCVVVDISKDDPEVQFSWFVDDVEVHTA QTQPREEQFNSTFRSVSELPIMHQDWLNGKEFKCRVNSAA FPAPIEKTISKTKGRPKAPQVYTIPPPKEQMAKDKVSLTCMI TDFFPEDITVEWQWNGQPAENYKNTQPIMNTNGSYFVYSK LNVQKSNWEAGNTFTCSVLHEGLHNHHTEKSLSHSPGK (SEQ ID NO: 90) |
| M11 H (J514, J519, J520) | QVTLKESGPGILQPSQTLSLTCSLSGFSLSTYGLGVGWIRQP SGKGLGWLANIWWNDDKYYNSALKSRLTISKDTSNNQVF LKISSVDTADTGTYYCAQVDGYYWYFDVWGAGTTVTVSS AKTTPPSVYPLAPGSAAQTNSMVTLGCLVKGYFPEPVTVT WNSGSLSSGVHTFPAVLESDLYTLSSSVTVPSSPRPSETVTC NVAHPASSTKVDKKIVPRDCGCKPCICTVPEVSSVFIFPPKI KDVLMISLSPIVTCVVVDVSEDDPDVQISWFVNNVEVHTA QTQTHREDYNSTLRVVSALPIQHQDWMSGKEFKCKVNNK DLPAPIERTISKPKGSVRAPQVYVLPPPEEEMTKKQVTLTC MVTDFMPEDIYVEWTNNGKTELNYKNTEPVLDSDGSYFM YSKLRVEKKNWVERNSYSCSVVHEGLHNHHTTKSFSRTPG K (SEQ ID NO: 17) |
| M15 H (J515) | QVTLKESGPGILQSSQTLSLTCSFSGFSLSTYGLGVGWIRQP SGKGLGWLANIWWNDDKYYNSALKSRLTISKDTSNNQVF LKISSVDTADTGTYYCAQVDGYYWYFDVWGAGTTVTVSS AKTTPPSVYPLAPGSAAQTNSMVTLGCLVKGYFPEPVTVT WNSGSLSSGVHTFPAVLESDLYTLSSSVTVPSSPRPSETVTC NVAHPASSTKVDKKIVPRDCGCKPCICTVPEVSSVFIFPPKP KDVLTITLTPKVTCVVVDISKDDPEVQFSWFVDDVEVHTA QTQPREEQFNSTFRSVSELPIMHQDWLNGKEFKCRVNSAA FPAPIEKTISKTKGRPKAPQVYTIPPPKEQMAKDKVSLTCMI TDFFPEDITVEWQWNGQPAENYKNTQPIMNTNGSYFVYSK LNVQKSNWEAGNTFTCSVLHEGLHNHHTEKSLSHSPGK (SEQ ID NO: 91) |
| M15 H (J516, J521, J522) | QVTLKESGPGILQSSQTLSLTCSFSGFSLSTYGLGVGWIRQP SGKGLDWLANIWWNDDKYYNSALKSRLTISKDTSNNQVF LKISSVDTADTGTYYCAQVDGYYWYFDVWGAGTTVTVSS AKTTPPSVYPLAPGSAAQTNSMVTLGCLVKGYFPEPVTVT WNSGSLSSGVHTFPAVLESDLYTLSSSVTVPSSPRPSETVTC NVAHPASSTKVDKKIVPRDCGCKPCICTVPEVSSVFIFPPKI KDVLMISLSPIVTCVVVDVSEDDPDVQISWFVNNVEVHTA QTQTHREDYNSTLRVVSALPIQHQDWMSGKEFKCKVNNK DLPAPIERTISKPKGSVRAPQVYVLPPPEEEMTKKQVTLTC MVTDFMPEDIYVEWTNNGKTELNYKNTEPVLDSDGSYFM YSKLRVEKKNWVERNSYSCSVVHEGLHNHHTTKSFSRTPG K (SEQ ID NO. 18) |

In certain embodiments, an antibody or antigen-binding fragment thereof described herein specifically binds to human B7-H4 and comprises a light chain listed in Table 6, e.g., in combination with a heavy chain.

TABLE 6

Light Chain Amino Acid Sequences

| Description of Light Chain | Light Chain Amino Acid Sequence (SEQ ID NO) |
| --- | --- |
| M6, M11, M15 L (J511 to J516) | DVLMTQTPLSLPVSLGDQASISCRSSQSIVHSNRNTYLEWY LQKPGQSPKLLIYNVSNRFSGVPDRFSGSGSGTDFTLKISRV EAEDLGVYYCFQGSHVPLTFGAGTKLELKRADAAPTVSIFP PSSEQLTSGGASVVCFLNNFYPKDINVKWKIDGSERQNGV LNSWTDQDSKDSTYSMSSTLTLTKDEYERHNSYTCEATHK TSTSPIVKSFNRNEC (SEQ ID NO: 19) |

TABLE 6-continued

Light Chain Amino Acid Sequences

| Description of Light Chain | Light Chain Amino Acid Sequence (SEQ ID NO) |
|---|---|
| De-N-glycosylated L (1) (J517, J519, J521) | DVLMTQTPLSLPVSLGDQASISCRSSQSIVHSNRNTYLEWY LQKPGQSPKLLIYNVANRFSGVPDRFSGSGSGTDFTLKISR VEAEDLGVYYCFQGSHVPLTFGAGTKLELKRADAAPTVSI FPPSSEQLTSGGASVVCFLNNFYPKDINVKWKIDGSERQNG VLNSWTDQDSKDSTYSMSSTLTLTKDEYERHNSYTCEATH KTSTSPIVKSFNRNEC (SEQ ID NQ: 30) |
| De-N-glycosylated L (2) (J518, J520, J522) | DVLMTQTPLSLPVSLGDQASISCRSSQSIVHSNRNTYLEWY LQKPGQSPKLLIYQVSNRFSGVPDRFSGSGSGTDFTLKISRV EAEDLGVYYCFQGSHVPLTFGAGTKLELKRADAAPTVSIFP PSSEQLTSGGASVVCFLNKFYPKDINVKWKIDGSERQNGV LNSWTDQDSKDSTYSMSSTLTLTKDEYERHNSYTCEATHK TSTSPIVKSFNRNEC (SEQ ID NO: 31) |

In certain embodiments, an antibody or antigen-binding fragment thereof described herein specifically binds to human B7-H4 and comprises a heavy chain listed in Table 5 and a light chain listed in Table 6.

In specific aspects, provided herein are antibodies that comprise a heavy chain and a light chain. With respect to the heavy chain in a specific embodiment, the heavy chain of an antibody described herein can be an alpha (α), delta (δ), epsilon (ε), gamma (γ) or mu (μ) heavy chain. In a particular embodiment, an antibody described herein, which immunospecifically binds to B7-H4 (e.g., human B7-H4), comprises a heavy chain wherein the amino acid sequence of the VH domain comprises an amino acid sequence set forth in Table 3 and wherein the constant region of the heavy chain comprises the amino acid sequence of a murine IgG2a heavy chain constant region.

In a particular embodiment, an antibody described herein, which immunospecifically binds to B7-H4 (e.g., human B7-H4), comprises a heavy chain wherein the amino acid sequence of the VH domain comprises an amino acid sequence set forth in Table 3 and wherein the constant region of the heavy chain comprises the amino acid sequence of SEQ ID NO:87:

(SEQ ID NO: 87)
AKTTPPSVYPLAPGSAAQTNSMVTLGCLVKGYFPEPVTVTWNSGSLSSGVH

TFPAVLESDLYTLSSSVTVPSSPRPSETVTCNVAHPASSTKVDKKIVPRDC

GCKPCICTVPEVSSVFIFPPKIKDVLMISLSPIVTCVVVDVSEDDPDVQIS

WFVNNVEVHTAQTQTHREDYNSTLRVVSALPIQHQDWMSGKEFKCKVNNKD

LPAPIERTISKPKGSVRAPQVYVLPPPEEEMTKKQVTLTCMVTDFMPEDIY

VEWTNNGKTELNYKNTEPVLDSDGSYFMYSKLRVEKKNWVERNSYSCSVVH

EGLHNHHTTKSFSRTPGK

In a particular embodiment, an antibody described herein, which immunospecifically binds to B7-H4 (e.g., human B7-H4), comprises a heavy chain wherein the amino acid sequence of the VH domain comprises an amino acid sequence set forth in Table 3 and wherein the constant region of the heavy chain comprises the amino acid sequence of a murine IgG1 heavy chain constant region.

In a particular embodiment, an antibody described herein, which immunospecifically binds to B7-H4 (e.g., human B7-H4), comprises a heavy chain wherein the amino acid sequence of the VH domain comprises an amino acid sequence set forth in Table 3 and wherein the constant region of the heavy chain comprises the amino acid sequence of SEQ ID NO:92:

(SEQ ID NO: 92)
AKTTPPSVYPLAPGSAAQTNSMVTLGCLVKGYFPEPVTVTWNSGSLSSGVH

TFPAVLESDLYTLSSSVTVPSSPRPSETVTCNVAHPASSTKVDKKIVPRDC

GCKPCICTVPEVSSVFIFPPKPKDVLTITLTPKVTCVVVDISKDDPEVQFS

WFVDDVEVHTAQTQPREEQFNSTFRSVSELPIMHQDWLNGKEFKCRVNSAA

FPAPIEKTISKTKGRPKAPQVYTIPPPKEQMAKDKVSLTCMITDFFPEDIT

VEWQWNGQPAENYKNTQPIMNTNGSYFVYSKLNVQKSNWEAGNTFTCSVLH

EGLHNHHTEKSLSHSPGK

With respect to the light chain, in a specific embodiment, the light chain of an antibody described herein is a kappa light chain or a lamda light chain. In a particular embodiment, an antibody described herein, which immunospecifically binds to B7-H4 (e.g., human B7-H4), comprises a light chain wherein the amino acid sequence of the VL domain comprises an amino acid sequence set forth in Table 4 and wherein the constant region of the heavy chain comprises the amino acid sequence of SEQ ID NO:88:

(SEQ ID NO: 88)
RADAAPTVSIFPPSSEQLTSGGASVVCFLNNFYPKDINVKWKIDGSERQNG

VLNSWTDQDSKDSTYSMSSTLTLTKDEYERHNSYTCEATHKTSTSPIVKSF

NRNEC.

In another specific embodiment, an antibody described herein, which immunospecifically binds to B7-H4 (e.g., human B7-H4) comprises (i) a heavy chain wherein the amino acid sequence of the VH domain comprises an amino acid sequence set forth in Table 3 and wherein the constant region of the heavy chain comprises the amino acid sequence of SEQ ID NO:87 and (ii) a light chain wherein the amino acid sequence of the VL domain comprises an amino acid sequence set forth in Table 4 and wherein the constant region of the heavy chain comprises the amino acid sequence of SEQ ID NO:88.

In another specific embodiment, an antibody described herein, which immunospecifically binds to B7-H4 (e.g., human B7-H4) comprises (i) a heavy chain wherein the amino acid sequence of the VH domain comprises an amino acid sequence set forth in Table 3 and wherein the constant region of the heavy chain comprises the amino acid sequence of SEQ ID NO:92 and (ii) a light chain wherein the amino acid sequence of the VL domain comprises an amino acid sequence set forth in Table 4 and wherein the constant region of the heavy chain comprises the amino acid sequence of SEQ ID NO:88.

In a specific embodiment, an antibody described herein, which immunospecifically binds to B7-H4 (e.g., human B7-H4) comprises a VH domain and a VL domain comprising any amino acid sequence described herein, and wherein the constant regions comprise the amino acid sequences of the constant regions of an IgG, IgE, IgM, IgD, IgA, or IgY immunoglobulin molecule, or a murine IgG, IgE, IgM, IgD, or IgA immunoglobulin molecule. In another specific embodiment, an antibody described herein, which immunospecifically binds to B7-H4 (e.g., human B7-H4) comprises a VH domain and a VL domain comprising any amino acid sequence described herein, and wherein the constant regions comprise the amino acid sequences of the constant regions of an IgG, IgE, IgM, IgD, IgA, or IgY immunoglobulin molecule, any class (e.g., $IgG_1$, $IgG_2$, $IgG_3$, $IgG_4$, $IgA_1$, and $IgA_2$), or any subclass (e.g., $IgG_{2a}$ and $IgG_{2b}$) of immunoglobulin molecule. In a particular embodiment, the constant regions comprise the amino acid sequences of the constant regions of a murine IgG, IgE, IgM, IgD, or IgA, immunoglobulin molecule, any class (e.g., $IgG_1$, $IgG_2$, and $IgG_3$), or any subclass (e.g., $IgG_{2a}$ and $IgG_{2b}$) of immunoglobulin molecule. In a particular embodiment, an antibody described herein, which immunospecifically binds to B7-H4 (e.g., human B7-H4) comprises a VH domain and a VL domain comprising any amino acid sequence described herein and murine constant domains. In a particular embodiment, an antibody described herein, which immunospecifically binds to B7-H4 (e.g., human B7-H4) comprises a VH domain and a VL domain comprising any amino acid sequence described herein and rabbit constant domains.

In specific embodiments, an antibody or antigen-binding fragment thereof comprises the VH and VL sequences of the amino acid sequences of SEQ ID NOs:6 and 9, respectively. In specific embodiments, the antibody or antigen-binding fragment thereof in an engineered variant of an antibody or antigen-binding fragment thereof comprising the VH and VL sequences of the amino acid sequences of SEQ ID NOs:6 and 9, wherein the engineering removes one or more glycosylation sites, e.g., in one or more CDRs (e.g., VL-CDR2). In specific embodiments, an antibody or antigen-binding fragment thereof comprises the VH and VL sequences of the amino acid sequences of SEQ ID NOs:6 and 10, respectively. In specific embodiments, an antibody or antigen-binding fragment thereof comprises the VH and VL sequences of the amino acid sequences of SEQ ID NOs:6 and 11, respectively. In specific embodiments, the antibody or antigen-binding fragment thereof (e.g., an antibody or antigen-binding fragment thereof comprising a VH of SEQ ID NO:6 and a VL of SEQ ID NO:9, 10, or 11) further comprises the constant domain of a murine $IgG_1$ heavy chain (e.g., J511). In specific embodiments, the antibody or antigen-binding fragment thereof (e.g., an antibody or antigen-binding fragment thereof comprising a VH of SEQ ID NO:6 and a VL of SEQ ID NO:9, 10, or 11) further comprises the constant domain of a murine $IgG_{2a}$ heavy chain (e.g., J512).

In specific embodiments, an antibody or antigen-binding fragment thereof comprises the VH and VL sequences of the amino acid sequences of SEQ ID NOs:7 and 9, respectively. In specific embodiments, the antibody or antigen-binding fragment thereof in an engineered variant of an antibody or antigen-binding fragment thereof comprising the VH and VL sequences of the amino acid sequences of SEQ ID NOs:7 and 9, wherein the engineering removes one or more glycosylation sites, e.g., in one or more CDRs (e.g., VL-CDR2). In specific embodiments, an antibody or antigen-binding fragment thereof comprises the VH and VL sequences of the amino acid sequences of SEQ ID NOs:7 and 10, respectively. In specific embodiments, an antibody or antigen-binding fragment thereof comprises the VH and VL sequences of the amino acid sequences of SEQ ID NOs:7 and 11, respectively. In specific embodiments, the antibody or antigen-binding fragment thereof (e.g., an antibody or antigen-binding fragment thereof comprising a VH of SEQ ID NO:7 and a VL of SEQ ID NO:9, 10, or 11) further comprises the constant domain of a murine $IgG_1$ heavy chain (e.g., J513). In specific embodiments, the antibody or antigen-binding fragment thereof (e.g., an antibody or antigen-binding fragment thereof comprising a VH of SEQ ID NO:7 and a VT of SEQ ID NO-9, 10, or 11) further comprises the constant domain of a murine $IgG_{2a}$ heavy chain (e.g., J514).

In specific embodiments, an antibody or antigen-binding fragment thereof comprises the VH and VL sequences of the amino acid sequences of SEQ ID NOs:8 and 9, respectively. In specific embodiments, the antibody or antigen-binding fragment thereof in an engineered variant of an antibody or antigen-binding fragment thereof comprising the VH and VL sequences of the amino acid sequences of SEQ ID NOs:8 and 9, wherein the engineering removes one or more glycosylation sites, e.g., in one or more CDRs (e.g., VL-CDR2). In specific embodiments, an antibody or antigen-binding fragment thereof comprises the VH and VL sequences of the amino acid sequences of SEQ ID NOs:8 and 10, respectively. In specific embodiments, an antibody or antigen-binding fragment thereof comprises the VH and VL sequences of the amino acid sequences of SEQ ID NOs:8 and 11, respectively. In specific embodiments, the antibody or antigen-binding fragment thereof (e.g., an antibody or antigen-binding fragment thereof comprising a VH of SEQ ID NO:8 and a VL of SEQ ID NO:9, 10, or 11) further comprises the constant domain of a murine $IgG_1$ heavy chain (e.g., J515). In specific embodiments, the antibody or antigen-binding fragment thereof (e.g., an antibody or antigen-binding fragment thereof comprising a VH of SEQ ID NO:8 and a VL of SEQ ID NO:9, 10, or 11) further comprises the constant domain of a murine $IgG_{2a}$ heavy chain (e.g., J516).

In specific embodiments, an antibody or antigen-binding fragment thereof (i) comprises the CDR sequences of M6 (e.g., the amino acid sequences of SEQ ID NOs:22-26 and 29), (ii) the VH and VL sequences of M6 or a De-N-glycosylated variant thereof (e.g., a VH comprising the amino acid sequence of SEQ ID NO:6 and a VL comprising the amino acid sequence of SEQ ID NO:9, 10, or 11), (iii) the heavy and light chain sequences of murine IgG2a M6 or a De-N-glycosylated variant thereof (e.g., a heavy chain comprising the amino acid sequence of SEQ ID NO:16 and a light chain comprising the amino acid sequence of SEQ ID NO:19, 30, or 31) or (iv) the heavy and light chain sequences of murine IgG1 M6 (e.g., a heavy chain comprising the amino acid sequence of SEQ ID NO:89 and a light chain comprising the amino acid sequence of SEQ ID NO:19).

In specific embodiments, an antibody or antigen-binding fragment thereof (i) comprises the CDR sequences of M11 (e.g., the amino acid sequences of SEQ ID NOs:22-25, 27, and 29), (ii) the VH and VL sequences of M11 or a De-N-glycosylated variant thereof (e.g., a VH comprising the amino acid sequence of SEQ ID NO:7 and a VL comprising the amino acid sequence of SEQ ID NO:9, 10, or 11), (iii) the heavy and light chain sequences of murine IgG2a M11 or a De-N-glycosylated variant thereof (e.g., a heavy chain comprising the amino acid sequence of SEQ ID NO:17 and a light chain comprising the amino acid sequence of SEQ ID NO:19, 30, or 31), or (iv) the heavy and light chain sequences of murine IgG1 M11 (e.g., a heavy chain comprising the amino acid sequence of SEQ ID NO:90 and a light chain comprising the amino acid sequence of SEQ ID NO:19).

In specific embodiments, an antibody or antigen-binding fragment thereof (i) comprises the CDR sequences of M15 (e.g., the amino acid sequences of SEQ ID NOs:22-25, 28, and 29), (ii) the VH and VL sequences of M15 or a De-N-glycosylated variant thereof (e.g., a VH comprising the amino acid sequence of SEQ ID NO:8 and a VL comprising the amino acid sequence of SEQ ID NO:9, 10, or 11), (iii) the heavy and light chain sequences of murine IgG2a M15 or a De-N-glycosylated variant thereof (e.g., a heavy chain comprising the amino acid sequence of SEQ ID NO:18 and a light chain comprising the amino acid sequence of SEQ ID NO:19, 30, or 31) or (iv) the heavy and light chain sequences of murine IgG1 M15 (e.g., a heavy chain comprising the amino acid sequence of SEQ ID NO:91 and a light chain comprising the amino acid sequence of SEQ ID NO:19).

In another particular embodiment, an antibody or antigen-binding fragment thereof described herein, which immunospecifically binds to B7-H4 (e.g., human B7-H4), comprises a heavy chain and a light chain, wherein (i) the heavy chain comprises a VH domain comprising the VH CDR1, VH CDR2, and VH CDR3 amino acid sequences of an antibody listed in Table 1 (e.g., SEQ ID NOs:22-24); (ii) the light chain comprises a VL domain comprising the VL CDR1, VL CDR2, and VL CDR3 amino acid sequences of the same antibody listed in Table 1 (e.g., SEQ ID NOs:25, 26, and 29, 25, 27, and 29, or 25, 28, and 29), (iii) the heavy chain further comprises a murine IgG1 constant domain (e.g. comprising the amino acid sequence of SEQ ID NO:92) or a murine IgG2a constant domain (e.g. comprising the amino acid sequence of SEQ ID NO:87); and (iv) the light chain further comprises a murine kappa constant domain (e.g., comprising the amino acid sequence of SEQ ID NO:88).

In another particular embodiment, an antibody or antigen-binding fragment thereof described herein, which immunospecifically binds to B7-H4 (e.g., human B7-H4), comprises a heavy chain and a light chain, wherein (i) the heavy chain comprises a VH domain comprising the amino acid sequence of an antibody listed in Table 1 (e.g., SEQ ID NOs:6-8); (ii) the light chain comprises a VL domain comprising the amino acid sequence of the same antibody listed in Table 1 (e.g., SEQ ID NOs:9-11); (iii) the heavy chain further comprises a murine IgG1 constant domain (e.g. comprising the amino acid sequence of SEQ ID NO:92) or a murine IgG2a constant domain (e.g. comprising the amino acid sequence of SEQ ID NO:87); and (iv) the light chain further comprises a murine kappa constant domain (e.g., comprising the amino acid sequence of SEQ ID NO:88).

In certain embodiments, an antibody or antigen-binding fragment thereof described herein, which specifically binds to B7-H4 (e.g., human B7-H4), comprises one, two, or more VH framework regions (FRs) having the amino acid sequences described herein for an antibody set forth in Table 7 (e.g., SEQ ID NOs:38-49). In some embodiments, an antibody or antigen-binding fragment thereof described herein, which specifically binds to B7-H4 (e.g., human B7-H4), comprises one, two, or more VL framework regions (FRs) having the amino acid sequences described herein for an antibody set forth in Table 7 (e.g., SEQ ID NOs:50-53). In specific embodiments, an antibody or antigen-binding fragment thereof described herein, which specifically binds to B7-H4 (e.g., human B7-H4), comprises one, two, or more VH framework regions having the amino acid sequences described herein for an antibody set forth in Table 7, supra, and one, two, or more VL framework regions having the amino acid sequences described herein for the same antibody set forth in Table 7 (e.g., SEQ ID NOs:38-41 and 50-53; SEQ ID NOs:42-45 and 50-53; or SEQ ID NOs:46-49 and 50-53).

TABLE 7

Framework Amino Acid Sequences

| Hybridoma VH/VL | FR1 (SEQ ID NO) | FR2 (SEQ ID NO) | FR3 (SEQ ID NO) | FR4 (SEQ ID NO) |
| --- | --- | --- | --- | --- |
| M6 VH | QVTLKESGP GILQPSQTLS LTCSFS (SEQ ID NO: 38) | GVGWIRQPSG KGLDWLANI (SEQ ID NO: 39) | KYYNSALKSRLTISKD TSNNQVFLKISSVDTA DTGTYYCAQ (SEQ ID NO:40) | WGAGTTVTV SS (SEQ ID NO: 41) |
| M11 VH | QVTLKESGP GILQPSQTLS LTCSLS (SEQ ID NO: 42) | GVGWIRQPSG KGLGWLANI (SEQ ID NO: 43) | KYYNSALKSRLTISKD TSNNQVFLKISSVDTA DTGTYYCAQ (SEQ ID NO: 44) | WGAGTTVTV SS (SEQ ID NO: 45) |
| M15 VH | QVTLKESGP GILQSSQTLS LTCSFS (SEQ ID NO: 46) | GVGWIRQPSG KGLDWLANI (SEQ ID NO: 47) | KYYNSALKSRLTISKD TSNNQVFLKISSVDTA DTGTYYCAQ (SEQ ID NO: 48) | WGAGTTVTV SS (SEQ ID NO: 49) |
| M6, M11, M15 VL | DVLMTQTPL SLPVSLGDQ ASISC (SEQ ID NO: 50) | YLQKPGQSPK LLIY (SEQ ID NO: 51) | GVPDRFSGSGSGTDFT LKISRVEAEDLGVYY C (SEQ ID NO: 52) | FGAGTKLELK (SEQ ID NO: 53) |

In certain embodiments, an antibody or antigen-binding fragment thereof described herein, which specifically binds to B7-H4 (e.g., human B7-H4), comprises VH framework regions (FRs) having at least 70%, at least 75%, at least 80%, at least 85%, at least 90%, at least 95%, or at least 98% sequence identity to the VH framework regions described herein in Table 7. In certain embodiments, an antibody or antigen-binding fragment thereof described herein, which specifically binds to B7-H4 (e.g., human B7-H4), comprises VL framework regions (FRs) having at least 70%, at least 75%, at least 80%, at least 85%, at least 90%, at least 95%, or at least 98% sequence identity to the VL framework regions described herein Table 7. In some embodiments, an antibody or antigen-binding fragment thereof described herein, which specifically binds to B7-H4 (e.g., human B7-H4), comprises VH framework regions (FRs) having at least 70%, at least 75%, at least 80%, at least 85%, at least 90%, at least 95%, or at least 98% sequence identity to the VH framework regions described herein Table 7, supra, and VL framework regions (FRs) having at least 70%, at least 75%, at least 80%, at least 85%, at least 90%, at least 95%, or at least 98% sequence identity to the VL framework regions described herein Table 7.

In another aspect, provided herein are antibodies or antigen-binding fragments thereof that bind the same epitope of B7-H4 (e.g., an epitope of human B7-H4) as an antibody or antigen-binding fragment thereof described herein (e.g., J511-J522).

Competition binding assays can be used to determine whether two antibodies bind to overlapping epitopes. Competitive binding can be determined in an assay in which the immunoglobulin under test inhibits specific binding of a reference antibody to a common antigen, such as B7-H4. Numerous types of competitive binding assays are known, for example: solid phase direct or indirect radioimmunoassay (RIA), solid phase direct or indirect enzyme immunoassay (EIA), sandwich competition assay (see Stahli C et al., (1983) Methods Enzymol 9: 242-253); solid phase direct biotin-avidin EIA (see Kirkland T N et al., (1986) J Immunol 137: 3614-9); solid phase direct labeled assay, solid phase direct labeled sandwich assay (see Harlow E & Lane D, (1988) Antibodies: A Laboratory Manual, Cold Spring Harbor Press); solid phase direct label RIA using I-125 label (see Morel G A et al., (1988) Mol Immunol 25(1): 7-15); solid phase direct biotin-avidin EIA (Cheung R C et al., (1990) Virology 176: 546-52); and direct labeled RIA. (Moldenhauer G et al., (1990) Scand J Immunol 32, 77-82). Typically, such an assay involves the use of purified antigen (e.g., B7-H4 such as human B7-H4) bound to a solid surface or cells bearing either of these, an unlabeled test immunoglobulin and a labeled reference immunoglobulin. Competitive inhibition can be measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70%, 70-75% or more. A competition binding assay can be configured in a large number of different formats using either labeled antigen or labeled antibody. In a common version of this assay, the antigen is immobilized on a 96-well plate. The ability of unlabeled antibodies to block the binding of labeled antibodies to the antigen is then measured using radioactive or enzyme labels. For further details see, for example, Wagener C et al., (1983) J Immunol 130: 2308-2315; Wagener C et al., (1984) J Immunol Methods 68: 269-274; Kuroki M et al., (1990) Cancer Res 50: 4872-4879, Kuroki M et al., (1992) Immunol Invest 21: 523-538, Kuroki M et al., (1992) Hybridoma 11: 391-407 and Antibodies: A Laboratory Manual, Ed Harlow E & Lane D editors supra, pp. 386-389.

In one embodiment, a competition assay is performed using surface plasmon resonance (BIAcore®), e.g., by an 'in tandem approach' such as that described by Abdiche Y N et al., (2009) Analytical Biochem 386: 172-180, whereby B7-H4 antigen is immobilized on the chip surface, for example, a CM5 sensor chip and the anti-B7-H4 antibodies are then run over the chip. To determine if an antibody or antigen-binding fragment thereof competes with an anti-B7-H4 antibody described herein, the anti-B7-H4 antibody is first run over the chip surface to achieve saturation and then the potential, competing antibody is added. Binding of the competing antibody or antigen-binding fragment thereof can then be determined and quantified relative to a non-competing control.

In one embodiment, Fortebio Octet competition binding is used to determine that a B7-H4 antibody or antigen-binding fragment thereof competitively inhibits the binding of another B7-H4 antibody or antigen-binding fragment thereof to B7-H4.

In another aspect, provided herein are antibodies that competitively inhibit (e.g., in a dose dependent manner) an antibody or antigen-binding fragment thereof described herein (e.g., J511-J522) from binding to B7-H4 (e.g., human B7-H4), as determined using assays known to one of skill in the art or described herein (e.g., ELISA competitive assays, or suspension array or surface plasmon resonance assay).

In specific aspects, provided herein is an antibody or antigen-binding fragment which competitively inhibits (e.g., in a dose dependent manner) binding to B7-H4 (e.g., human B7-H4), of an antibody comprising a VH domain having the amino acid sequence set forth in SEQ ID NO:6, and a VL domain having the amino acid sequence set for the in SEQ ID NO:9.

In specific aspects, provided herein is an antibody or antigen-binding fragment which competitively inhibits (e.g., in a dose dependent manner) binding to B7-H4 (e.g., human B7-H4), of an antibody comprising a VH domain having the amino acid sequence set forth in SEQ ID NO:7, and a VL domain having the amino acid sequence set for the in SEQ ID NO:9.

In specific aspects, provided herein is an antibody or antigen-binding fragment which competitively inhibits (e.g., in a dose dependent manner) binding to B7-H4 (e.g., human B7-H4), of an antibody comprising a VH domain having the amino acid sequence set forth in SEQ ID NO:8, and a VL domain having the amino acid sequence set for the in SEQ ID NO:9.

In specific aspects, provided herein is an antibody or antigen-binding fragment which competitively inhibits (e.g., in a dose dependent manner) binding to B7-H4 (e.g., human B7-H4), of an antibody comprising a VH domain having the amino acid sequence set forth in SEQ ID NO:6, and a VL domain having the amino acid sequence set for the in SEQ ID NO:10.

In specific aspects, provided herein is an antibody or antigen-binding fragment which competitively inhibits (e.g., in a dose dependent manner) binding to B7-H4 (e.g., human B7-H4), of an antibody comprising a VH domain having the amino acid sequence set forth in SEQ ID NO:7, and a VL domain having the amino acid sequence set for the in SEQ ID NO:10.

In specific aspects, provided herein is an antibody or antigen-binding fragment which competitively inhibits (e.g., in a dose dependent manner) binding to B7-H4 (e.g., human B7-H4), of an antibody comprising a VH domain having the amino acid sequence set forth in SEQ ID NO:8, and a VL domain having the amino acid sequence set for the in SEQ ID NO:10.

In specific aspects, provided herein is an antibody or antigen-binding fragment which competitively inhibits (e.g., in a dose dependent manner) binding to B7-H4 (e.g., human B7-H4), of an antibody comprising a VH domain having the amino acid sequence set forth in SEQ ID NO:6, and a VL domain having the amino acid sequence set for the in SEQ ID NO:11.

In specific aspects, provided herein is an antibody or antigen-binding fragment which competitively inhibits (e.g., in a dose dependent manner) binding to B7-H4 (e.g., human B7-H4), of an antibody comprising a VH domain having the amino acid sequence set forth in SEQ ID NO:7, and a VL domain having the amino acid sequence set for the in SEQ ID NO:11.

In specific aspects, provided herein is an antibody or antigen-binding fragment which competitively inhibits (e.g., in a dose dependent manner) binding to B7-H4 (e.g., human B7-H4), of an antibody comprising a VH domain having the amino acid sequence set forth in SEQ ID NO:8, and a VL domain having the amino acid sequence set for the in SEQ ID NO:11.

In specific aspects, provided herein is an antibody or antigen-binding fragment thereof, which immunospecifically binds to the same B7-H4 (e.g., human B7-H4) epitope as that of any of J511-J522.

In a specific aspect, an antigen-binding fragment as described herein, which immunospecifically binds to B7-H4 (e.g., human B7-H4), is selected from the group consisting of a Fab, Fab', F(ab')$_2$, and scFv, wherein the Fab, Fab', F(ab')$_2$, or scFv comprises a heavy chain variable region sequence and a light chain variable region sequence of an anti-B7-H4 antibody or antigen-binding fragment thereof as described herein. A Fab, Fab', F(ab')$_2$, or scFv can be produced by any technique known to those of skill in the art, including, but not limited to, those discussed in Section 5.3, infra.

An anti-B7-H4 antibody or antigen-binding fragment thereof can be fused or conjugated (e.g., covalently or noncovalently linked) to a detectable label or substance. Examples of detectable labels or substances include enzyme labels, such as glucose oxidase; radioisotopes, such as iodine ($^{125}$I, $^{121}$I), carbon ($^{14}$C), sulfur ($^{35}$S), tritium ($^3$H), indium ($^{121}$In), and technetium ($^{99}$Tc); luminescent labels, such as luminol; and fluorescent labels, such as fluorescein and rhodamine, and biotin. Such labeled antibodies or antigen-binding fragments thereof can be used to detect B7-H4 (e.g., human B7-H4) protein. See, e.g., Section 5.4.1, infra.

Antibody Production

Antibodies and antigen-binding fragments thereof that immunospecifically bind to B7-H4 (e.g., human B7-H4) can be produced by any method known in the art for the synthesis of antibodies and antigen-binding fragments thereof, for example, by chemical synthesis or by recombinant expression techniques. The methods described herein employ, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, for example, in the references cited herein and are fully explained in the literature. See, e.g., Sambrook J et al., (2001) Molecular Cloning: A Laboratory Manual, Cold Spring Harbor Laboratory Press, Cold Spring Harbor, N.Y.; Ausubel F M et al., Current Protocols in Molecular Biology, John Wiley & Sons (1987 and annual updates); Current Protocols in Immunology, John Wiley & Sons (1987 and annual updates) Gait (ed.) (1984) Oligonucleotide Synthesis: A Practical Approach, IRL Press; Eckstein (ed.) (1991) Oligonucleotides and Analogues: A Practical Approach, IRL Press; Birren B et al., (eds.) (1999) Genome Analysis: A Laboratory Manual, Cold Spring Harbor Laboratory Press.

In a certain aspect, provided herein is a method of making an antibody or antigen-binding fragment which immunospecifically binds to B7-H4 (e.g., human B7-H4) comprising culturing a cell or host cell described herein. In a certain aspect, provided herein is a method of making an antibody or antigen-binding fragment thereof which immunospecifically binds to B7-H4 (e.g., human B7-H4) comprising expressing (e.g., recombinantly expressing) the antibody or antigen-binding fragment thereof using a cell or host cell described herein (e.g., a cell or a host cell comprising polynucleotides encoding an antibody or antigen-binding fragment thereof described herein). In a particular embodiment, the cell is an isolated cell. In a particular embodiment, the exogenous polynucleotides have been introduced into the cell. In a particular embodiment, the method further comprises the step of purifying the antibody or antigen-binding fragment obtained from the cell or host cell.

Methods for producing polyclonal antibodies are known in the art (see, for example, Chapter 11 in: Short Protocols in Molecular Biology, (2002) 5th Ed., Ausubel F M et al., eds., John Wiley and Sons, New York).

Monoclonal antibodies or antigen-binding fragments thereof can be prepared using a wide variety of techniques known in the art including the use of hybridoma, recombinant, and phage display technologies, yeast-based presentation technologies, or a combination thereof. For example, monoclonal antibodies or antigen-binding fragments thereof can be produced using hybridoma techniques including those known in the art and taught, for example, in Harlow E & Lane D, Antibodies: A Laboratory Manual, (Cold Spring Harbor Laboratory Press, 2nd ed. 1988); Hammerling G J et al., in: Monoclonal Antibodies and T-Cell Hybridomas 563 681 (Elsevier, N.Y., 1981), or as described in Kohler G & Milstein C (1975) Nature 256: 495. Examples of yeast-based presentation methods that can be employed to select and generate the antibodies described herein include those disclosed in, for example, WO2009/036379A2; WO2010/105256; and WO2012/009568, each of which is herein incorporated by reference in its entirety.

In specific embodiments, a monoclonal antibody or antigen-binding fragment thereof may be produced using the hybridoma method first described by Kohler et al., Nature, 256:495 (1975), as mentioned above. In the hybridoma method, a mouse or another appropriate host animal is immunized as above described to elicit lymphocytes that produce or are capable of producing antibodies that will specifically bind to the protein used for immunization, for example, the B7-H4 extra cellular domain (ECD) protein (SEQ ID NO:20). Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986).

In specific embodiments, a monoclonal antibody or antigen-binding fragment thereof is an antibody or antigen-binding fragment produced by a clonal cell (e.g., hybridoma or host cell producing a recombinant antibody or antigen-binding fragment), wherein the antibody or antigen-binding fragment immunospecifically binds to B7-H4 (e.g., human B7-H4) as determined, e.g., by ELISA or other antigen-binding assays known in the art or in the Examples provided herein. In particular embodiments, a monoclonal antibody or antigen-binding fragment thereof can be a rodent or murine antibody or antigen-binding fragment thereof. In particular embodiments, a monoclonal antibody or antigen-binding fragment thereof can be a chimeric or a humanized antibody or antigen-binding fragment thereof. In certain embodiments, a monoclonal antibody or antigen-binding fragment thereof can be a Fab fragment or an F(ab')$_2$ fragment. Monoclonal antibodies or antigen-binding fragments thereof described herein can, for example, be made by the hybridoma method as described in Kohler G & Milstein C (1975) Nature 256: 495 or can, e.g., be isolated from phage libraries using the techniques as described herein, for example. Other methods for the preparation of clonal cell lines and of monoclonal antibodies and antigen-binding fragments thereof expressed thereby are well known in the art (see, for example, Chapter 11 in: Short Protocols in Molecular Biology, (2002) 5th Ed., Ausubel F M et al., supra).

Antigen-binding fragments of antibodies described herein can be generated by any technique known to those of skill in the art. For example, Fab and F(ab')$_2$ fragments described herein can be produced by proteolytic cleavage of immunoglobulin molecules, using enzymes such as papain (to produce Fab fragments) or pepsin (to produce F(ab')$_2$ fragments). A Fab fragment corresponds to one of the two identical arms of a tetrameric antibody molecule and contains the complete light chain paired with the VH and CH1 domains of the heavy chain. An F(ab')$_2$ fragment contains the two antigen-binding arms of a tetrameric antibody molecule linked by disulfide bonds in the hinge region.

Further, the antibodies or antigen-binding fragments thereof described herein can also be generated using various phage display and/or yeast-based presentation methods known in the art. In phage display methods, proteins are displayed on the surface of phage particles which carry the polynucleotide sequences encoding them. In particular, DNA sequences encoding VH and VL domains are amplified from animal cDNA libraries (e.g., human or murine cDNA libraries of affected tissues). The DNA encoding the VH and VL domains are recombined together with a scFv linker by PCR and cloned into a phagemid vector. The vector is electroporated in *E. coli* and the *E. coli* is infected with helper phage. Phage used in these methods are typically filamentous phage including fd and M13, and the VH and VL domains are usually recombinantly fused to either the phage gene III or gene VIII. Phage expressing an antibody or antigen-binding fragment thereof that specifically binds to a particular antigen can be selected or identified with antigen, e.g., using labeled antigen or antigen bound or captured to a solid surface or bead. Examples of phage display methods that can be used to make the antibodies or fragments described herein include those disclosed in Brinkman U et al., (1995) J Immunol Methods 182: 41-50; Ames R S et al., (1995) J Immunol Methods 184: 177-186; Kettleborough C A et al., (1994) Eur J Immunol 24: 952-958; Persic L et al., (1997) Gene 187: 9-18, Burton D R & Barbas C F (1994) Advan Immunol 57: 191-280; PCT Application No. PCT/GB91/001134; International Publication Nos. WO 90/02809, WO 91/10737, WO 92/01047, WO 92/18619, WO 93/1 1236, WO 95/15982, WO 95/20401, and WO 97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743, and 5,969,108.

An antibody or antigen-binding fragment thereof can be selected from any class of immunoglobulins, including IgM, IgG, IgD, IgA and IgE, and any isotype, including IgG$_1$, IgG$_2$, IgG$_3$ and IgG$_4$.

Polynucleotides

In certain aspects, provided herein are polynucleotides comprising a nucleotide sequence encoding an antibody or antigen-binding fragment thereof described herein or a domain thereof (e.g., a variable light chain region and/or variable heavy chain region) that immunospecifically binds to a B7-H4 (e.g., human B7-H4) antigen, and vectors, e.g., vectors comprising such polynucleotides for recombinant expression in host cells (e.g., *E. coli* and mammalian cells).

In particular aspects, provided herein are polynucleotides comprising nucleotide sequences encoding antibodies or antigen-binding fragments thereof, which immunospecifically bind to a B7-H4 polypeptide (e.g., human B7-H4) and comprise an amino acid sequence as described herein, as well as antibodies or antigen-binding fragments that compete with such antibodies or antigen-binding fragments for binding to a B7-H4 polypeptide (e.g., in a dose-dependent manner), or which bind to the same epitope as that of such antibodies or antigen-binding fragments.

Also provided herein is a polynucleotide comprising a nucleotide sequence encoding a polypeptide comprising a sequence selected from the group consisting of SEQ ID NOs:6-8. In some embodiments, an antibody or antigen-binding fragment thereof comprising the polypeptide immunospecifically binds to B7-H4.

Also provided herein is a polynucleotide comprising a nucleotide sequence encoding a polypeptide comprising a sequence selected from the group consisting of SEQ ID NOs:9-11. In some embodiments, an antibody or antigen-binding fragment thereof comprising the polypeptide immunospecifically binds to B7-H4.

Also provided herein is a polynucleotide comprising a nucleotide sequence encoding a polypeptide comprising a sequence selected from the group consisting of SEQ ID NOs:22-24 or comprising the amino acids of all of SEQ ID NOs:22-24. In some embodiments, an antibody or antigen-binding fragment thereof comprising the polypeptide immunospecifically binds to B7-H4. Also provided herein is a polynucleotide comprising a nucleotide sequence encoding a polypeptide comprising a sequence selected from the group consisting of SEQ ID NOs:25-29 or comprising all of SEQ ID NOs:25, 26, and 29, all of SEQ ID NOs:25, 27, and 29, or all of SEQ ID NOs:25, 28, and 29. In some embodiments, an antibody or antigen-binding fragment thereof comprising the polypeptide immunospecifically binds to B7-H4.

Also provided herein is a polynucleotide comprising a nucleotide sequence encoding a polypeptide comprising a sequence selected from the group consisting of SEQ ID NOs:16-18, 89, 90, and 91. In some embodiments, an antibody or antigen-binding fragment thereof comprising the polypeptide immunospecifically binds to B7-H4.

Also provided herein is a polynucleotide comprising a nucleotide sequence encoding a polypeptide comprising a sequence selected from the group consisting of SEQ ID NOs:19, 30, and 31. In some embodiments, an antibody or antigen-binding fragment thereof comprising the polypeptide immunospecifically binds to B7-H4.

Also provided herein are polynucleotides comprising a heavy chain and/or a light chain-encoding nucleotide sequence shown in Table 8, e.g., wherein an antibody or antigen-binding fragment thereof comprising the encoded heavy chain or light chain specifically binds to B7-H4.

TABLE 8

Heavy chain and light chain-encoding polynucleotide sequences

| Antibody | Heavy/Light Chain-Encoding Polynucleotide Sequence (SEQ ID NO) |
|---|---|
| J511 HC | ATGGGCAGGCTTACTTCTTCATTCCTGCTACTGATTGTCCCTGCATATGT<br>CCTGTCCCAGGTCACTCTGAAAGAGTCTGGCCCTGGGATATTGCAGCCC<br>TCCCAGACCCTCAGTCTGACTTGTTCTTTCTCTGGGTTTTCACTGAGCAC<br>TTATGGTCTGGGTGTAGGTTGGATTCGTCAGCCTTCAGGGAAGGGTCTG<br>GACTGGCTGGCCAACATTTGGTGGAATGATGATAAATACTATAACTCA<br>GCCCTGAAGAGCCGGCTCACAATCTCCAAGGATACCTCCAACAACCAG<br>GTATTCCTCAAGATCTCCAGTGTGGACACTGCAGATACTGGCACATACT<br>ACTGTGCTCAAGTTGATGGTTACTACTGGTACTTCGATGTCTGGGGCGC<br>AGGGACCACGGTCACCGTCTCCTCAGCCAAAACGACACCACCAAGTGT<br>CTATCCACTGGCCCCTGGATCTGCTGCCCAAACTAACTCCATGGTGACC<br>CTGGGATGCCTGGTCAAGGGCTATTTCCCTGAGCCAGTGACAGTGACCT<br>GGAACTCTGGATCCCTGTCCAGCGGTGTGCACACCTTCCCAGCTGTCCT<br>GGAGTCTGACCTCTACACTCTGAGCAGCTCAGTGACTGTCCCCTCCAGC<br>CCTCGGCCCAGCGAGACCGTCACCTGCAACGTTGCCCACCCGGCCAGC<br>AGCACCAAAGTGGACAAGAAAATTGTGCCCAGGGATTGTGGTTGTAAG<br>CCTTGCATATGTACAGTCCCAGAAGTATCATCTGTCTTCATCTTCCCCCC<br>AAAGCCCAAGGATGTGCTCACCATTACTCTGACTCcTAAGGTCACGTGT<br>GTTGTGGTAGACATCAGCAAGGATGATCCCGAGGTCCAGTTCAGCTGG<br>TTTGTAGATGATGTGGAGGTGCACACAGCTCAGACGCAACCCCGGGAG<br>GAGCAGTTCAACAGCACTTTCCGCTCAGTCAGTGAACTTCCCATCATGC<br>ACCAGGACTGGCTCAATGGCAAGGAGTTCAAATGCAGGGTCAACAGTG<br>CAGCTTTCCCTGCCCCCATCGAGAAAACCATCTCCAAAACCAAAGGCA<br>GACCGAAGGCTCCACAGGTGTACACCATTCCACCTCCCAAGGAGCAGA<br>TGGCCAAGGATAAAGTCAGTCTGACCTGCATGATAACAGACTTCTTCCC<br>TGAAGACATTACTGTGGAGTGGCAGTGGAATGGGCAGCCAGCGGAGAA<br>CTACAAGAACACTCAGCCCATCATGAACACGAATGGCTCTTACTTCGTC<br>TACAGCAAGCTCAATGTGCAGAAGAGCAACTGGGAGGCAGGAAATACT<br>TTCACCTGCTCTGTGTTACATGAGGGCCTGCACAACCACCATACTGAGA<br>AGAGCCTCTCCCACTCTCCTGGTAAATGA (SEQ ID NO: 93) |
| J512, J517, J518 HC | ATGGGCAGGCTTACTTCTTCATTCCTGCTACTGATTGTCCCTGCATATGT<br>CCTGTCCCAGGTCACTCTGAAAGAGTCTGGCCCTGGGATATTGCAGCCC<br>TCCCAGACCCTCAGTCTGACTTGTTCTTTCTCTGGGTTTTCACTGAGCAC<br>TTATGGTCTGGGTGTAGGTTGGATTCGTCAGCCTTCAGGGAAGGGTCTG<br>GACTGGCTGGCCAACATTTGGTGGAATGATGATAAATACTATAACTCA<br>GCCCTGAAGAGCCGGCTCACAATCTCCAAGGATACCTCCAACAACCAG<br>GTATTCCTCAAGATCTCCAGTGTGGACACTGCAGATACTGGCACATACT<br>ACTGTGCTCAAGTTGATGGTTACTACTGGTACTTCGATGTCTGGGGCGC<br>AGGGACCACGGTCACCGTCTCCTCAGCCAAAACGACACCACCAAGTGT<br>CTATCCACTGGCCCCTGGATCTGCTGCCCAAACTAACTCCATGGTGACC<br>CTGGGATGCCTGGTCAAGGGCTATTTCCCTGAGCCAGTGACAGTGACCT<br>GGAACTCTGGATCCCTGTCCAGCGGTGTGCACACCTTCCCAGCTGTCCT<br>GGAGTCTGACCTCTACACTCTGAGCAGCTCAGTGACTGTCCCCTCCAGC<br>CCTCGGCCCAGCGAGACCGTCACCTGCAACGTTGCCCACCCGGCCAGC<br>AGCACCAAAGTGGACAAGAAAATTGTGCCCAGGGATTGTGGTTGTAAG<br>CCTTGCATATGTACAGTCCCAGAAGTATCATCTGTCTTCATCTTCCCCCC<br>AAAGATCAAGGATGTACTCATGATCTCCCTGAGCCCCATAGTCACATGT<br>GTGGTGGTGGATGTGAGCGAGGATGACCCAGATGTCCAGATCAGCTGG<br>TTTGTGAACAACGTGGAAGTACACACAGCTCAGACACAAACCCATAGA<br>GAGGATTACAACAGTACTCTCCGGGTGGTCAGTGCCCTCCCCATCCAGC<br>ACCAGGACTGGATGAGTGGCAAGGAGTTCAAATGCAAGGTCAACAACA<br>AAGACCTCCCAGCGCCCATCGAGAGAACCATCTCAAAACCCAAGGGT<br>CAGTAAGAGCTCCACAGGTATATGTCTTGCCTCCACCAGAAGAAGAGA<br>TGACTAAGAAACAGGTCACTCTGACCTGCATGGTCACAGACTTCATGCC<br>TGAAGACATTTACGTGGAGTGGACCAACAACGGGAAAACAGAGCTAA<br>ACTACAAGAACACTGAACCAGTCCTGGACTCTGATGGTTCTTACTTCAT<br>GTACAGCAAGCTGAGAGTGGAAAAGAAGAACTGGGTGGAAAGAAATA<br>GCTACTCCTGTTCAGTGGTCCACGAGGGTCTGCACAATCACCACACGAC<br>TAAGAGCTTCTCCCGGACTCCGGGTAAATAGTAA (SEQ ID NO: 12) |
| J513 HC | ATGGGCAGGCTTACTTCTTCATTCCTGCTACTGATTGTCCCTGCATATGT<br>CCTGTCCCAGGTCACTCTGAAAGAGTCTGGCCCTGGGATATTGCAGCCC<br>TCCCAGACCCTCAGTCTGACTTGTTCTCTCTGGGTTTTCACTGAGCAC<br>TTATGGTCTGGGTGTAGGTTGGATTCGTCAGCCTTCAGGGAAGGGTCTG<br>GGCTGGCTGGCCAACATTTGGTGGAATGATGATAAATACTATAACTCA<br>GCCCTGAAGAGCCGGCTCACAATCTCCAAGGATACCTCCAACAACCAG<br>GTATTCCTCAAGATCTCCAGTGTGGACACTGCAGATACTGGCACATACT<br>ACTGTGCTCAAGTTGATGGTTACTACTGGTACTTCGATGTCTGGGGCGC<br>AGGGACCACGGTCACCGTCTCCTCAGCCAAAACGACACCACCAAGTGT<br>CTATCCACTGGCCCCTGGATCTGCTGCCCAAACTAACTCCATGGTGACC<br>CTGGGATGCCTGGTCAAGGGCTATTTCCCTGAGCCAGTGACAGTGACCT<br>GGAACTCTGGATCCCTGTCCAGCGGTGTGCACACCTTCCCAGCTGTCCT<br>GGAGTCTGACCTCTACACTCTGAGCAGCTCAGTGACTGTCCCCTCCAGC<br>CCTCGGCCCAGCGAGACCGTCACCTGCAACGTTGCCCACCCGGCCAGC<br>AGCACCAAGGTGGACAAGAAAATTGTGCCCAGGGATTGTGGTTGTAAG |

TABLE 8-continued

Heavy chain and light chain-encoding polynucleotide sequences

| Antibody | Heavy/Light Chain-Encoding Polynucleotide Sequence (SEQ ID NO) |
| --- | --- |
| | CCTTGCATATGTACAGTCCCAGAAGTATCATCTGTCTTCATCTTCCCCCC<br>AAAGCCCAAGGATGTGCTCACCATTACTCTGACTCcTAAGGTCACGTGT<br>GTTGTGGTAGACATCAGCAAGGATGATCCCGAGGTCCAGTTCAGCTGG<br>TTTGTAGATGATGTGGAGGTGCACACAGCTCAGACGCAACCCCGGGAG<br>GAGCAGTTCAACAGCACTTTCCGCTCAGTCAGTGAACTTCCCATCATGC<br>ACCAGGACTGGCTCAATGGCAAGGAGTTCAAATGCAGGGTCAACAGTG<br>CAGCTTTCCCTGCCCCCATCGAGAAAACCATCTCCAAAACCAAAGGCA<br>GACCGAAGGCTCCACAGGTGTACACCATTCCACCTCCCAAGGAGCAGA<br>TGGCCAAGGATAAAGTCAGTCTGACCTGCATGATAACAGACTTCTTCCC<br>TGAAGACATTACTGTGGAGTGGCAGTGGAATGGGCAGCCAGCGGAGAA<br>CTACAAGAACACTCAGCCCATCATGAACACGAATGGCTCTTACTTCGTC<br>TACAGCAAGCTCAATGTGCAGAAGAGCAACTGGGAGGCAGGAAATACT<br>TTCACCTGCTCTGTGTTACATGAGGGCCTGCACAACCACCATACTGAGA<br>AGAGCCTCTCCCACTCTCCTGGTAAATGA (SEQ ID NO: 94) |
| J514, J519,<br>J520 HC | ATGGGCAGGCTTACTTCTTCATTCCTGCTACTGATTGTCCCTGCATATGT<br>CCTGTCCCAGGTCACTCTGAAAGAGTCTGGCCCTGGGATATTGCAGCCC<br>TCCCAGACCCTCAGTCTGACTTGTTCTCTCTCTGGGTTTTCACTGAGCAC<br>TTATGGTCTGGGTGTAGGTTGGATTCGTCAGCCTTCAGGGAAGGGTCTG<br>GGCTGGCTGGCCAACATTTGGTGGAATGATGATAAATACTATAACTCA<br>GCCCTGAAGAGCCGGCTCACAATCTCCAAGGATACCTCCAACAACCAG<br>GTATTCCTCAAGATCTCCAGTGTGGACACTGCAGATACTGGCACATACT<br>ACTGTGCTCAAGTTGATGGTTACTACTGGTACTTCGATGTCTGGGGCGC<br>AGGGACCACGGTCACCGTCTCCTCAGCCAAAACGACACCACCAAGTGT<br>CTATCCACTGGCCCCTGGATCTGCTGCCCAAACTAACTCCATGGTGACC<br>CTGGGATGCCTGGTCAAGGGCTATTTCCCTGAGCCAGTGACAGTGACCT<br>GGAACTCTGGATCCCTGTCCAGCGGTGTGCACACCTTCCCAGCTGTCCT<br>GGAGTCTGACCTCTACACTCTGAGCAGCTCAGTGACTGTCCCCTCCAGC<br>CCTCGGCCCAGCGAGACCGTCACCTGCAACGTTGCCCACCCGGCCAGC<br>AGCACCAAGGTGGACAAGAAATTGTGCCCAGGGATTGTGGTTGTAAG<br>CCTTGCATATGTACAGTCCCAGAAGTATCATCTGTCTTCATCTTCCCCCC<br>AAAGATCAAGGATGTACTCATGATCTCCCTGAGCCCCATAGTCACATGT<br>GTGGTGGTGGATGTGAGCGAGGATGACCCAGATGTCCAGATCAGCTGG<br>TTTGTGAACAACGTGGAAGTACACACAGCTCAGACACAAACCCATAGA<br>GAGGATTACAACAGTACTCTCCGGGTGGTCAGTGCCCTCCCCATCCAGC<br>ACCAGGACTGGATGAGTGGCAAGGAGTTCAAATGCAAGGTCAACAACA<br>AAGACCTCCCAGCGCCCATCGAGAGAACCATCTCAAAACCCAAAGGGT<br>CAGTAAGAGCTCCACAGGTATATGTCTTGCCTCCACCAGAAGAAGAGA<br>TGACTAAGAAACAGGTCACTCTGACCTGCATGGTCACAGACTTCATGCC<br>TGAAGACATTTACGTGGAGTGGACCAACAACGGGAAAACAGAGCTAA<br>ACTACAAGAACACTGAACCAGTCCTGGACTCTGATGGTTCTTACTTCAT<br>GTACAGCAAGCTGAGAGTGGAAAAGAAGAACTGGGTGGAAAGAAATA<br>GCTACTCCTGTTCAGTGGTCCACGAGGGTCTGCACAATCACCACACGAC<br>TAAGAGCTTCTCCCGGACTCCGGGTAAATAGTAA (SEQ ID NO: 13) |
| J515 HC | ATGGGCAGGCTTACTTCTTCATTCCTGCTACTGATTGTCCCTGCATATGT<br>CCTGTCCCAGGTCACTCTGAAAGAGTCTGGCCCTGGGATATTGCAGTCC<br>TCCCAGACCCTCAGTCTGACTTGTTCTTTCTCTGGGTTTTCACTGAGCAC<br>TTATGGTCTGGGTGTAGGTTGGATTCGTCAGCCTTCAGGGAAGGGTCTG<br>GACTGGCTGGCCAACATTTGGTGGAATGATGATAAATACTATAACTCA<br>GCCCTGAAGAGCCGGCTCACAATCTCCAAGGATACCTCCAACAACCAG<br>GTATTCCTCAAGATCTCCAGTGTGGACACTGCAGATACTGGCACATACT<br>ACTGTGCTCAAGTTGATGGTTACTACTGGTACTTCGATGTCTGGGGCGC<br>AGGGACCACGGTCACCGTCTCCTCAGCCAAAACGACACCACCAAGTGT<br>CTATCCACTGGCCCCTGGATCTGCTGCCCAAACTAACTCCATGGTGACC<br>CTGGGATGCCTGGTCAAGGGCTATTTCCCTGAGCCAGTGACAGTGACCT<br>GGAACTCTGGATCCCTGTCCAGCGGTGTGCACACCTTCCCAGCTGTCCT<br>GGAGTCTGACCTCTACACTCTGAGCAGCTCAGTGACTGTCCCCTCCAGC<br>CCTCGGCCCAGCGAGACCGTCACCTGCAACGTTGCCCACCCGGCCAGC<br>AGCACCAAGGTGGACAAGAAATTGTGCCCAGGGATTGTGGTTGTAAG<br>CCTTGCATATGTACAGTCCCAGAAGTATCATCTGTCTTCATCTTCCCCCC<br>AAAGCCCAAGGATGTGCTCACCATTACTCTGACTCcTAAGGTCACGTGT<br>GTTGTGGTAGACATCAGCAAGGATGATCCCGAGGTCCAGTTCAGCTGG<br>TTTGTAGATGATGTGGAGGTGCACACAGCTCAGACGCAACCCCGGGAG<br>GAGCAGTTCAACAGCACTTTCCGCTCAGTCAGTGAACTTCCCATCATGC<br>ACCAGGACTGGCTCAATGGCAAGGAGTTCAAATGCAGGGTCAACAGTG<br>CAGCTTTCCCTGCCCCCATCGAGAAAACCATCTCCAAAACCAAAGGCA<br>GACCGAAGGCTCCACAGGTGTACACCATTCCACCTCCCAAGGAGCAGA<br>TGGCCAAGGATAAAGTCAGTCTGACCTGCATGATAACAGACTTCTTCCC<br>TGAAGACATTACTGTGGAGTGGCAGTGGAATGGGCAGCCAGCGGAGAA<br>CTACAAGAACACTCAGCCCATCATGAACACGAATGGCTCTTACTTCGTC<br>TACAGCAAGCTCAATGTGCAGAAGAGCAACTGGGAGGCAGGAAATACT<br>TTCACCTGCTCTGTGTTACATGAGGGCCTGCACAACCACCATACTGAGA<br>AGAGCCTCTCCCACTCTCCTGGTAAATGA (SEQ ID NO: 95) |

TABLE 8-continued

Heavy chain and light chain-encoding polynucleotide sequences

| Antibody | Heavy/Light Chain-Encoding Polynucleotide Sequence (SEQ ID NO) |
| --- | --- |
| J516, J521, J522 HC | ATGGGCAGGCTTACTTCTTCATTCCTGCTACTGATTGTCCCTGCATATGT<br>CCTGTCCCAGGTCACTCTGAAAGAGTCTGGCCCTGGGATATTGCAGTCC<br>TCCCAGACCCTCAGTCTGACTTGTTCTTTCTCTGGGTTTTCACTGAGCAC<br>TTATGGTCTGGGTGTAGGTTGGATTCGTCAGCCTTCAGGGAAGGGTCTG<br>GACTGGCTGGCCAACATTTGGTGGAATGATGATAAATACTATAACTCA<br>GCCCTGAAGAGCCGGCTCACAATCTCCAAGGATACCTCCAACAACCAG<br>GTATTCCTCAAGATCTCCAGTGTGGACACTGCAGATACTGGCACATACT<br>ACTGTGCTCAAGTTGATGGTTACTACTGGTACTTCGATGTCTGGGGCGC<br>AGGGACCACGGTCACCGTCCTCAGCCAAAACGACACCACCAAGTGT<br>CTATCCACTGGCCCCTGGATCTGCTGCCCAAACTAACTCCATGGTGACC<br>CTGGGATGCCTGGTCAAGGGCTATTTCCCTGAGCCAGTGACAGTGACCT<br>GGAACTCTGGATCCCTGTCCAGCGGTGTGCACACCTTCCCAGCTGTCCT<br>GGAGTCTGACCTCTACACTCTGAGCAGCTCAGTGACTGTCCCCTCCAGC<br>CCTCGGCCCAGCGAGACCGTCACCTGCAACGTTGCCCACCCGGCCAGC<br>AGCACCAAGGTGGACAAGAAAATTGTGCCCAGGGATTGTGGTTGTAAG<br>CCTTGCATATGTACAGTCCCAGAAGTATCATCTGTCTTCATCTTCCCCCC<br>AAAGATCAAGGATGTACTCATGATCTCCCTGAGCCCCATAGTCACATGT<br>GTGGTGGTGGATGTGAGCGAGGATGACCCAGATGTCCAGATCAGCTGG<br>TTTGTGAACAACGTGGAAGTACACACAGCTCAGACACAAACCCATAGA<br>GAGGATTACAACAGTACTCTCCGGGTGGTCAGTGCCCTCCCCATCCAGC<br>ACCAGGACTGGATGAGTGGCAAGGAGTTCAAATGCAAGGTCAACAACA<br>AAGACCTCCCAGCGCCCATCGAGAGAACCATCTCAAAACCCAAAGGGT<br>CAGTAAGAGCTCCACAGGTATATGTCTTGCCTCCACCAGAAGAAGAGA<br>TGACTAAGAAACAGGTCACTCTGACCTGCATGGTCACAGACTTCATGCC<br>TGAAGACATTTACGTGGAGTGGACCAACAACGGGAAAACAGAGCTAA<br>ACTACAAGAACACTGAACCAGTCCTGGACTCTGATGGTTCTTACTTCAT<br>GTACAGCAAGCTGAGAGTGGAAAAGAAGAACTGGGTGGAAAGAAATA<br>GCTACTCCTGTTCAGTGGTCCACGAGGGTCTGCACAATCACCACACGAC<br>TAAGAGCTTCTCCCGGACTCCGGGTAAATAGTAA (SEQ ID NO: 14) |
| J511 to J516 LC | ATGAAGTTGCCTGTTAGGCTGTTGGTGCTGATGTTCTGGATTCCTGCTTC<br>CGGCAGTGATGTTTTGATGACCCAAACTCCACTCTCCGGCCTGTCAGT<br>CTTGGAGATCAAGCCTCCATCTCTTGCAGATCTAGTCAGAGCATTGTAC<br>ATAGTAATAGAAACACCTATTTAGAATGGTACCTGCAGAAACCAGGCC<br>AGTCTCCAAAGCTCCTGATCTACAACGTTTCCAACCGATTTTCTGGGGT<br>CCCAGACAGGTTCAGTGGCAGTGGATCAGGGACAGATTTCACACTCAA<br>GATCAGCAGAGTGGAGGCTGAGGATCTGGGAGTTTATTACTGCTTTCA<br>AGGTTCACATGTTCCGCTCACGTTCGGTGCTGGGACCAAGCTGGAGCTG<br>AAACGGGCTGATGCTGCACCAACTGTATCCATCTTCCCACCATCCAGTG<br>AGCAGTTGACATCTGGAGGTGCCTCAGTCGTGTGCTTCTTGAACAACTT<br>CTACCCCAAAGACATCAATGTCAAGTGGAAGATTGATGGCAGTGAACG<br>ACAAAATGGCGTCCTGAACAGTTGGACTGATCAGGACAGCAAAGACAG<br>CACCTACAGCATGAGCAGCACCCTCACGTTGACCAAGGACGAGTATGA<br>ACGACATAACAGCTATACCTGTGAGGCCACTCACAAGACATCAACTTC<br>ACCCATTGTCAAGAGCTTCAACAGGAATGAGTGTTAG (SEQ ID NO: 15) |
| J517, J519, and J521 LC | ATGAAGTTGCCTGTTAGGCTGTTGGTGCTGATGTTCTGGATTCCTGCTTC<br>CGGCAGTGATGTTTTGATGACCCAAACTCCACTCTCCCTGCCTGTCAGT<br>CTTGGAGATCAAGCCTCCATCTCTTGCAGATCTAGTCAGAGCATTGTAC<br>ATAGTAATAGAAACACCTATTTAGAATGGTACCTGCAGAAACCAGGCC<br>AGTCTCCAAAGCTCCTGATCTACAACGTTGCCAACCGATTTTCTGGGGT<br>CCCAGACAGGTTCAGTGGCAGTGGATCAGGGACAGATTTCACACTCAA<br>GATCAGCAGAGTGGAGGCTGAGGATCTGGGAGTTTATTACTGCTTTCA<br>AGGTTCACATGTTCCGCTCACGTTCGGTGCTGGGACCAAGCTGGAGCTG<br>AAACGGGCTGATGCTGCACCAACTGTATCCATCTTCCCACCATCCAGTG<br>AGCAGTTGACATCTGGAGGTGCCTCAGTCGTGTGCTTCTTGAACAACTT<br>CTACCCCAAAGACATCAATGTCAAGTGGAAGATTGATGGCAGTGAACG<br>ACAAAATGGCGTCCTGAACAGTTGGACTGATCAGGACAGCAAAGACAG<br>CACCTACAGCATGAGCAGCACCCTCACGTTGACCAAGGACGAGTATGA<br>ACGACATAACAGCTATACCTGTGAGGCCACTCACAAGACATCAACTTC<br>ACCCATTGTCAAGAGCTTCAACAGGAATGAGTGTTAG (SEQ ID NO: 96) |
| J518, J520, and J522 LC | ATGAAGTTGCCTGTTAGGCTGTTGGTGCTGATGTTCTGGATTCCTGCTTC<br>CGGCAGTGATGTTTTGATGACCCAAACTCCACTCTCCCTGCCTGTCAGT<br>CTTGGAGATCAAGCCTCCATCTCTTGCAGATCTAGTCAGAGCATTGTAC<br>ATAGTAATAGAAACACCTATTTAGAATGGTACCTGCAGAAACCAGGCC<br>AGTCTCCAAAGCTCCTGATCTACCAGGTTTCCAACCGATTTTCTGGGGT<br>CCCAGACAGGTTCAGTGGCAGTGGATCAGGGACAGATTTCACACTCAA<br>GATCAGCAGAGTGGAGGCTGAGGATCTGGGAGTTTATTACTGCTTTCA<br>AGGTTCACATGTTCCGCTCACGTTCGGTGCTGGGACCAAGCTGGAGCTG<br>AAACGGGCTGATGCTGCACCAACTGTATCCATCTTCCCACCATCCAGTG<br>AGCAGTTGACATCTGGAGGTGCCTCAGTCGTGTGCTTCTTGAACAACTT<br>CTACCCCAAAGACATCAATGTCAAGTGGAAGATTGATGGCAGTGAACG<br>ACAAAATGGCGTCCTGAACAGTTGGACTGATCAGGACAGCAAAGACAG<br>CACCTACAGCATGAGCAGCACCCTCACGTTGACCAAGGACGAGTATGA |

TABLE 8-continued

Heavy chain and light chain-encoding polynucleotide sequences

| Antibody | Heavy/Light Chain-Encoding Polynucleotide Sequence (SEQ ID NO) |
|---|---|
| | ACGACATAACAGCTATACCTGTGAGGCCACTCACAAGACATCAACTTC ACCCATTGTCAAGAGCTTCAACAGGAATGAGTGTTAG (SEQ ID NO: 97) |

Also provided herein is a polynucleotide comprising a nucleic acid encoding a heavy chain variable domain, wherein the nucleic acid encoding the heavy chain variable domain comprises the three CDR-encoding sequence of SEQ ID NO:12. Also provided herein is a polynucleotide comprising a nucleic acid encoding a heavy chain variable domain, wherein the nucleic acid encoding the heavy chain variable domain comprises the three CDR-encoding sequence of SEQ ID NO:13. Also provided herein is a polynucleotide comprising a nucleic acid encoding a heavy chain variable domain, wherein the nucleic acid encoding the heavy chain variable domain comprises the three CDR-encoding sequence of SEQ ID NO:14. Also provided herein is a polynucleotide comprising a nucleic acid encoding a heavy chain variable domain, wherein the nucleic acid encoding the heavy chain variable domain comprises the three CDR-encoding sequence of SEQ ID NO:93. Also provided herein is a polynucleotide comprising a nucleic acid encoding a heavy chain variable domain, wherein the nucleic acid encoding the heavy chain variable domain comprises the three CDR-encoding sequence of SEQ ID NO:94. Also provided herein is a polynucleotide comprising a nucleic acid encoding a heavy chain variable domain, wherein the nucleic acid encoding the heavy chain variable domain comprises the three CDR-encoding sequence of SEQ ID NO:95.

Also provided herein is a polynucleotide comprising a nucleic acid encoding a light chain variable domain, wherein the nucleic acid encoding the light chain variable domain comprises the three CDR-encoding sequence of SEQ ID NO:15. Also provided herein is a polynucleotide comprising a nucleic acid encoding a light chain variable domain, wherein the nucleic acid encoding the light chain variable domain comprises the three CDR-encoding sequence of SEQ ID NO:96. Also provided herein is a polynucleotide comprising a nucleic acid encoding a light chain variable domain, wherein the nucleic acid encoding the light chain variable domain comprises the three CDR-encoding sequence of SEQ ID NO:97.

Also provided herein is a composition comprising (i) a polynucleotide comprising a nucleic acid encoding a heavy chain variable domain, wherein the nucleic acid encoding the heavy chain variable domain comprises the three CDR-encoding sequence of SEQ ID NO:12 or 93 and (ii) a polynucleotide comprising a nucleic acid encoding a light chain variable domain, wherein the nucleic acid encoding the light chain variable domain comprises the three CDR-encoding sequence of SEQ ID NO:15, 96, or 97. The nucleic acid encoding the heavy chain variable domain and the nucleic acid encoding the light chain variable domain may be in the same polynucleotide or in different polynucleotides. The nucleic acid encoding the heavy chain variable domain and the nucleic acid encoding the light chain variable domain may be in the same vector or in different vectors.

Also provided herein is a composition comprising (i) a polynucleotide comprising a nucleic acid encoding a heavy chain variable domain, wherein the nucleic acid encoding the heavy chain variable domain comprises the three CDR-encoding sequence of SEQ ID NO:13 or 94 and (ii) a polynucleotide comprising a nucleic acid encoding a light chain variable domain, wherein the nucleic acid encoding the light chain variable domain comprises the three CDR-encoding sequence of SEQ ID NO:15, 96, or 97. The nucleic acid encoding the heavy chain variable domain and the nucleic acid encoding the light chain variable domain may be in the same polynucleotide or in different polynucleotides. The nucleic acid encoding the heavy chain variable domain and the nucleic acid encoding the light chain variable domain may be in the same vector or in different vectors.

Also provided herein is a composition comprising (i) a polynucleotide comprising a nucleic acid encoding a heavy chain variable domain, wherein the nucleic acid encoding the heavy chain variable domain comprises the three CDR-encoding sequence of SEQ ID NO:14 or 95 and (ii) a polynucleotide comprising a nucleic acid encoding a light chain variable domain, wherein the nucleic acid encoding the light chain variable domain comprises the three CDR-encoding sequence of SEQ ID NO:15, 96, or 97. The nucleic acid encoding the heavy chain variable domain and the nucleic acid encoding the light chain variable domain may be in the same polynucleotide or in different polynucleotides. The nucleic acid encoding the heavy chain variable domain and the nucleic acid encoding the light chain variable domain may be in the same vector or in different vectors.

Also provided herein is a polynucleotide comprising a nucleic acid encoding a heavy chain variable domain, wherein the nucleic acid encoding the heavy chain variable domain comprises the variable domain-encoding sequence of SEQ ID NO:12. Also provided herein is a polynucleotide comprising a nucleic acid encoding a heavy chain variable domain, wherein the nucleic acid encoding the heavy chain variable domain comprises the variable domain-encoding sequence of SEQ ID NO:13. Also provided herein is a polynucleotide comprising a nucleic acid encoding a heavy chain variable domain, wherein the nucleic acid encoding the heavy chain variable domain comprises the variable domain-encoding sequence of SEQ ID NO:14. Also provided herein is a polynucleotide comprising a nucleic acid encoding a heavy chain variable domain, wherein the nucleic acid encoding the heavy chain variable domain comprises the variable domain-encoding sequence of SEQ ID NO:93. Also provided herein is a polynucleotide comprising a nucleic acid encoding a heavy chain variable domain, wherein the nucleic acid encoding the heavy chain variable domain comprises the variable domain-encoding sequence of SEQ ID NO:94. Also provided herein is a polynucleotide comprising a nucleic acid encoding a heavy chain variable domain, wherein the nucleic acid encoding the heavy chain variable domain comprises the variable domain-encoding sequence of SEQ ID NO:95.

Also provided herein is a polynucleotide comprising a nucleic acid encoding a light chain variable domain, wherein the nucleic acid encoding the light chain variable domain comprises the variable domain-encoding sequence of SEQ ID NO:15. Also provided herein is a polynucleotide comprising a nucleic acid encoding a light chain variable domain, wherein the nucleic acid encoding the light chain variable domain comprises the variable domain-encoding sequence of SEQ ID NO:96. Also provided herein is a polynucleotide comprising a nucleic acid encoding a light chain variable domain, wherein the nucleic acid encoding the light chain variable domain comprises the variable domain-encoding sequence of SEQ ID NO:97.

Also provided herein is a composition comprising (i) a polynucleotide comprising a nucleic acid encoding a heavy chain variable domain, wherein the nucleic acid encoding the heavy chain variable domain comprises the variable domain-encoding sequence of SEQ ID NO:12 or 93 and (ii) a polynucleotide comprising a nucleic acid encoding a light chain variable domain, wherein the nucleic acid encoding the light chain variable domain comprises the variable domain-encoding sequence of SEQ ID NO:15, 96, or 97. The nucleic acid encoding the heavy chain variable domain and the nucleic acid encoding the light chain variable domain may be in the same polynucleotide or in different polynucleotides. The nucleic acid encoding the heavy chain variable domain and the nucleic acid encoding the light chain variable domain may be in the same vector or in different vectors.

Also provided herein is a composition comprising (i) a polynucleotide comprising a nucleic acid encoding a heavy chain variable domain, wherein the nucleic acid encoding the heavy chain variable domain comprises the variable domain-encoding sequence of SEQ ID NO:13 or 94 and (ii) a polynucleotide comprising a nucleic acid encoding a light chain variable domain, wherein the nucleic acid encoding the light chain variable domain comprises the variable domain-encoding sequence of SEQ ID NO:15, 96, or 97. The nucleic acid encoding the heavy chain variable domain and the nucleic acid encoding the light chain variable domain may be in the same polynucleotide or in different polynucleotides. The nucleic acid encoding the heavy chain variable domain and the nucleic acid encoding the light chain variable domain may be in the same vector or in different vectors.

Also provided herein is a composition comprising (i) a polynucleotide comprising a nucleic acid encoding a heavy chain variable domain, wherein the nucleic acid encoding the heavy chain variable domain comprises the variable domain-encoding sequence of SEQ ID NO:14 or 95 and (ii) a polynucleotide comprising a nucleic acid encoding a light chain variable domain, wherein the nucleic acid encoding the light chain variable domain comprises the variable domain-encoding sequence of SEQ ID NO:15, 96, or 97. The nucleic acid encoding the heavy chain variable domain and the nucleic acid encoding the light chain variable domain may be in the same polynucleotide or in different polynucleotides. The nucleic acid encoding the heavy chain variable domain and the nucleic acid encoding the light chain variable domain may be in the same vector or in different vectors.

Also provided herein are polynucleotides comprising a nucleotide sequence that encodes SEQ ID NO:6, 7, 8, 9, 10, 11, 22, 23, 24, 25, 26, 27, 28, or 29, respectively.

Also provided herein are polynucleotides that are at least about 80%, 85%, or 90% identical to a nucleotide sequence that encodes SEQ ID NO:6, 7, 8, 9, 10, 11, 22, 23, 24, 25, 26, 27, 28, or 29, respectively.

Also provided herein are polynucleotides comprising a nucleotide sequence that is at least about 95% identical to a nucleotide sequence that encodes SEQ ID NO:6, 7, 8, 9, 10, 11, 22, 23, 24, 25, 26, 27, 28, or 29, respectively. Also provided herein are polynucleotides comprising a nucleotide sequence that is at least about 96% identical to a nucleotide sequence that encodes SEQ ID NO:6, 7, 8, 9, 10, 11, 22, 23, 24, 25, 26, 27, 28, or 29, respectively. Also provided herein are polynucleotides comprising a nucleotide sequence that is at least about 97% identical to a nucleotide sequence that encodes SEQ ID NO:6, 7, 8, 9, 10, 11, 22, 23, 24, 25, 26, 27, 28, or 29, respectively. Also provided herein are polynucleotides comprising a nucleotide sequence that is at least about 98% identical to a nucleotide sequence that encodes SEQ ID NO:6, 7, 8, 9, 10, 11, 22, 23, 24, 25, 26, 27, 28, or 29, respectively. Also provided herein are polynucleotides comprising a nucleotide sequence that is at least about 99% identical to a nucleotide sequence that encodes SEQ ID NO:6, 7, 8, 9, 10, 11, 22, 23, 24, 25, 26, 27, 28, or 29, respectively.

In a particular embodiment, a polynucleotide or combination of polynucleotides provided herein comprises a nucleotide sequence or combination of nucleotide sequences encoding an antibody or antigen-binding fragment thereof that immunospecifically binds to B7-H4 (e.g., human B7-H4), wherein the antibody or antigen-binding fragment thereof comprises a heavy chain, wherein the heavy chain comprises a heavy chain variable domain comprising an amino acid sequence set forth in Table 3 (e.g., SEQ ID NOs:6-8) and a constant region comprising the amino acid sequence of a murine gamma (γ) heavy chain constant region (e.g., IgG1 or IgG2a).

In a particular embodiment, a polynucleotide or combination of polynucleotides provided herein comprises a nucleotide sequence or combination of nucleotide sequences encoding an antibody or antigen-binding fragment thereof that immunospecifically binds to B7-H4 (e.g., human B7-H4), wherein the antibody or antigen-binding fragment thereof comprises a light chain, wherein the light chain comprises a light chain variable domain comprising an amino acid sequence set forth in Table 4 (e.g., SEQ ID NOs:9-11) and a constant region comprising the amino acid sequence of a murine kappa light chain constant region.

In a specific embodiment, provided herein are polynucleotides comprising a nucleotide sequence encoding an anti-B7-H4 antibody or antigen-binding fragment thereof or a domain thereof, designated herein, see, e.g., Table 1.

Also provided herein are polynucleotides encoding an anti-B7-H4 antibody or antigen-binding fragment thereof described herein or a domain thereof that are optimized, e.g., by codon/RNA optimization, replacement with heterologous signal sequences, and elimination of mRNA instability elements. Methods to generate optimized nucleic acids encoding an anti-B7-H4 antibody or antigen-binding fragment thereof or a domain thereof (e.g., heavy chain, light chain, VH domain, or VL domain) for recombinant expression by introducing codon changes (e.g., a codon change that encodes the same amino acid due to the degeneracy of the genetic code) and/or eliminating inhibitory regions in the mRNA can be carried out by adapting the optimization methods described in, e.g., U.S. Pat. Nos. 5,965,726; 6,174,666; 6,291,664; 6,414,132; and 6,794,498, accordingly.

A polynucleotide encoding an antibody or antigen-binding fragment thereof described herein or a domain thereof can be generated from nucleic acid from a suitable source (e.g., a hybridoma) using methods well known in the art (e.g., PCR and other molecular cloning methods). For example, PCR amplification using synthetic primers hybridizable to the 3' and 5' ends of a known sequence can be performed using genomic DNA obtained from hybridoma cells producing the antibody of interest. Such PCR amplification methods can be used to obtain nucleic acids comprising the sequence encoding the light chain and/or heavy chain of an antibody or antigen-binding fragment thereof. Such PCR amplification methods can be used to obtain nucleic acids comprising the sequence encoding the variable light chain region and/or the variable heavy chain region of an antibody or antigen-binding fragment thereof. The amplified nucleic acids can be cloned into vectors for expression in host cells and for further cloning, for example, to generate chimeric and humanized antibodies or antigen-binding fragments thereof.

Polynucleotides provided herein can be, e.g., in the form of RNA or in the form of DNA. DNA includes cDNA, genomic DNA, and synthetic DNA, and DNA can be double-stranded or single-stranded. If single stranded, DNA can be the coding strand or non-coding (anti-sense) strand. In certain embodiments, the polynucleotide is a cDNA or a DNA lacking one more endogenous introns. In certain embodiments, a polynucleotide is a non-naturally occurring polynucleotide. In certain embodiments, a polynucleotide is recombinantly produced. In certain embodiments, the polynucleotides are isolated. In certain embodiments, the polynucleotides are substantially pure. In certain embodiments, a polynucleotide is purified from natural components.

Cells and Vectors

In certain aspects, provided herein are vectors (e.g., expression vectors) comprising polynucleotides comprising nucleotide sequences encoding anti-B7-H4 antibodies and antigen-binding fragments thereof or a domain thereof for recombinant expression in host cells, preferably in mammalian cells. Also provided herein are cells, e.g. host cells, comprising such vectors for recombinantly expressing anti-B7-H4 antibodies or antigen-binding fragments thereof described herein. In a particular aspect, provided herein are methods for producing an antibody or antigen-binding fragments thereof described herein, comprising expressing such antibody or antigen-binding fragment thereof in a host cell.

In certain embodiments, recombinant expression of an antibody or antigen-binding fragment thereof or domain thereof described herein (e.g., a heavy or light chain described herein) that specifically binds to B7-H4 (e.g., human B7-H4) involves construction of an expression vector containing a polynucleotide that encodes the antibody or antigen-binding fragment thereof or domain thereof. Once a polynucleotide encoding an antibody or antigen-binding fragment thereof or domain thereof (e.g., heavy or light chain variable domain) described herein has been obtained, the vector for the production of the antibody or antigen-binding fragment thereof can be produced by recombinant DNA technology using techniques well known in the art. Thus, methods for preparing a protein by expressing a polynucleotide containing an antibody or antigen-binding fragment thereof or domain thereof (e.g., light chain or heavy chain) encoding nucleotide sequence are described herein. Methods which are well known to those skilled in the art can be used to construct expression vectors containing antibody or antigen-binding fragment thereof or domain thereof (e.g., light chain or heavy chain) coding sequences and appropriate transcriptional and translational control signals. These methods include, for example, in vitro recombinant DNA techniques, synthetic techniques, and in vivo genetic recombination. Also provided are replicable vectors comprising a nucleotide sequence encoding an antibody or antigen-binding fragment thereof described herein, a heavy or light chain, a heavy or light chain variable domain, or a heavy or light chain CDR, operably linked to a promoter. Such vectors can, for example, include the nucleotide sequence encoding the constant region of the antibody or antigen-binding fragment thereof (see, e.g., International Publication Nos. WO 86/05807 and WO 89/01036; and U.S. Pat. No. 5,122,464), and variable domains of the antibody or antigen-binding fragment thereof can be cloned into such a vector for expression of the entire heavy, the entire light chain, or both the entire heavy and light chains.

An expression vector can be transferred to a cell (e.g., host cell) by conventional techniques, and the resulting cells can then be cultured by conventional techniques to produce an antibody or antigen-binding fragment thereof described herein (e.g., an antibody or antigen-binding fragment thereof comprising the six CDRs of SEQ ID NOs:22-25, 26, 27, or 28, and 29, the VH of SEQ ID NOs:6-8, the VL of SEQ ID NOs:9-11, the VH of SEQ ID NOs:6-8 and the VL of SEQ ID NOs:9-11, the heavy chain of SEQ ID NO:16-18, 89, 90, or 91, the light chain of SEQ ID NO:19, 30, 31, or the heavy chain of SEQ ID NOs16-18, 89, 90, or 91 and the light chain of SEQ ID NO:19, 30, or 31). Thus, provided herein are host cells containing a polynucleotide encoding an antibody or antigen-binding fragment thereof described herein e.g., an antibody or antigen-binding fragment thereof comprising the six CDRs of SEQ ID NOs:22-25, 26, 27, or 28, and 29, the VH of SEQ ID NOs:6-8, the VL of SEQ ID NOs:9-11, the VH of SEQ ID NOs:6-8 and the VL of SEQ ID NOs:9-11, the heavy chain of SEQ ID NO:16-18, 89, 90, or 91, the light chain of SEQ ID NO:19, 30, or 31, or the heavy chain of SEQ ID NO:16-18, 89, 90, or 91 and the light chain of SEQ ID NO:19, 30, or 31), operably linked to a promoter for expression of such sequences in the host cell. In certain embodiments, for the expression of double-chained antibodies or antigen-binding fragments thereof, vectors encoding both the heavy and light chains, individually, can be co-expressed in the host cell for expression of the entire immunoglobulin, as detailed below. In certain embodiments, a host cell contains a vector comprising a polynucleotide encoding both the heavy chain and light chain of an antibody described herein or a domain thereof. In specific embodiments, a host cell contains two different vectors, a first vector comprising a polynucleotide encoding a heavy chain or a heavy chain variable region of an antibody or antigen-binding fragment thereof described herein, and a second vector comprising a polynucleotide encoding a light chain or a light chain variable region of an antibody described herein (e.g., an antibody comprising the six CDRs of SEQ ID NOs:22-25, 26, 27, or 28, and 29), or a domain thereof. In other embodiments, a first host cell comprises a first vector comprising a polynucleotide encoding a heavy chain or a heavy chain variable region of an antibody or antigen-binding fragment thereof described herein, and a second host cell comprises a second vector comprising a polynucleotide encoding a light chain or a light chain variable region of an antibody or antigen-binding fragment thereof described herein (e.g., an antibody or antigen-binding fragment thereof comprising the six CDRs of SEQ ID NOs:22-25, 26, 27, or 28, and 29). In specific embodiments, a heavy chain/heavy chain variable region expressed by a first cell associated with a light chain/light chain variable region of a second cell to form an anti-B7-H4 antibody or antigen-binding fragment thereof described herein (e.g., antibody or antigen-binding fragment thereof comprising the six CDRs of SEQ ID NOs:22-25, 26, 27, or 28, and 29). In certain embodiments, provided herein is a population of host cells comprising such first host cell and such second host cell.

In a particular embodiment, provided herein is a population of vectors comprising a first vector comprising a polynucleotide encoding a light chain/light chain variable region of an anti-B7-H4 antibody or antigen-binding fragment thereof described herein, and a second vector comprising a polynucleotide encoding a heavy chain/heavy chain variable region of an anti-B7-H4 antibody or antigen-binding fragment thereof described herein (e.g., antibody or antigen-binding fragment thereof comprising the CDRs of SEQ ID NOs:22-25, 26, 27, or 28, and 29). Alternatively, a single vector can be used which encodes, and is capable of expressing, both heavy and light chain polypeptides.

A variety of host-expression vector systems can be utilized to express antibodies and antigen-binding fragments thereof described herein (e.g., an antibody or antigen-binding fragment thereof comprising the CDRs of SEQ ID NOs:22-25, 26, 27, or 28, and 29) (see, e.g., U.S. Pat. No. 5,807,715). Such host-expression systems represent vehicles by which the coding sequences of interest can be produced and subsequently purified, but also represent cells which can, when transformed or transfected with the appropriate nucleotide coding sequences, express an antibody or antigen-binding fragment thereof described herein in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces Pichia*) transformed with recombinant yeast expression vectors containing antibody coding sequences, insect cell systems infected with recombinant virus expression vectors (e.g., baculovirus) containing antibody coding sequences; plant cell systems (e.g., green algae such as *Chlamydomonas reinhardtii*) infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS (e.g., COS1 or COS), CHO, BHK, MDCK, HEK 293, NS0, PER.C6, VERO, CRL7O3O, HsS78Bst, HeLa, and NIH 3T3, HEK-293T, HepG2, SP210, R1.1, B-W, L-M, BSC1, BSC40, YB/20 and BMT10 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In a specific embodiment, cells for expressing antibodies and antigen-binding fragments thereof described herein (e.g., an antibody or antigen-binding fragment thereof comprising the CDRs of SEQ ID NOs:22-25, 26, 27, or 28, and 29) are CHO cells, for example CHO cells from the CHO GS System™ (Lonza). In a particular embodiment, cells for expressing antibodies described herein are human cells, e.g., human cell lines. In a specific embodiment, a mammalian expression vector is pOptiVEC™ or pcDNA3.3. In a particular embodiment, bacterial cells such as *Escherichia coli*, or eukaryotic cells (e.g., mammalian cells), especially for the expression of whole recombinant antibody molecule, are used for the expression of a recombinant antibody molecule. For example, mammalian cells such as Chinese hamster ovary (CHO) cells in conjunction with a vector such as the major intermediate early gene promoter element from human cytomegalovirus is an effective expression system for antibodies (Foecking M K & Hofstetter H (1986) Gene 45: 101-105; and Cockett M I et al., (1990) Biotechnology 8: 662-667). In certain embodiments, antibodies or antigen-binding fragments thereof described herein are produced by CHO cells or NS0 cells.

In some embodiments, a signal peptide is used in constructing a vector containing the VH or VL of an antibody or antigen-binding fragment thereof provided herein. In one specific embodiment, the nucleotide sequence and the amino acid sequence of a signal peptide used to construct an expressing vector for the VH sequence are provided in SEQ ID NO:2 and 4, respectively. In another specific embodiment, the nucleotide sequence and the amino acid sequence of a signal peptide used to construct an expressing vector for the VL sequence are provided in SEQ ID NO:3 and 5, respectively.

In one specific embodiment, the nucleotide sequence of the VH signal peptide is provided as ATGGGC AGGCTT ACTTCT TCATTC CTGCTA CTGATT GTCCCT GCATAT GTCCTG TCC (SEQ ID NO:2). In another specific embodiment, the amino acid sequence of the VH signal peptide is provided as MGRLTSSFLLLIVPAYVLS (SEQ ID NO:4).

In one specific embodiment, the nucleotide sequence of the VL signal peptide is provided as ATGAAG TTGCCT GTTAGG CTGTTG GTGCTG ATGTTC TGGATT CCTGCT TCCGGC AGT (SEQ ID NO:3). In another specific embodiment, the amino acid sequence of the VL signal peptide is provided as MKLPVRLLVLMFWIPASGS (SEQ ID NO:5).

In addition, a host cell strain can be chosen which modulates the expression of the inserted sequences, or modifies and processes the gene product in the specific fashion desired. Such modifications (e.g., glycosylation) and processing (e.g., cleavage) of protein products can contribute to the function of the protein. To this end, eukaryotic host cells which possess the cellular machinery for proper processing of the primary transcript, glycosylation, and phosphorylation of the gene product can be used. Such mammalian host cells include but are not limited to CHO, VERO, BHK, HeLa, MDCK, HEK 293, NIH 3T3, W138, BT483, Hs578T, HTB2, BT2O and T47D, NS0 (a murine myeloma cell line that does not endogenously produce any immunoglobulin chains), CRL7O3O, COS (e.g., COS1 or COS), PER.C6, VERO, HsS78Bst, HEK-293T, HepG2, SP210, R1.1, B-W, L-M, BSC1, BSC40, YB/20, BMT10 and HsS78Bst cells. In certain embodiments, anti-B7-H4 antibodies described herein (e.g., an antibody or antigen-binding fragment thereof comprising the CDRs of SEQ ID NOs:22-25, 26, 27, or 28, and 29) are produced in mammalian cells, such as CHO cells.

In certain embodiments, anti-B7-H4 antibodies described herein (e.g., an antibody or antigen-binding fragment thereof comprising the CDRs of SEQ ID NOs:22-25, 26, 27, or 28, and 29) are produced in Potelligent® CHOK1SV cells.

Once an antibody or antigen-binding fragment thereof described herein has been produced by recombinant expression, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies or antigen-binding fragments thereof described herein can be fused to heterologous polypeptide sequences described herein or otherwise known in the art to facilitate purification.

In specific embodiments, an antibody or antigen-binding fragment thereof described herein is isolated or purified.

Generally, an isolated antibody or antigen-binding fragment thereof is one that is substantially free of other antibodies or antigen-binding fragments thereof with different antigenic specificities than the isolated antibody or antigen-binding fragment thereof. For example, in a particular embodiment, a preparation of an antibody or antigen-binding fragment thereof described herein is substantially free of cellular material and/or chemical precursors.

Uses and Methods

Detection & Diagnostic Uses

An anti-B7-H4 antibody or antigen-binding fragment thereof described herein (see, e.g., Section 5.2) can be used to assay B7-H4 protein levels in a biological sample using methods known to those of skill in the art, including immunoassays, such as the enzyme linked immunosorbent assay (ELISA), fluorescence-activated cell sorting (FACS), immunohistochemistry (IHC), immunoprecipitation, and Western blotting.

Suitable antibody assay labels are known in the art and include enzyme labels, such as, horseradish peroxidase (HRP) and glucose oxidase; radioisotopes, such as iodine ($^{125}I$, $^{121}I$), carbon ($^{14}C$), sulfur ($^{35}S$), tritium ($^{3}H$), indium ($^{121}In$), and technetium ($^{99}Tc$); haptens, fluorescent labels, phosphorescent molecules, chemiluminescent molecules, chromophores, luminescent molecules, photoaffinity molecules, colored particles and/or ligands, such as biotin. In some embodiments, an enzyme (an enzyme tag) will generate a colored product upon contact with a chromogenic substrate. Examples of suitable enzymes include urease, alkaline phosphatase, (horseradish) hydrogen peroxidase and/or glucose oxidase.

Such labels can be used to label an antibody or antigen-binding fragment thereof described herein. Alternatively, a second antibody or antigen-binding fragment thereof that recognizes an anti-B7-H4 antibody or antigen-binding fragment thereof described herein can be labeled and used in combination with an anti-B7-H4 antibody or antigen-binding fragment thereof to detect B7-H4 protein levels. In some embodiments, such a secondary antibody or antigen-binding fragment thereof, e.g., an anti-mouse or anti-rodent antibody, is labeled with an enzyme (e.g., horseradish peroxidase) and detected with a substrate of the enzyme (e.g., 3,3'-diaminobenzidine (DAB)).

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948, each incorporated herein by reference). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors, for example, is achieved using monoclonal antibodies, and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region, has also been disclosed in the literature (O'Shannessy et al., Biotechnol Appl Biochem. 1987 December; 9(6):488-96).

Assaying for the expression level of B7-H4 protein is intended to include qualitatively or quantitatively measuring or estimating the level of a B7-H4 protein in a first biological sample either directly (e.g., by determining or estimating absolute protein level) or relatively (e.g., by comparing to B7-H4 protein level in a second biological sample or standard). B7-H4 polypeptide expression level in the first biological sample can be measured or estimated and compared to a standard B7-H4 protein level, the standard being determined from a second biological sample that is not diseased or being determined by averaging levels from a population of samples that are not diseased. As will be appreciated in the art, once the "standard" B7-H4 polypeptide level is known, it can be used repeatedly as a standard for comparison.

As used herein, the term "biological sample" refers to any biological sample obtained from a subject, cell line, tissue, or other source of cells potentially expressing B7-H4. Non-limiting sources of a biological sample for use in the present invention include solid tissue, biopsy, ascites, aspirates, fluidic extracts, blood (including circulating tumor cells), plasma, serum, spinal fluid, lymph fluid, the external sections of the skin, respiratory, intestinal, and genitourinary tracts, tears, saliva, milk, tumors, organs, cell cultures and/or cell culture constituents, for example. Methods for obtaining tissue biopsies and body fluids from animals (e.g., humans) are well known in the art. Exemplary methods of obtaining circulating tumor cells (CTCs) are disclosed in Ferreira el al., *Molecular Oncology* 10: 374-394, which is herein incorporated by reference in its entirety. For instance, CTCs can be enriched from a blood sample using immunoaffinity-based or biophysically-based strategies. CTCs can also be obtained using direct imaging modalities. Exemplary methods of obtaining and processing biopsies, which can be used in immunohistochemical (IHC) assays are provided herein in Example 4.

An anti-B7-H4 antibody described herein can be used for diagnostic applications, including in vitro applications well known and standard to the skilled artisan and based on the present description. Diagnostic assays and kits for in vitro assessment of B7-H4 may be utilized to evaluate patient samples including those known to have or suspected of having cancer. This type of prognostic and diagnostic monitoring and assessment is in practice, e.g., utilizing antibodies against the HER2 protein in breast cancer (HercepTest™, Dako) in which the assay is used to evaluate patients for antibody therapy using Herceptin®.

Anti-B7-H4 antibodies and antigen-binding fragments thereof described herein can carry a detectable or functional label. When fluorescence labels are used, currently available microscopy and fluorescence-activated cell sorter analysis (FACS) or combination of both methods procedures known in the art may be utilized to identify and to quantitate the specific binding members. Anti-B7-H4 antibodies or antigen-binding fragments thereof described herein can carry a fluorescence label. Exemplary fluorescence labels include, for example, reactive and conjugated probes, e.g., Aminocoumarin, Fluorescein and Texas red, Alexa Fluor dyes, Cy dyes and DyLight dyes. An anti-B7-H4 antibody can carry a radioactive label, such as the isotopes $^{3}H$, $^{14}C$, $^{32}P$, $^{35}S$, $^{36}Cl$, $^{51}Cr$, $^{57}Co$, $^{58}Co$, $^{59}Fe$, $^{67}Cu$, $^{90}Y$, $^{99}Tc$, $^{111}In$, $^{117}Lu$, $^{121}$I, $^{124}$I, $^{125}$I, $^{131}$I, $^{198}$Au, $^{211}$At, $^{213}$Bi, $^{225}$Ac and $^{186}$Re. When radioactive labels are used, currently available counting procedures known in the art may be utilized to identify and quantitate the specific binding of anti-B7-H4 antibody or antigen-binding fragment to B7-H4 (e.g., human B7-H4). In the instance where the label is an enzyme, detection may be accomplished by any of the presently utilized colorimetric, spectrophotometric, fluorospectrophotometric, amperometric or gasometric techniques as known in the art. This can be achieved by contacting a sample or a control sample with an anti-B7-H4 antibody or antigen-binding fragment thereof under conditions that allow for the formation of a complex between the antibody or antigen-binding fragment thereof and B7-H4. Any complexes formed between the antibody or antigen-binding fragment thereof and B7-H4 are detected and compared in the sample and the control. In light of the specific binding of the antibodies or antigen-binding fragments thereof described herein for B7-H4, the antibodies or antigen-binding fragments thereof can be used to specifically detect B7-H4 expression, e.g., in whole cells, on cell membranes, or in cytoplasm. The antibodies or antigen-binding fragments thereof described herein can also be used to purify B7-H4 via immunoaffinity purification.

Also included herein is an assay system which may be prepared in the form of a test kit for the quantitative analysis of the extent of the presence of, for instance, B7-H4. The system or test kit may comprise a labeled component, e.g., a labeled antibody or antigen-binding fragment, and one or more additional immunochemical reagents. See, e.g., Section 5.4.3 below for more on kits.

In some aspects, methods for detecting B7-H4 in a sample in vitro, comprise contacting the sample with an antibody or antigen-binding fragment thereof as provided herein. In some aspects, provided herein is the use of an antibody or antigen-binding fragment thereof as provided herein, for detecting B7-H4 in a sample in vitro. In one aspect, provided herein is an antibody or antigen-binding fragment thereof provided herein for use in the detection of B7-H4 in a subject or a sample obtained from a subject. In one aspect, provided herein is an antibody or antigen-binding fragment thereof provided herein for use as a diagnostic. In one embodiment, the antibody comprises a detectable label. In one preferred embodiment, B7-H4 is human B7-H4. In one preferred embodiment, the subject is a human. In a further embodiment, the subject, e.g., a human subject, has cancer.

In some aspects, the present invention contemplates immunodetection methods for binding and detecting B7-H4. The antibodies prepared in accordance with the present invention may be employed to detect B7-H4. Some immunodetection methods include immunohistochemistry, flow cytometry, enzyme linked immunosorbent assay (ELISA), radioimmunoassay (RIA), immunoradiometric assay, fluoroimmunoassay, chemiluminescent assay, bioluminescent assay, and Western blot to mention a few. The steps of various useful immunodetection methods have been described in the scientific literature, such as, e.g., Doolittle M H and Ben-Zeev O, Methods Mol Biol. 1999; 109:215-37; Gulbis B and Galand P, Hum Pathol. 1993 December; 24(12):1271-85; and De Jager R et al., Semin Nucl Med. 1993 April; 23(2):165-79, each incorporated herein by reference.

In general, the immunobinding methods include obtaining a sample, e.g. a sample suspected of comprising B7-H4, and contacting the sample with a first anti-B7-H4 antibody in accordance with the present invention under conditions effective to allow the formation of immunocomplexes.

Contacting the chosen biological sample with the antibody under effective conditions and for a period of time sufficient to allow the formation of immune complexes (primary immune complexes) generally comprises adding the antibody composition to the sample and incubating the mixture for a period of time sufficient for the antibodies to form immune complexes with, i.e., to specifically bind to, any B7-H4 present. After this time, the sample-antibody composition, such as a tissue section, ELISA plate, dot blot or western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. U.S. Patents concerning the use of such labels include U.S. Pat. Nos. 3,817,837; 3,850,752; 3,939,350; 3,996,345; 4,277,437; 4,275,149 and 4,366,241, each incorporated herein by reference. In some embodiments, a secondary binding agent, such as a second antibody and/or a biotin/avidin ligand binding arrangement, may be used in accordance with methodologies known in the art.

In some embodiments, the first antibody that becomes bound within the primary immune complexes may be detected by means of a second binding agent that has binding affinity for the antibody. In these cases, the second binding agent may be linked to a detectable label. The second binding agent is itself often an antibody, which may thus be termed a "secondary" antibody. The primary immune complexes are contacted with the labeled, secondary binding agent, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two-step approach. A second binding agent, such as an antibody, that has binding affinity for the antibody is used to form secondary immune complexes, as described above. After washing, the secondary immune complexes are contacted with a third binding agent or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

In another embodiment, a biotinylated monoclonal or polyclonal antibody is used to detect the target antigen(s), and a second step antibody is then used to detect the biotin attached to the complexed antibody. In that method the sample to be tested is first incubated in a solution comprising the first step antibody. If the target antigen is present, some of the antibody specifically binds to the antigen to form a biotinylated antibody/antigen complex. The antibody/antigen complex is then amplified by incubation in successive solutions of streptavidin (or avidin) and biotinylated DNA, and/or complementary biotinylated DNA, with each step adding additional biotin sites to the antibody/antigen complex. The amplification steps are repeated until a suitable level of amplification is achieved, at which point the sample is incubated in a solution comprising the second step antibody against biotin. This second step antibody is labeled, as for example with an enzyme that can be used to detect the presence of the antibody/antigen complex by histoenzymology using a chromogen substrate. With suitable amplification, a conjugate can be produced that is macroscopically visible.

In one embodiment, immunohistochemistry (IHC) is used for immunological detection. Using IHC, detection of B7-H4 in a sample can be achieved by targeting a sample with a binding agent, e.g., an anti-B7-H4 antibody or antigen-binding fragment thereof. The binding agent can be linked, either directly or indirectly to a detectable label or can be detected by another binding agent that is linked, either directly or indirectly to a detectable label. In one embodiment, 3,3'-diaminobenzidine (DAB) is used in the IHC assay to detect the primary antibody bound to B7-H4. In one embodiment, the concentration of the anti-B7-H4 antibody or antigen-binding fragment thereof in the IHC assay is about 1 µg/ml to about 50 µg/ml. In one embodiment, the concentration of the anti-B7-H4 antibody or antigen-binding fragment thereof in the IHC assay is about 1 µg/ml to about 20 µg/ml. In one embodiment, the concentration of the anti-B7-H4 antibody or antigen-binding fragment thereof in the IHC assay is about 10 µg/ml.

IHC can be performed on cells, cell pellets, tissues, preparations from blood, plasma, serum, or lymph fluid, etc. In some embodiments, the samples are fixed samples. In some embodiments, the samples are paraffin embedded samples. In some embodiments, the samples are formalin fixed and paraffin embedded samples.

In one embodiment, flow cytometry is used for immunological detection. Thus, for example, the number of antibodies bound per cell (ABC) can be assessed using flow cytometry.

Therapeutic Uses and Methods

In one aspect, presented herein are methods for treating a B7-H4-expressing cancer in a subject comprising administering a therapeutic anti-B7-H4 antibody or antigen-binding fragment thereof to the subject, wherein B7-H4 expression has been detected in a sample obtained from the subject using an antibody or antigen-binding fragment thereof provided herein. In some embodiments, the method further comprises detecting the B7-H4 in the sample obtained from the subject.

In a certain embodiment, provided herein the cancer is selected from the group consisting of: breast cancer (e.g., triple negative breast cancer, hormone receptor (HR) positive breast cancer, ductal carcinoma), endometrial carcinoma, ovarian cancer, non-small cell lung cancer (e.g., squamous cell carcinoma), pancreatic cancer, thyroid cancer, kidney cancer (e.g., renal cell carcinoma), and bladder cancer (e.g., urothelial cell carcinoma).

Therapeutic anti-B7-H4 antibodies or antigen-binding fragments thereof include, for example, 20502 and 22213 and antigen-binding fragments thereof. Amino acid and nucleotide sequences for the 20502 and 22213 antibodies are provided in Tables 9 and 10.

TABLE 9

20502 Antibody Amino Acid and Nucleotide Sequences

| Antibody Domain (AA/N) | Sequence (SEQ ID NO) |
|---|---|
| VH CDR1 (AA) | GSIKSGSYYWG (SEQ ID NO: 58) |
| VH CDR2 (AA) | NIYYSGSTYYNPSLRS (SEQ ID NO: 59) |
| VH CDR3 (AA) | AREGSYPNQFDP (SEQ ID NO: 60) |
| VL CDR1 (AA) | RASQSVSSNLA (SEQ ID NO: 61) |
| VL CDR2 (AA) | GASTRAT (SEQ ID NO: 62) |
| VL CDR3 (AA) | QQYHSFPFT (SEQ ID NO: 63) |
| VH (AA) | QLQLQESGPGLVKPSETLSLTCTVSGGSIKSGSYYWGWIRQPPGKGLEWIGNIYYSGSTYYNPSLRSRVTISVDTSKNQFSLKLSSVTAADTAVYYCAREGSYPNQFDPWGQGTLVTVSS (SEQ ID NO: 64) |
| VL (AA) | EIVMTQSPATLSVSPGERATLSCRASQSVSSNLAWYQQKPGQAPRLLIYGASTRATGIPARFSGSGSGTEFTLTISSLQSEDFAVYYCQQYHSFPFTFGGGTKVEIK (SEQ ID NO: 65) |
| VH FR1 (AA) | QLQLQESGPGLVKPSETLSLTCTVSG (SEQ ID NO: 66) |
| VH FR2 (AA) | WIRQPPGKGLEWIG (SEQ ID NO: 67) |
| VH FR3 (AA) | RVTISVDTSKNQFSLKLSSVTAADTAVYYC (SEQ ID NO: 68) |
| VH FR4 (AA) | WGQGTLVTVSS (SEQ ID NO: 69) |
| VL FR1 (AA) | EIVMTQSPATLSVSPGERATLSC (SEQ ID NO: 70) |
| VL FR2 (AA) | WYQQKPGQAPRLLIY (SEQ ID NO: 71) |
| VL FR3 (AA) | GIPARFSGSGSGTEFTLTISSLQSEDFAVYYC (SEQ ID NO: 72) |
| VL FR4 (AA) | FGGGTKVEIK (SEQ ID NO: 73) |

TABLE 9-continued

20502 Antibody Amino Acid and Nucleotide Sequences

| Antibody Domain (AA/N) | Sequence (SEQ ID NO) |
|---|---|
| Heavy Chain (AA) | QLQLQESGPGLVKPSETLSLTCTVSGGSIKSGSYYWGWIR QPPGKGLEWIGNIYYSGSTYYNPSLRSRVTISVDTSKNQFS LKLSSVTAADTAVYYCAREGSYPNQFDPWGQGTLVTVSS ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPELLGG PSVFLFPPKPKDTLMISRTPEVTCVVVDVSHEDPEVKFNW YVDGVEVHNAKTKPREEQYNSTYRVVSVLTVLHQDWLN GKEYKCKVSNKALPAPIEKTISKAKGQPREPQVYTLPPSR DELTKNQVSLTCLVKGFYPSDIAVEWESNGQPENNYKTT PPVLDSDGSFFLYSKLTVDKSRWQQGNVFSCSVMHEALH NHYTQKSLSLSPGK (SEQ ID NO: 74) |
| Light Chain (AA) | EIVMTQSPATLSVSPGERATLSCRASQSVSSNLAWYQQKP GQAPRLLIYGASTRATGIPARFSGSGSGTEFTLTISSLQSED FAVYYCQQYHSFPFTGGGTKVEIKRTVAAPSVFIFPPSDE QLKSGTASVVCLLNNFYPREAKVQWKVDNALQSGNSQE SVTEQDSKDSTYSLSSTLTLSKADYEKHKVYACEVTHQG LSSPVTKSFNRGEC (SEQ ID NO: 75) |
| VH (N) | CAGCTGCAGCTGCAGGAGTCGGGCCCAGGACTGGTGA AGCCTTCGGAGACCCTGTCCCTCACCTGCACTGTCTCTG GTGGCTCCATCAAAAGTGGTAGTTACTACTGGGGCTGG ATCCGCCAGCCCCCAGGGAAGGGGCTGGAGTGGATTG GGAACATCTATTATAGTGGGAGCACCTACTACAACCCG TCCCTCAGAAGTCGAGTCACCATATCCGTAGACACGTC CAAGAACCAGTTCTCCCTGAAGCTGAGTTCTGTGACCG CCGCAGACACGGCGGTGTACTACTGCGCCAGAGAAGG ATCTTACCCCAATCAGTTTGATCCATGGGGACAGGGTA CATTGGTCACCGTCTCCTCA (SEQ ID NO: 76) |
| VL (N) | GAAATAGTGATGACGCAGTCTCCAGCCACCCTGTCTGT GTCTCCAGGGGAAAGAGCCACCCTCTCCTGCAGGGCCA GTCAGAGTGTTAGCAGCAACTTAGCCTGGTACCAGCAG AAACCTGGCCAGGCTCCCAGGCTCCTCATCTATGGTGC ATCCACCAGGGCCACTGGTATCCCAGCCAGGTTCAGTG GCAGTGGGTCTGGGACAGAGTTCACTCTCACCATCAGC AGCCTGCAGTCTGAAGATTTTGCAGTTTATTACTGTCA GCAGTACCACTCCTTCCCTTTCACTTTTGGCGGAGGGA CCAAGGTTGAGATCAAA (SEQ ID NO: 77) |

TABLE 10

22213 Antibody Amino Acid and Nucleotide Sequences

| Antibody Domain (AA/N) | Sequence (SEQ ID NO) |
|---|---|
| VH CDR1 (AA) | GSIGRGSYYWG (SEQ ID NO: 32) |
| VH CDR2 (AA) | NIYYSGSTYYNPSLKS (SEQ ID NO: 33) |
| VH CDR3 (AA) | AREGSYTTVLNV (SEQ ID NO: 34) |
| VL CDR1 (AA) | RASQSVASSHLA (SEQ ID NO: 35) |
| VL CDR2 (AA) | DAVSRAT (SEQ ID NO: 36) |
| VL CDR3 (AA) | QQAASYPLT (SEQ ID NO: 37) |
| VH (AA) | QLQLQESGPGLVKPSETLSLTCTVSGGSIGRGSYYWGWIR QPPGKGLEWIGNIYYSGSTYYNPSLKSRVTISVDTSKNQFS LKLSSVTAADTAVYYCAREGSYTTVLNVWGQGTMVTVS S (SEQ ID NO: 54) |
| VL (AA) | EIVLTQSPGTLSLSPGERATLSCRASQSVASSHLAWYQQK PGQAPRLLIYDAVSRATGIPDRFSGSGSGTDFTLTISRLEPE DFAVYYCQQAASYPLTFGGGTKVEIK (SEQ ID NO: 55) |
| VH FR1 (AA) | QLQLQESGPGLVKPSETLSLTCTVSG (SEQ ID NO: 78) |

TABLE 10-continued

22213 Antibody Amino Acid and Nucleotide Sequences

| Antibody Domain (AA/N) | Sequence (SEQ ID NO) |
|---|---|
| VH FR2 (AA) | WIRQPPGKGLEWIG (SEQ ID NO: 79) |
| VH FR3 (AA) | RVTISVDTSKNQFSLKLSSVTAADTAVYYC (SEQ ID NO: 80) |
| VH FR4 (AA) | WGQGTMVTVSS (SEQ ID NO: 81) |
| VL FR1 (AA) | EIVLTQSPGTLSLSPGERATLSC (SEQ ID NO: 82) |
| VL FR2 (AA) | WYQQKPGQAPRLLIY (SEQ ID NO: 83) |
| VL FR3 (AA) | GIPDRFSGSGSGTDFTLTISRLEPEDFAVYYC (SEQ ID NO: 84) |
| VL FR4 (AA) | FGGGTKVEIK (SEQ ID NO: 98) |
| Heavy Chain (AA) | QLQLQESGPGLVKPSETLSLTCTVSGGSIGRGSYYWGWIRQPPGKGLEWIGNIYYSGSTYYNPSLKSRVTISVDTSKNQFSLKLSSVTAADTAVYYCAREGSYTTVLNVWGQGTMVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCRVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 56) |
| Light Chain (AA) | EIVLTQSPGTLSLSPGERATLSCRASQSVASSHLAWYQQKPGQAPRLLIYDAVSRATGIPDRFSGSGSGTDFTLTISRLEPEDFAVYYCQQAASYPLTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSPNRGEC (SEQ ID NO: 57) |
| VH (N) | CAGCTGCAGCTGCAGGAGTCGGGCCCAGGACTGGTGAAGCCTTCGGAGACCCTGTCCCTCACCTGCACTGTCTCTGGTGGCTCCATCGGGAGGGGGAGTTACTACTGGGGCTGGATCCGCCAGCCCCCAGGGAAGGGGCTGGAGTGGATTGGGAACATCTATTATAGTGGGAGCACCTACTACAACCCGTCCCTCAAGAGTCGAGTCACCATATCCGTAGACACGTCCAAGAACCAGTTCTCCCTGAAGCTGAGTTCTGTGACCGCCGCAGACACGGCGGTGTACTAGTGCGCCAGAGAAGGATCTTACACAACCGTGTTAAACGTATGGGGTCAGGGTACAATGGTCACCGTCTCCTCA (SEQ ID NO: 85) |
| VL (N) | GAAATTGTGTTGACGCAGTCTCCAGGCACCCTGTCTTTGTCTCCAGGGGAAAGAGCCACCCTCTCCTGCAGGGCCAGTCAGAGTGTTGCCAGCAGCCACTTAGCCTGGTACCAGCAGAAACCTGGCCAGGCTCCCAGGCTCCTCATCTATGACGCAGTCAGCAGGGCCACTGGCATCCCAGACAGGTTCAGTGGCAGTGGGTCTGGGACAGACTTCACTCTCACCATCAGCAGACTGGAGCCTGAAGATTTTGCAGTGTATTACTGTCAGCAGGCCGCCAGTTACCCTCTCACTTTTGGCGGAGGGACCAAGGTTGAGATCAAA (SEQ ID NO: 86) |

In some embodiments, the therapeutic anti-B7-H4 antibody or antigen-binding fragment comprises the VH CDR1, VH CDR2, VH CDR3, VL CDR1, VL CDR2, and VL CDR3 of 20502. The CDRs can be the Kabat-defined CDRs, the Chothia-defined CDRs, or the AbM-defined CDRs.

In some embodiments, the therapeutic anti-B7-H4 antibody or antigen-binding fragment comprises the VH CDR1, VH CDR2, VH CDR3, VL CDR1, VL CDR2, and VL CDR3 of 22213. The CDRs can be the Kabat-defined CDRs, the Chothia-defined CDRs, or the AbM-defined CDRs.

In some embodiments, the therapeutic anti-B7-H4 antibody or antigen-binding fragment comprises the VH CDR1, VH CDR2, VH CDR3, VL CDR1, VL CDR2, and VL CDR3 comprise the amino acid sequences of SEQ ID NOs:32-37, respectively. In some embodiments, the therapeutic anti-B7-H4 antibody or antigen-binding fragment comprises the VH CDR1, VH CDR2, VH CDR3, VL CDR1, VL CDR2, and VL CDR3 comprise the amino acid sequences of SEQ ID NOs:58-63, respectively.

In some embodiments, the therapeutic anti-B7-H4 antibody or antigen-binding fragment comprises a heavy chain variable region and a light chain variable region, wherein the heavy chain variable region comprises the amino acid sequence of SEQ ID NO:54. In some embodiments, the therapeutic anti-B7-H4 antibody or antigen-binding fragment comprises a heavy chain variable region and a light chain variable region, wherein the heavy chain variable region comprises the amino acid sequence of SEQ ID NO:64.

In some embodiments, the therapeutic anti-B7-H4 antibody or antigen-binding fragment comprises a heavy chain variable region and a light chain variable region, wherein the light chain variable region comprises the amino acid sequence of SEQ ID NO:55. In some embodiments, the therapeutic anti-B7-H4 antibody or antigen-binding fragment comprises a heavy chain variable region and a light chain variable region, wherein the light chain variable region comprises the amino acid sequence of SEQ ID NO:65.

In some embodiments, the therapeutic anti-B7-H4 antibody or antigen-binding fragment comprises a heavy chain variable region comprising the amino acid sequence of SEQ ID NO:54 and a light chain variable region comprising the amino acid sequence of SEQ ID NO:55. In some embodiments, the therapeutic anti-B7-H4 antibody or antigen-binding fragment comprises a heavy chain variable region comprising the amino acid sequence of SEQ ID NO:64 and a light chain variable region comprising the amino acid sequence of SEQ ID NO:65.

In some embodiments, the therapeutic anti-B7-H4 antibody or antigen-binding fragment comprises a heavy chain comprising the amino acid sequence of SEQ ID NO:56. In some embodiments, the therapeutic anti-B7-H4 antibody or antigen-binding fragment comprises a heavy chain comprising the amino acid sequence of SEQ ID NO:74.

In some embodiments, the therapeutic anti-B7-H4 antibody or antigen-binding fragment comprises a light chain comprising the amino acid sequence of SEQ ID NO:57. In some embodiments, the therapeutic anti-B7-H4 antibody or antigen-binding fragment comprises a light chain comprising the amino acid sequence of SEQ ID NO:75.

In some embodiments, the therapeutic anti-B7-H4 antibody or antigen-binding fragment comprises a heavy chain comprising the amino acid sequence of SEQ ID NO:56 and a light chain comprising the amino acid sequence of SEQ ID NO:57. In some embodiments, the therapeutic anti-B7-H4 antibody or antigen-binding fragment comprises) a heavy chain comprising the amino acid sequence of SEQ ID NO:74 and a light chain comprising the amino acid sequence of SEQ ID NO:75.

Kits

Provided herein are kits comprising one or more antibodies or antigen-binding fragments thereof described herein or conjugates (e.g., detection conjugates) thereof. As provided herein, kits can be used in diagnostic methods. In one embodiment, a kit comprises an antibody or antigen-binding fragment thereof described herein, preferably a purified antibody or antigen-binding fragment thereof, in one or more containers.

In a specific embodiment, kits described herein contain a substantially isolated B7-H4 antigen (e.g., human B7-H4) that can be used as a control. In specific embodiments, a kit provided herein can include a recombinantly produced or chemically synthesized B7-H4 antigen. The B7-H4 antigen provided in the kit can also be attached to a solid support.

In another specific embodiment, the kits described herein further comprise a control antibody or antigen-binding fragment thereof which does not react with a B7-H4 antigen. In another specific embodiment, kits described herein contain one or more elements for detecting the specific binding of an antibody or antigen-binding fragment thereof to a B7-H4 antigen (e.g., the antibody or antigen-binding fragment thereof can be conjugated to a detectable substrate such as a fluorescent compound, an enzyme, an enzymatic substrate, a radioactive compound, or a luminescent compound, or a second antibody or antigen-binding fragment thereof, which recognizes the first antibody or antigen-binding fragment thereof, can be conjugated to a detectable substrate). In a more specific embodiment, the detecting elements of the above described kit includes a solid support to which a B7-H4 antigen is attached. Such a kit can also include a non-attached reporter-labeled anti-mouse/rodent antibody or antigen-binding fragment thereof. In this embodiment, binding of the antibody or antigen-binding fragment thereof to the B7-H4 antigen can be detected by binding of the said reporter-labeled antibody or antigen-binding fragment thereof.

In another specific embodiment, the kits described herein further comprise a therapeutic anti-B7-H4 antibody or antigen-binding fragment thereof and/or information that a therapeutic anti-B7-H4 antibody or antigen-binding fragment thereof should be administered when B7-H4 is detected in a sample using an anti-B7-H4 antibody or antigen-binding fragment thereof provided herein.

The following examples are offered by way of illustration and not by way of limitation.

EXAMPLES

The examples in this Section (i.e., Section 6) are offered by way of illustration, and not by way of limitation.

Example 1: Hybridoma Generation

A panel of antibodies that selectively bind B7-H4 were generated using a recombinant soluble version of the B7-H4 extra cellular domain (ECD) protein:

```
                                           (SEQ ID NO: 20)
MASLGQILFWSIISIIIILAGAIALIIGFGISGRHSITVTTVASAGNIGED

GILSCTFEPDIKLSDIVIQWLKEGVLGLVHEFKEGKDELSEQDEMFRGRTA

VFADQVIVGNASLRLKNVQLTDAGTYKCYIITSKGKGNANLEYKTGAFSMP

EVNVDYNASSETLRCEAPRWFPQPTVVWASQVDQGANFSEVSNTSFELNSE

NVTMKVVSVLYNVTINNTYSCMIENDIAKATGDIKVTESEIKRRSHLQLLN

SKASGSEPKSSDKTHTCPPCPAPELLGGPSVFLFPPKPKDTLMISRTPEVT

CVVVDVSHEDPEVKFNWYVDGVEVHNAKTKPREEQYNSTYRVVSVLTVLHQ

DWLNGKEYKCKVSNKALPAPIEKTISKAKGQPREPQVYTLPPSRDELTKNQ

VSLTCLVKGFYPSDIAVEWESNGQPENNYKTTPPVLDSDGSFFLYSKLTVD

KSRWQQGNVFSCSVMHEALHNHYTQKSLSLSPGK.
```

Each hind footpad of a NZB/W mouse was injected with B7-H4 ECD protein resuspended in Sigma Adjuvant System® (Sigma-Aldrich, Inc., St. Louis, MO). Serum was taken 21 days after first boost and titered by enzyme-linked immunosorbant assay (ELISA) and fluorescence-activated cell sorting (FACS) and flow cytometry to ensure that the mouse had a good immune response. The ELISA and FACS screenings are described in detail in Examples 2 and 3, respectively. Three days after the final boost, popliteal node cells from titer-positive mice were fused with a mouse myeloma cell line (see, for example, Chuntharapai et al., 1997, Methods Enzymol. 288: 15-27). About 2880 rat hybridoma clones were generated.

Hybridoma clones generated by this process were then screened for production of monoclonal antibodies binding to the B7-H4 ECD protein (SEQ ID NO:20), the B7-H4 N-Terminal IgV-domain (amino acids 1-151)-huIgG Fc fusion protein (SEQ ID NO:21), and to HEK 293 cells stably expressing full length human B7-H4 (SEQ ID NO:1) on their surface.

(SEQ ID NO: 21)
MASLGQILFWSIISIIILAGAIALIIGFGISGRHSITVTTVASAGNIGED

GILSCTFEPDIKLSDIVIQWLKEGVLGLVHEFKEGKDELSEQDEMFRGRTA

VFADQVIVGNASLRLKNVQLTDAGTYKCYIITSKGKGNANLEYKTGAFSGS

EPKSSDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTCL

VKGFYPSDIAVEWESNGQPENNYKTTPPVLDSDGSFFLYSKLTVDKSRWQQ

GNVFSCSVMHEALHNHYTQKSLSLSPGK

Example 2: ELISA Screening

To screen the hybridoma clones generated in Example 1, ELISA was performed generally as described in Baker et al., 2002, Trends Biotechnol, 20:149-156.

Briefly, 96-well plates were coated with 50 μl of the B7-H4 ECD protein (SEQ ID NO:20) or the B7-H4 N-Terminal Fc fusion protein (SEQ ID NO:21) at a concentration of 2 μg/ml in coating buffer (0.05 M carbonate buffer, pH 9.6), sealed, and stored overnight at 40° C. After removing the coating solution, 200 μl of the assay/blocking solution containing 0.5% bovine serum albumin (BSA) and 0.05% Tween®-20 in PBS (pH 7.4) (ELISA diluent) was added to each well of a 96-well plate. The plates were incubated at room temperature for one hour with agitation. The wells were then washed three times with 300 μl of 0.05% Tween®-20 in PBS (wash buffer). After washing, 100 μl of hybridoma supernatant in ELISA diluent was added to each well, and the plates were incubated at room temperature for one hour with agitation. The wells were washed three times with wash buffer as previously described. After washing, 100 μl of a 1:1000 dilution of sheep anti-mouse IgG coupled to horseradish peroxidase in ELISA diluent was added to each well. The plates were incubated at room temperature for one hour with agitation, washed three times with wash buffer as previously described, and patted dry. The wells were developed by adding 100 μl of tetramethylbenzidine (TMB) microwell peroxidase substrate to each well and incubating at room temperature for 5-10 minutes or until a good color change was observed. Development was stopped by adding 100 μl of TMB Stop Solution to each well. Plates were analyzed at 650 nm.

Prebleed and polysera were used as controls. Prebleed samples contained mouse sera prior to immunization, and polysera samples contained mouse anti-sera obtained after immunizations. Antibodies that gave a positive ELISA signal were selected for further screening by fluorescence-activated cell sorting (FACS).

Example 3: FACS Screening

To further screen the hybridoma clones generated in Example 1, fluorescence-activated cell sorting (FACS) was performed using HEK 293 cells stably expressing the full length human B7-H4 (SEQ ID NO:1). Standard HEK 293 cell lines served as negative controls. Cells were resuspended and centrifuged at 500 g for 5 minutes at 40° C. Media was aspirated and cells were resuspended in BD FACSFlow™ Stain Buffer (BD Biosciences, San Jose, CA) with 1% fetal bovine serum (FBS) (cell staining buffer) at 40° C. Cells were centrifuged as previously described, media were aspirated, and cells were resuspended in cell staining buffer at 40° C. to a final concentration of 2×10$^6$ cells/ml. Cells were then added to 96-well round bottom plates at 50 μl/well. 100 μl of supernatant from each hybridoma clone were added to each well so that each hybridoma supernatant was incubated with one well containing either the HEK 293 cell line stably expressing B7-H4 or the negative control cell line. The plates were incubated on ice for 30 minutes and centrifuged as previously described. Then the supernatants were aspirated. Each well was resuspended in 200 μl of cell staining buffer at 40° C. Subsequently, the plates were centrifuged as previously described, and the cell staining buffer was aspirated. After the washing step, cells in each well were resuspended in 100 μl of a 1:1000 dilution of goat anti-mouse IgG Fc coupled to R-phycoerythrin (Jackson Immunoresearch, West Grove, PA) in cell staining buffer at 40° C., and the plates were incubated in the dark on ice for 30 minutes. The plates were centrifuged as previously described, and the supernatants were aspirated. Each well was resuspended in 200 μl of cell staining buffer at 40° C., and the plates were centrifuged as previously described. The cell staining buffer was aspirated. Cells in each well were resuspended in 200 μl of cell staining buffer at 40° C. and transferred to 1.2 ml micro titertubes. FACS was performed on a FACScan™ or FACSCalibur™ (BD Biosciences, San Jose, CA). Antibodies that showed cell binding in the FACS assay were selected for further screening by immunohistochemistry (IHC).

Example 4: IHC Screening

To further screen the hybridoma clones generated in Example 1, immunohistochemical (IHC) staining was performed on sections obtained from a subject with an invasive ductal carcinoma breast tumor. Formalin-fixed paraffin embedded (FFPE) sections were cut at 5 micron, air dried on Superfrost Plus charged slides, and baked for one hour at 60° C. Sections were deparaffinized and stained on a Discovery Ultra autostainer (Ventana Medical Systems, Tucson, AZ). After 1 hour of antigen retrieval with Ultra CC1 at 95° C., B7-H4 was detected with anti-B7-H4 mouse primary antibodies for 1 hour at room temperature followed by Omni-Map anti-Mouse HRP, ChromoMap 3,3'-diaminobenzidine (DAB) detection system and hematoxylin counterstaining, as per the manufacturer's instructions.

Figure 2:
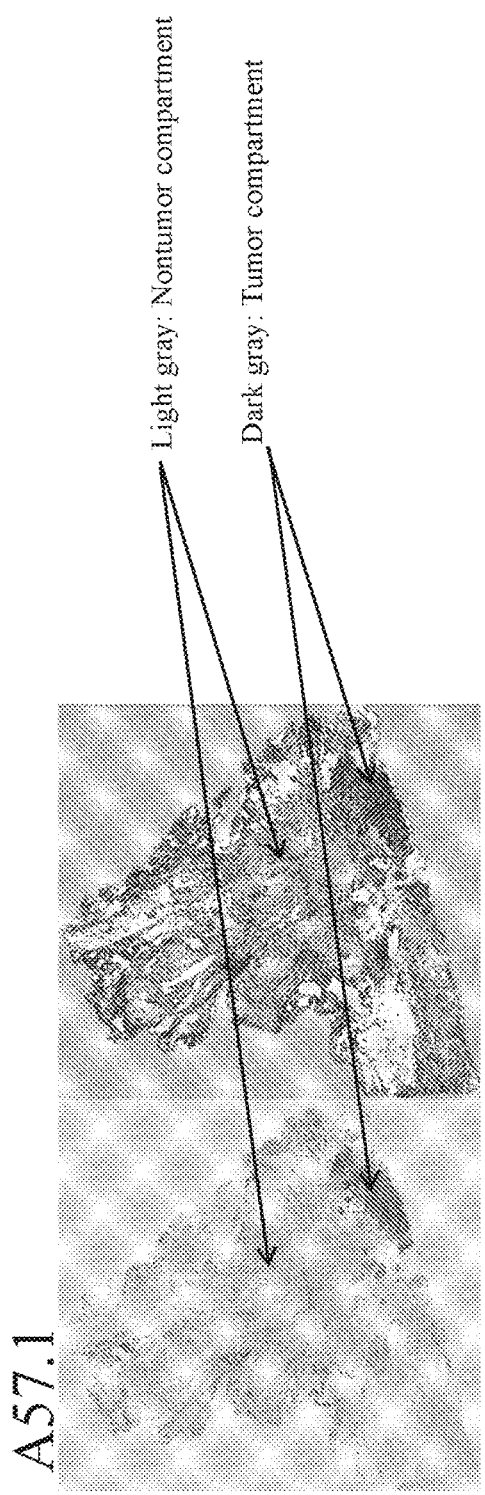
FIG. 2 shows computational image analysis (Definiens) of IHC staining. (See Example 4.)
Figure 2:
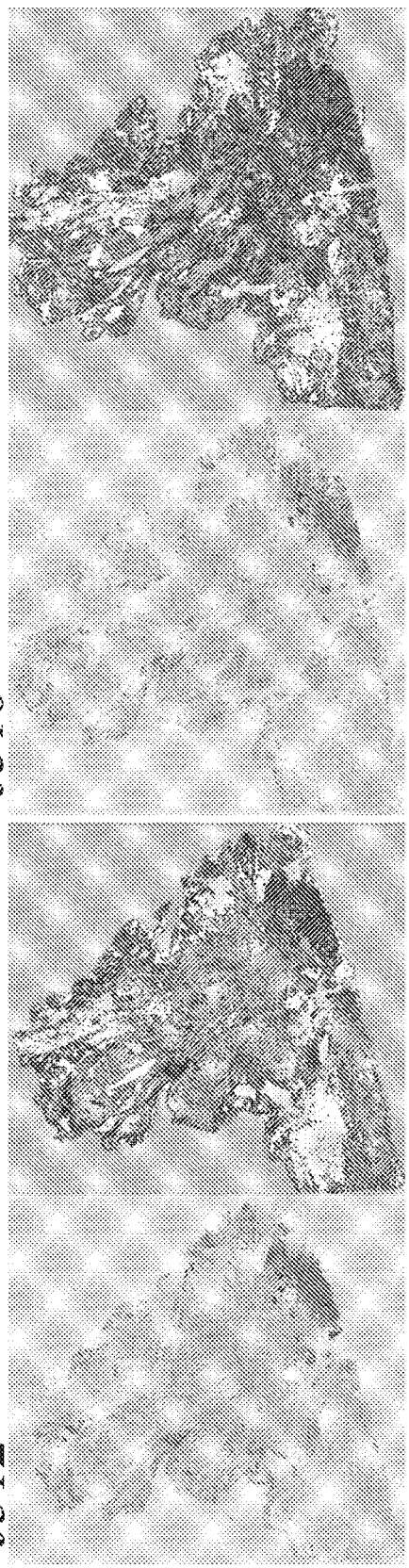
Figure 3:
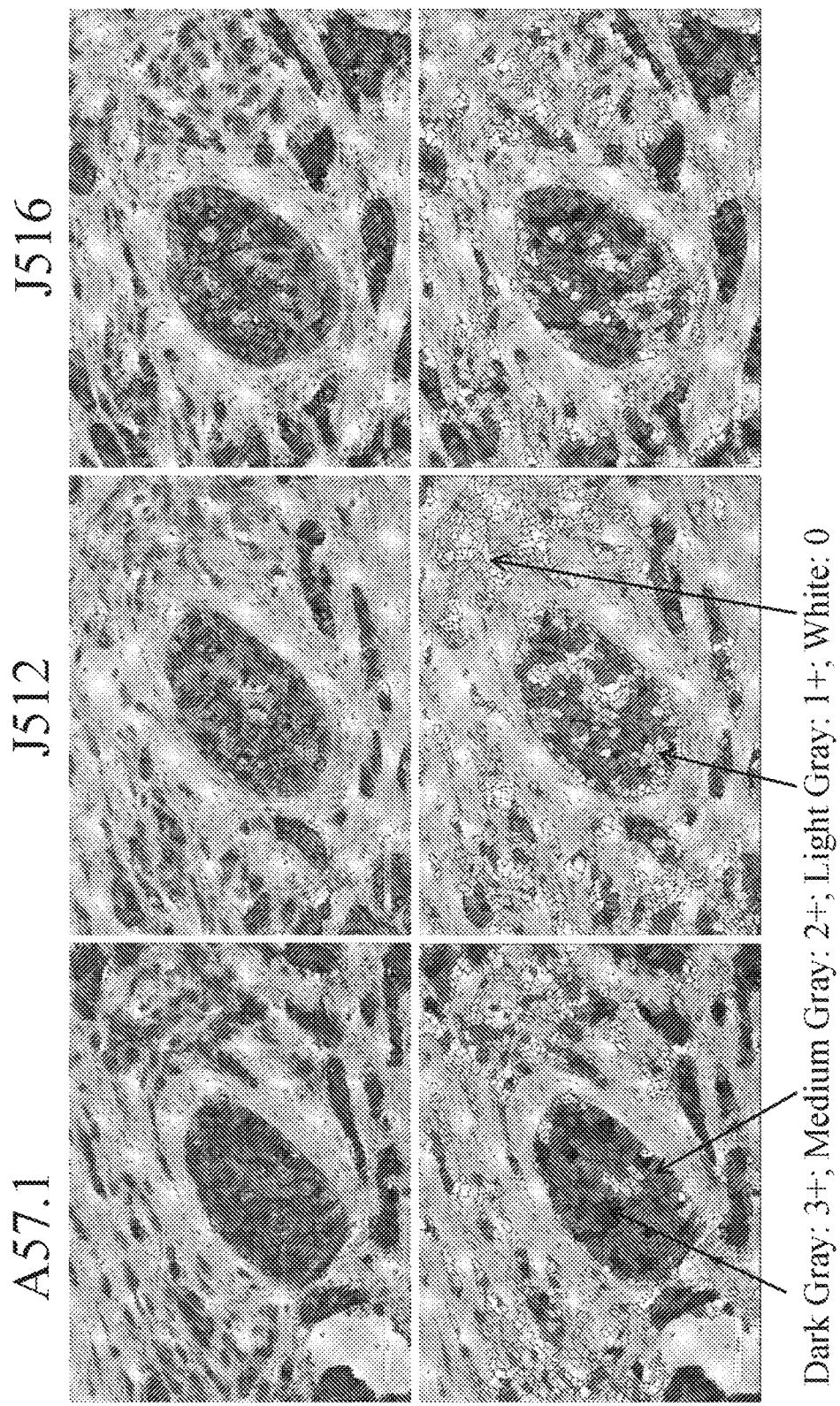
FIG. 3 shows the segmentation of positive cells with different intensity levels. (See Example 4.)
Figure 4:
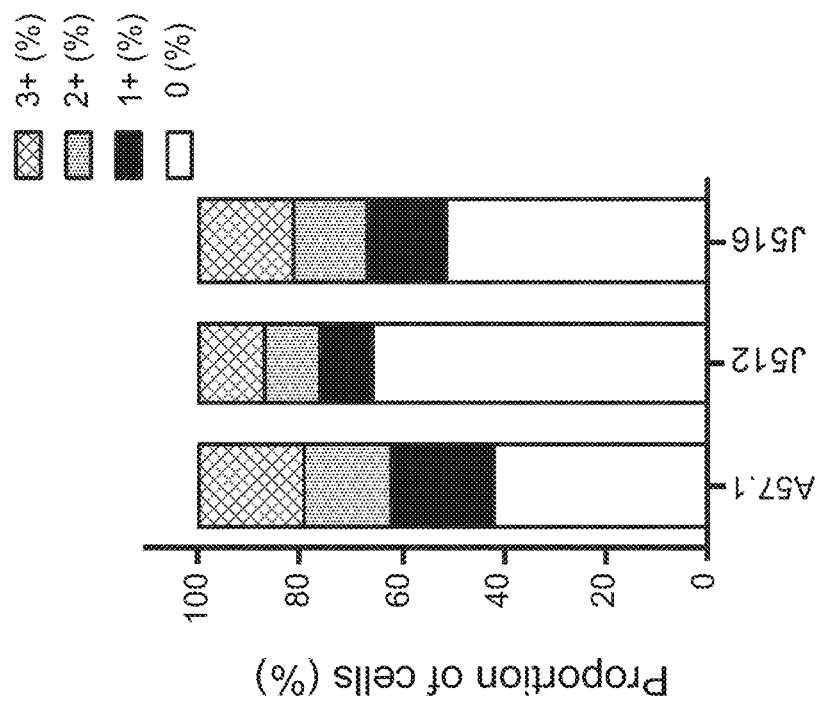
FIG. 4 shows the number and proportion of cells associated with each staining intensity level obtained using the anti-B7-H4 antibodies A57.1, AET_AB_J516, and AET_AB_J512. (See Example 4.)
Figure 5A:
FIGS. 5A-5C show a comparison of B7-H4 expression (DAB intensity) in whole cells, membranes, and cytoplasms of B7-H4 positive cells.
Figure 5A:
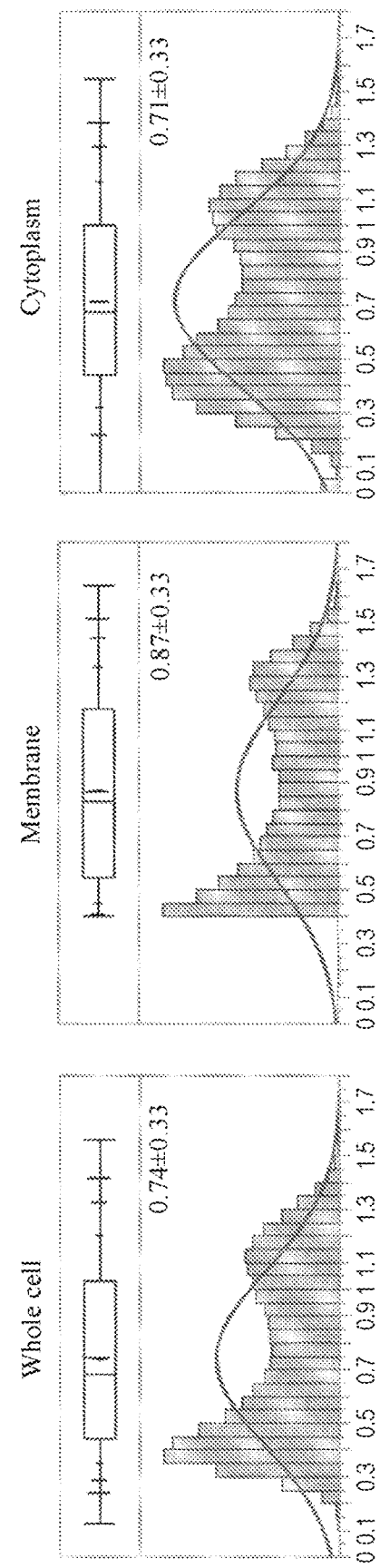
Figure 5B:
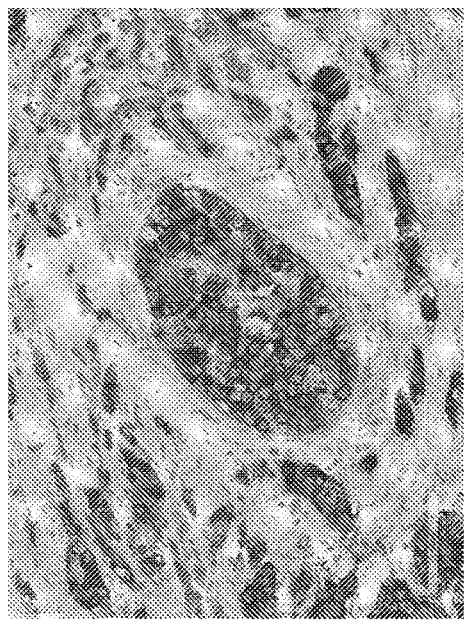
Figure 5B:
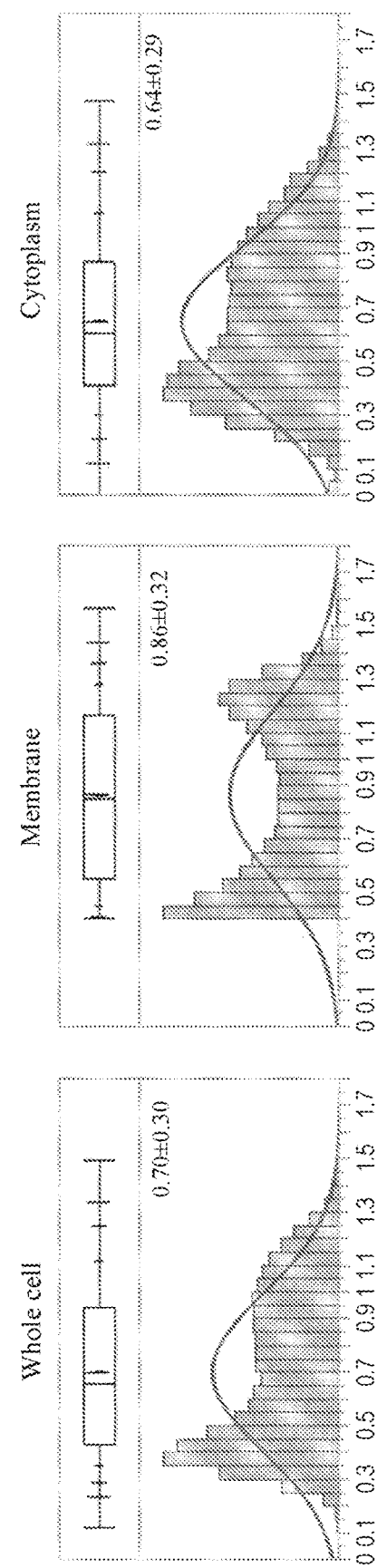
Figure 5C:
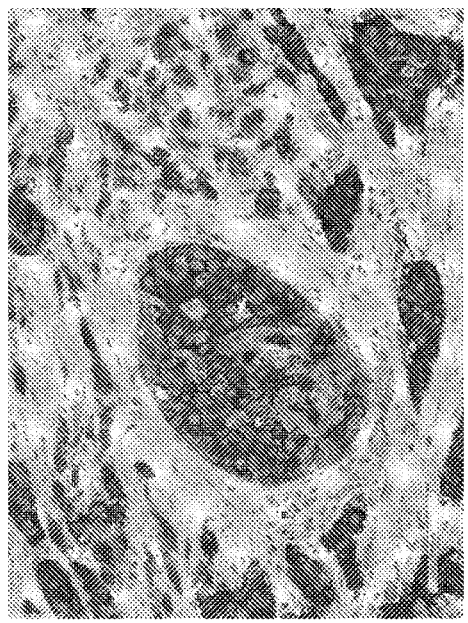
Figure 5C:
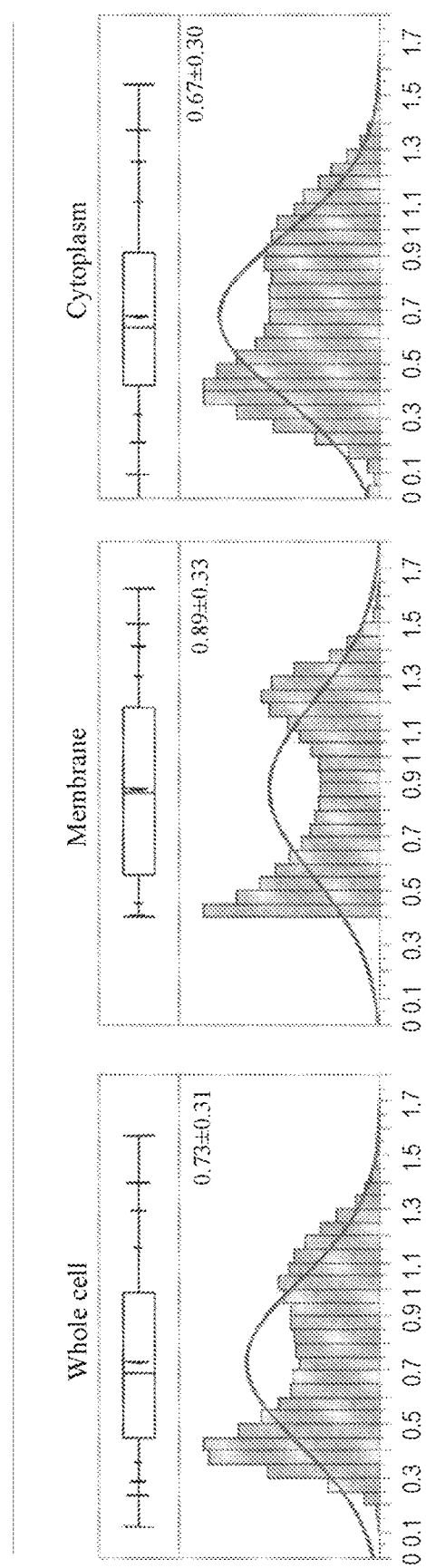

Seven anti-B7-H4 primary antibodies were used: six recombinant antibodies generated in Example 1 (at 10 μg/mL) along with A57.1 (see U.S. Pat. No. 7,619,068) (at 1.25 μg/mL), which was used as a control. The two recombinant antibodies (J516 and J512) detected B7-H4 on cell membranes and cytoplasm in a similar pattern to A57.1, with a majority of B7-H4-positive cells observed in the tumor compartment, as shown in FIGS. 1 and 2. The recombinant antibodies detected fewer B7-H4-expressing cells with 1+ signal intensity than A57.1 (35% by J512 vs 35% by J516% vs 58% by A57.1), as shown by FIGS. 3 and 4. When B7-H4 expression was measured by computational image analysis (Definiens, Cambridge, MA), J516 and J512 demonstrated a similar distribution of B7-H4 signal across the cellular compartments to A57.1, as shown in FIGS. 5A-5C.

Example 5: Sequence Determination

The sequence of the heavy chain (HC) and light chain (LC) anti-B7-H4 antibodies M6, M11, and M15, all of which showed IHC staining, were determined according to the following procedure.

RNA was harvested from hybridomas using Trizol reagent (Thermofisher Scientific, Carlsbad, CA), and cDNA was prepared using Smartscribe reverse transcriptase (Clontech, Mountain View, CA) and Advantage 2 polymerase (Clontech, Mountain View, CA). PCR was done using Phusion Taq polymerase (NEB, Ipswich, MA) under standard PCR conditions. PCR products were then cloned using Zero Blunt® TOPO® cloning kit (Thermofisher Scientific, Carlsbad, CA). Clones were screened for inserts, and multiple clones were sequenced to verify the original heavy chain and light chain gene sequences. The heavy chain and light chain-encoding polynucleotide sequences are provided in Table 8 above.

Anti-B7-H4 antibody variable domains were then subcloned into expression vectors with different Fc regions to generate antibodies with mouse IgG2a and mouse IgG1 constant regions. Anti-B7-H4 heavy chain variable domains were then cloned into expression vectors with different Fc regions to generate antibodies with mouse IgG2a and mouse IgG1 constant regions. Anti-B7-H4 light chain variable domains were cloned into expression vectors with mouse IgK constant region. Upon sequence verification, the isolated antibodies were assigned IDs J511-J516 as specified in Table 1 above.

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes.

Other embodiments are within the following claims.

What is claimed:

1. An isolated antibody or antigen-binding fragment thereof that specifically binds to human B7-H4, comprising a heavy chain variable region (VH) complementarity determining region (CDR) 1 comprising the amino acid sequence of SEQ ID NO:22, a VH CDR2 comprising the amino acid sequence of SEQ ID NO:23, a VH CDR3 comprising the amino acid sequence of SEQ ID NO:24, a light chain variable region (VL) CDR1 comprising the amino acid sequence of SEQ ID NO:25, a VL CDR2 comprising the amino acid sequence of SEQ ID NO:26, 27, or 28, and a VL CDR3 sequence comprising the amino acid sequence of SEQ ID NO:29.

2. The antibody or antigen-binding fragment thereof of claim 1, wherein the antibody or antigen-binding fragment thereof comprises a VH comprising the amino acid sequence of SEQ ID NO:6, 7, or 8 and/or a VL comprising the amino acid sequence of SEQ ID NO:9, 10, or 11.

3. An isolated antibody or antigen-binding fragment thereof that specifically binds to human B7-H4, comprising a heavy chain variable region and a light chain variable region comprising the amino acid sequences of:
   (a) SEQ ID NOs:6 and 9, respectively;
   (b) SEQ ID NOs:6 and 10, respectively;
   (c) SEQ ID NOs:6 and 11, respectively;
   (d) SEQ ID NOs:7 and 9, respectively;
   (e) SEQ ID NOs:7 and 10, respectively;
   (f) SEQ ID NOs:7 and 11, respectively;
   (g) SEQ ID NOs:8 and 9, respectively;
   (h) SEQ ID NOs:8 and 10, respectively; or
   (i) SEQ ID NOs:8 and 11, respectively.

4. The antibody or antigen-binding fragment thereof of claim 1, wherein the antibody or antigen-binding fragment comprises a heavy chain and a light chain comprising the amino acid sequences of:
   (a) SEQ IDNOs:16 and 19, respectively;
   (b) SEQ ID NOs: 16 and 30, respectively;
   (c) SEQ IDNOs:16 and 31, respectively;
   (d) SEQ IDNOs:17 and 19, respectively;
   (e) SEQ ID NOs: 17 and 30, respectively;
   (f) SEQ ID NOs: 17 and 31, respectively;
   (g) SEQ IDNOs:18 and 19, respectively;
   (h) SEQ ID NOs: 18 and 30, respectively;
   (i) SEQ IDNOs:18 and 31, respectively;
   (j) SEQ ID NOs: 89 and 19, respectively;
   (k) SEQ ID NOs: 90 and 19, respectively; or
   (l) SEQ ID NOs: 91 and 19, respectively.

5. The antibody or antigen binding fragment thereof of claim 1, which is an antigen binding fragment, wherein the antigen binding fragment comprises a Fab, Fab', F(ab')$_2$, single chain Fv (scFv), disulfide linked Fv, minibody, F(ab1)$_3$, diabody, (scFv)$_2$, or scFv-Fc.

6. The antibody or antigen-binding fragment thereof of claim 1, further comprising a detectable label.

7. An isolated polynucleotide comprising a nucleic acid molecule encoding the heavy chain variable region and the light chain variable region of the antibody or antigen-biding fragment thereof of claim 2.

8. An isolated polynucleotide comprising a nucleic acid molecule encoding the heavy chain variable region of the antibody or antigen-binding fragment thereof of claim 4 and the light chain variable region of the antibody or antigen-binding fragment thereof of claim 4.

9. An isolated vector comprising the polynucleotide of claim 8.

10. A host cell comprising the vector of claim 9.

11. A method of producing an antibody or antigen-binding fragment thereof that specifically binds to human B7-H4 comprising culturing the host cell of claim 10 so that the nucleic acid molecule is expressed and the antibody or antigen-biding fragment thereof is produced.

12. A kit comprising the antibody or antigen-binding fragment thereof of claim 1 and a) a detection reagent, b) a B7-H4 antigen, c) a therapeutic anti-B7-H4 antibody, or d) a combination of any of (a) through (c).

13. A method for detecting B7-H4 in a sample comprising contacting the sample with the antibody or antigen-binding fragment thereof of claim 1.

14. The method of claim 13, wherein the sample is obtained from a cancer in a subject.

15. The method of claim 14, wherein the cancer is selected from the group consisting of breast cancer, ductal carcinoma, endometrial carcinoma, ovarian cancer, non-small cell lung cancer, pancreatic cancer, thyroid cancer, kidney cancer and bladder cancer.

16. The method of claim 14, further comprising administering a therapeutic anti-B7-H4 antibody or antigen-binding fragment thereof to the subject after B7-H4 has been detected.

17. The method of claim 16, wherein the therapeutic antibody or antigen-binding fragment comprises (i) a heavy chain variable region comprising the amino acid sequence of SEQ ID NO:54 and a light chain variable region comprising the amino acid sequence of SEQ ID NO:55 or (ii) a heavy chain variable region comprising the amino acid sequence of SEQ ID NO:64 and a light chain variable region comprising the amino acid sequence of SEQ ID NO:65.

* * * * *